United States Patent
Masunaga et al.

(10) Patent No.: US 10,416,558 B2
(45) Date of Patent: *Sep. 17, 2019

(54) POSITIVE RESIST COMPOSITION, RESIST PATTERN FORMING PROCESS, AND PHOTOMASK BLANK

(71) Applicant: Shin-Etsu Chemical Co., Ltd., Tokyo (JP)

(72) Inventors: Keiichi Masunaga, Joetsu (JP); Satoshi Watanabe, Joetsu (JP); Masaaki Kotake, Joetsu (JP); Masaki Ohashi, Joetsu (JP)

(73) Assignee: SHIN-ETSU CHEMICAL CO., LTD., Tokyo (JP)

(*) Notice: Subject to any disclaimer, the term of this patent is extended or adjusted under 35 U.S.C. 154(b) by 75 days.

This patent is subject to a terminal disclaimer.

(21) Appl. No.: 15/656,203

(22) Filed: Jul. 21, 2017

(65) Prior Publication Data

US 2018/0039177 A1 Feb. 8, 2018

(30) Foreign Application Priority Data

Aug. 5, 2016 (JP) .................. 2016-154628

(51) Int. Cl.
| | |
|---|---|
| *G03F 7/039* | (2006.01) |
| *G03F 7/004* | (2006.01) |
| *G03F 7/16* | (2006.01) |
| *G03F 7/38* | (2006.01) |
| *G03F 7/20* | (2006.01) |
| *G03F 7/32* | (2006.01) |
| *C07C 381/12* | (2006.01) |
| *G03F 1/76* | (2012.01) |

(52) U.S. Cl.
CPC .......... *G03F 7/0392* (2013.01); *C07C 381/12* (2013.01); *G03F 1/76* (2013.01); *G03F 7/0045* (2013.01); *G03F 7/0046* (2013.01); *G03F 7/0048* (2013.01); *G03F 7/0395* (2013.01); *G03F 7/0397* (2013.01); *G03F 7/2037* (2013.01); *G03F 7/322* (2013.01); *G03F 7/162* (2013.01); *G03F 7/168* (2013.01); *G03F 7/38* (2013.01)

(58) Field of Classification Search
None
See application file for complete search history.

(56) References Cited

U.S. PATENT DOCUMENTS

| | | | |
|---|---|---|---|
| 6,479,210 B2 | 11/2002 | Kinoshita et al. | |
| 6,485,883 B2 | 11/2002 | Kodama et al. | |
| 6,492,091 B2 | 12/2002 | Kodama et al. | |
| 7,527,912 B2 | 5/2009 | Ohsawa et al. | |
| 8,202,677 B2 | 6/2012 | Takeda et al. | |
| 8,361,693 B2 | 1/2013 | Masunaga et al. | |
| 8,900,791 B2 | 12/2014 | Tsuchimura et al. | |
| 9,904,169 B2 * | 2/2018 | Adachi | G03F 7/405 |
| 10,120,279 B2 * | 11/2018 | Masunaga | C07C 69/753 |
| 10,248,022 B2 * | 4/2019 | Ohashi | C08K 5/375 |
| 2008/0241751 A1 * | 10/2008 | Takeda | G03F 7/0382 430/286.1 |
| 2009/0130595 A1 * | 5/2009 | Kawana | G03F 7/091 430/272.1 |
| 2009/0208872 A1 * | 8/2009 | Wolf | C07C 309/06 430/286.1 |
| 2010/0304302 A1 * | 12/2010 | Masunaga | G03F 7/0045 430/285.1 |
| 2010/0316955 A1 * | 12/2010 | Masunaga | G03F 7/0045 430/285.1 |
| 2011/0171580 A1 * | 7/2011 | Hatakeyama | C09D 125/18 430/285.1 |
| 2011/0177455 A1 * | 7/2011 | Harada | C08F 14/18 430/285.1 |
| 2015/0301451 A1 * | 10/2015 | Iwato | G03F 7/0045 430/281.1 |
| 2016/0299431 A1 * | 10/2016 | Adachi | G03F 7/405 |
| 2017/0329227 A1 * | 11/2017 | Ohashi | C08K 5/375 |
| 2018/0039177 A1 * | 2/2018 | Masunaga | G03F 7/0395 |

FOREIGN PATENT DOCUMENTS

| | | | | |
|---|---|---|---|---|
| JP | 11-327143 A | | 11/1999 | |
| JP | 2006-276759 | * | 10/2006 | ............ G03F 7/039 |
| JP | 2006-276760 | * | 10/2006 | ............ G03F 7/039 |
| JP | 3955384 B2 | | 8/2007 | |
| JP | 4226803 B2 | | 2/2009 | |
| JP | 2009-53518 A | | 3/2009 | |
| JP | 4231622 B2 | | 3/2009 | |
| JP | 2010-100604 A | | 5/2010 | |
| JP | 4575479 B2 | | 11/2010 | |
| JP | 2011-22564 A | | 2/2011 | |
| JP | 5083528 B2 | | 11/2012 | |
| JP | 2013-006827 | * | 1/2013 | .......... G03F 7/0004 |
| JP | 2013-072935 | * | 4/2013 | .......... G03F 7/0004 |

* cited by examiner

*Primary Examiner* — Martin J Angebranndt
(74) *Attorney, Agent, or Firm* — Westerman, Hattori, Daniels & Adrian, LLP

(57) ABSTRACT

A positive resist composition comprising a polymer adapted to be decomposed under the action of acid to increase its solubility in alkaline developer and a sulfonium compound of specific structure has a high resolution. When the resist composition is processed by lithography, a pattern with minimal LER can be formed.

12 Claims, 3 Drawing Sheets

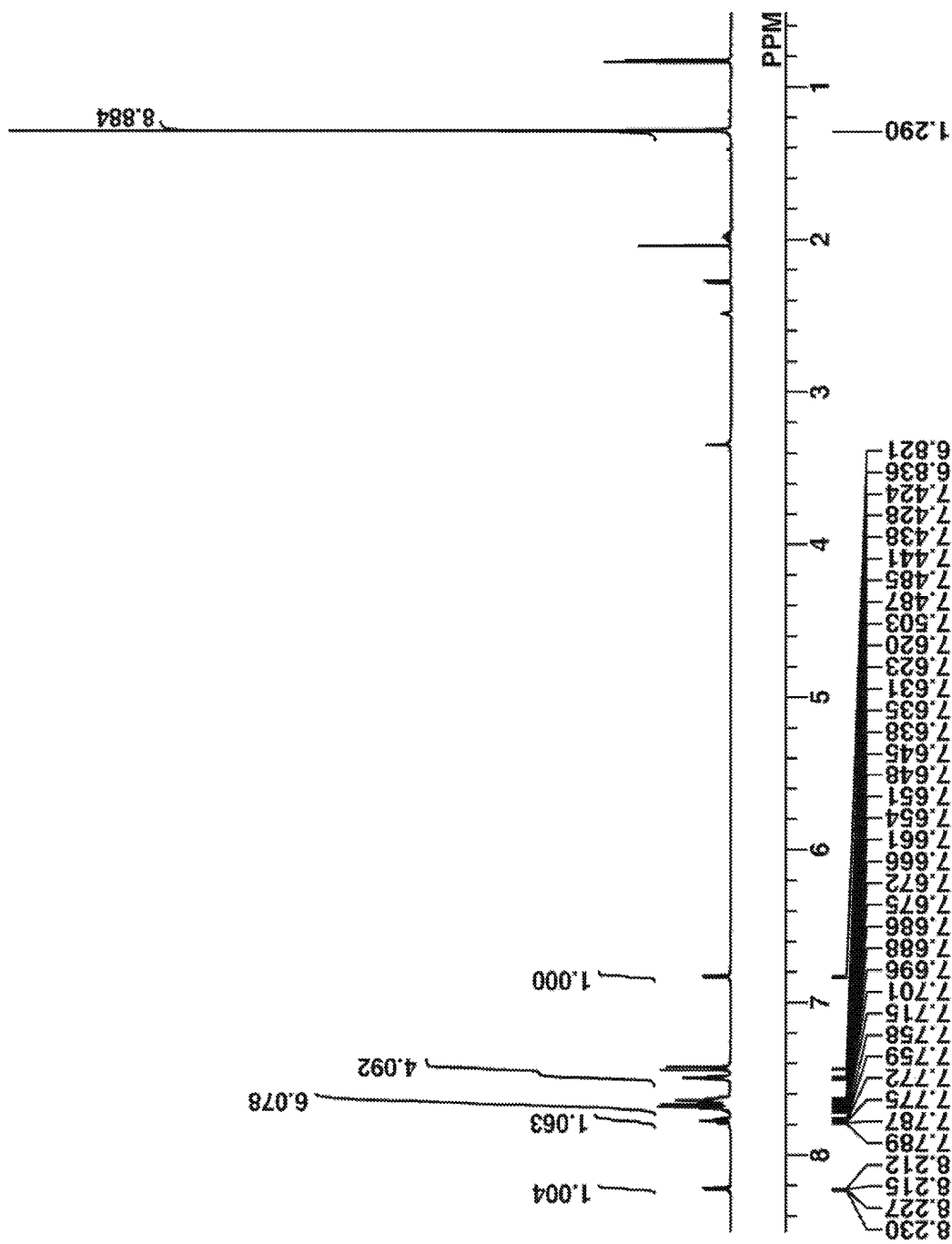

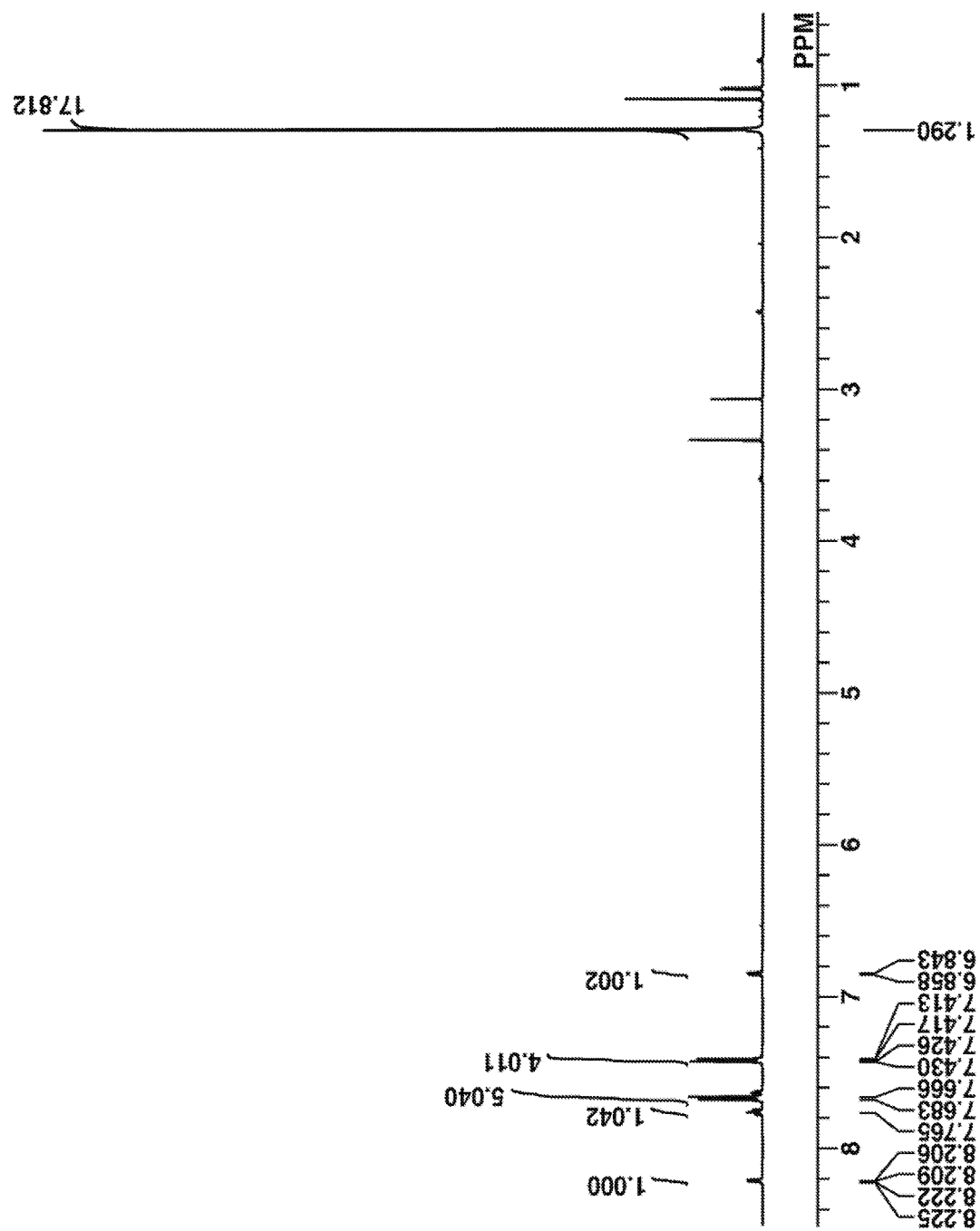

POSITIVE RESIST COMPOSITION, RESIST PATTERN FORMING PROCESS, AND PHOTOMASK BLANK

CROSS-REFERENCE TO RELATED APPLICATION

This non-provisional application claims priority under 35 U.S.C. § 119(a) on Patent Application No. 2016-154628 filed in Japan on Aug. 5, 2016, the entire contents of which are hereby incorporated by reference.

TECHNICAL FIELD

This invention relates to a positive resist composition, a resist pattern forming process, and a photomask blank.

BACKGROUND ART

To meet the recent demand for higher integration in integrated circuits, pattern formation to a finer feature size is required. Acid-catalyzed chemically amplified resist compositions are most often used in forming resist patterns with a feature size of 0.2 µm or less. High-energy radiation such as UV, deep-UV or electron beam (EB) is used as the light source for exposure of these resist compositions. In particular, while EB lithography is utilized as the ultra-fine microfabrication technique, it is also indispensable in processing a photomask blank to form a photomask for use in semiconductor device fabrication.

Polymers comprising a major proportion of aromatic structure having an acidic side chain, for example, polyhydroxystyrene have been widely used in resist materials for the KrF excimer laser lithography. These polymers are not used in resist materials for the ArF excimer laser lithography since they exhibit strong absorption at a wavelength of around 200 nm. These polymers, however, are expected to form useful resist materials for the BB and EUV lithography for forming patterns of finer size than the processing limit of ArF excimer laser because they offer high etching resistance.

Often used as the base polymer in positive resist compositions for EB and EUV lithography is a polymer having an acidic functional group on phenol side chain masked with an acid labile protective group. Upon exposure to high-energy radiation, the acid labile protective group is deprotected by the catalysis of an acid generated from a photoacid generator so that the polymer may turn soluble in alkaline developer. Typical of the acid labile protective group are tertiary alkyl, tert-butoxycarbonyl, and acetal groups. The use of protective groups requiring a relatively low level of activation energy for deprotection such as acetal groups offers the advantage that a resist film having a high sensitivity is obtainable. However, if the diffusion of generated acid is not fully controlled, deprotection reaction can occur even in the unexposed region of the resist film, giving rise to problems like degradation of line edge roughness (LER) and a lowering of in-plane uniformity of pattern line width (CDU).

Attempts were made to ameliorate resist sensitivity and pattern profile in a controlled way by properly selecting and combining components used in resist compositions and adjusting processing conditions. One outstanding problem is the diffusion of acid. Since acid diffusion has a material impact on the sensitivity and resolution of a chemically amplified resist composition, many studies are made on the acid diffusion problem.

Patent Documents 1 and 2 describe photoacid generators capable of generating bulky acids like benzenesulfonic acid upon exposure, for thereby controlling acid diffusion and reducing roughness. Since these acid generators are still insufficient in controlling acid diffusion, it is desired to have an acid generator with more controlled diffusion.

Patent Document 3 proposes to control acid diffusion in a resist composition by binding an acid generator capable of generating a sulfonic acid upon light exposure to a base polymer. This approach of controlling acid diffusion by binding recurring units capable of generating acid upon exposure to a base polymer is effective in forming a pattern with reduced LER. However, a problem arises with respect to the solubility in organic solvent of the base polymer having bound therein recurring units capable of generating acid upon exposure, depending on the structure and proportion of the bound units.

Patent Document 4 describes a resist composition comprising a polymer comprising recurring units having an acetal group and a sulfonium salt capable of generating an acid having a high acid strength such as fluoroalkanesulfonic acid. Regrettably, the pattern obtained therefrom has noticeable LER. This is because the acid strength of fluoroalkanesulfonic acid is too high for the deprotection of an acetal group requiring a relatively low level of activation energy for deprotection. So, even if acid diffusion is controlled, deprotection reaction can occur in the unexposed region with a minor amount of acid that has diffused thereto. The problem arises commonly with sulfonium salts capable of generating benzenesulfonic acids as described in Patent Documents 1 and 2. It is thus desired to have an acid generator capable of generating an acid having an appropriate strength to deprotect an acetal group.

While the aforementioned methodology of generating a bulky acid is effective for suppressing acid diffusion, the methodology of tailoring an acid diffusion inhibitor (also known as quencher) is also considered effective.

The acid diffusion inhibitor is, in fact, essential for controlling acid diffusion and improving resist performance. Studies have been made on the acid diffusion inhibitor while amines and weak acid onium salts have been generally used. The weak acid onium salts are exemplified in several patent documents. Patent Document 5 describes that the addition of triphenylsulfonium acetate ensures to form a satisfactory resist pattern without T-top profile, a difference in line width between isolated and grouped patterns, and standing waves. Patent Document 6 reports improvements in sensitivity, resolution and exposure margin by the addition of sulfonic acid ammonium salts or carboxylic acid ammonium salts. Also, Patent Document 7 describes that a resist composition for KrF or EB lithography comprising a PAG capable of generating a fluorinated carboxylic acid is improved in resolution and process latitude such as exposure margin and depth of focus. These compositions are used in the KrF, EB and $F_2$ lithography. Patent Document 8 describes a positive photosensitive composition for ArF excimer laser comprising a carboxylic acid onium salt. These systems are based on the mechanism that a salt exchange occurs between a weak acid onium salt and a strong acid (sulfonic acid) generated by another PAG upon exposure, to form a weak acid and a strong acid onium salt. That is, the strong acid (sulfonic acid) having high acidity is replaced by a weak acid (carboxylic acid), thereby suppressing acid-catalyzed decomposition reaction of acid labile group and reducing or controlling the distance of acid diffusion. The onium salt apparently functions as an acid diffusion inhibitor.

However, noticeable LER is still a problem in the recent progress of miniaturization when a resist composition comprising the foregoing carboxylic acid onium salt or fluorocarboxylic acid onium salt is used in patterning. It would be desirable to have an acid diffusion inhibitor capable of minimizing LER.

CITATION LIST

Patent Document 1: JP-A 2009-053518
Patent Document 2: JP-A 2010-100604
Patent Document 3: JP-A 2011-022564
Patent Document 4: JP 5083528
Patent Document 5: JP 3955384 (U.S. Pat. No. 6,479,210)
Patent Document 6: JP-A H11-327143
Patent Document 7: JP 4231622 (U.S. Pat. No. 6,485,883)
Patent Document 8: JP 4226803 (U.S. Pat. No. 6,492,091)
Patent Document 9: JP 4575479

DISCLOSURE OF INVENTION

An object of the invention is to provide a positive resist composition which exhibits a high resolution and can form a pattern with a minimal LER, and a resist pattern forming process.

The inventors have found that when a sulfonium compound of specific structure is formulated in a resist composition, the resist composition exhibits a high resolution and forms a pattern of good profile with a minimal LER.

In one aspect, the invention provides a positive resist composition comprising (A) a sulfonium compound having the formula (A) and (B) a base polymer containing a polymer comprising recurring units having the formula (B1), adapted to be decomposed under the action of acid to increase its solubility in alkaline developer.

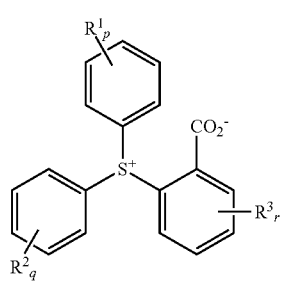

(A)

Herein $R^1$, $R^2$, and $R^3$ are each independently a $C_1$-$C_{20}$ straight, branched or cyclic monovalent hydrocarbon group which may contain a heteroatom, p and q are each independently an integer of 0 to 5, r is an integer of 0 to 4, in case of p=2 to 5, two adjoining groups $R^1$ may bond together to form a ring with the carbon atoms to which they are attached, in case of q=2 to 5, two adjoining groups $R^2$ may bond together to form a ring with the carbon atoms to which they are attached, in case of r=2 to 4, two adjoining groups $R^1$ may bond together to form a ring with the carbon atoms to which they are attached.

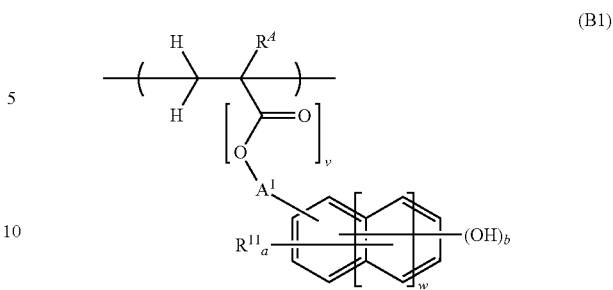

(B1)

Herein $R^A$ is hydrogen, fluorine, methyl or trifluoromethyl, $R^{11}$ is each independently halogen, an optionally halogenated $C_2$-$C_8$ straight, branched or cyclic acyloxy group, optionally halogenated $C_1$-$C_6$ straight, branched or cyclic alkyl group, or optionally halogenated $C_1$-$C_6$ straight, branched or cyclic alkoxy group, $A^1$ is a single bond or $C_1$-$C_{10}$ straight, branched or cyclic alkylene group in which an ether bond may intervene in a carbon-carbon bond, v is 0 or 1, w is an integer of 0 to 2, a is an integer satisfying 0 ≤ a ≤ 5+2w−b, and b is an integer of 1 to 3.

In a preferred embodiment, the polymer further comprises recurring units having the formula (B2):

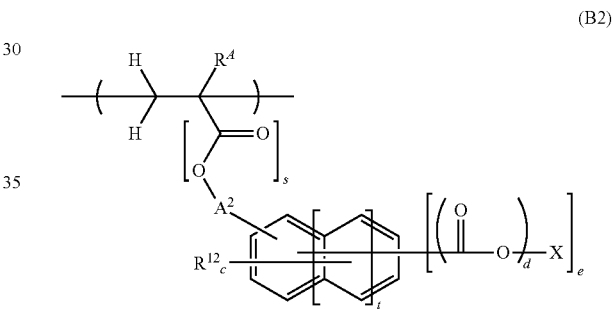

(B2)

wherein $R^A$ is as defined above, $R^{12}$ is each independently halogen, an optionally halogenated $C_2$-$C_8$ straight, branched or cyclic acyloxy group, optionally halogenated $C_1$-$C_6$ straight, branched or cyclic alkyl group, or optionally halogenated $C_1$-$C_6$ straight, branched or cyclic alkoxy group, $A^2$ is a single bond or $C_1$-$C_{10}$ straight, branched or cyclic alkylene group in which an ether bond may intervene in a carbon-carbon bond, s is 0 or 1, t is an integer of 0 to 2, c is an integer satisfying: 0≤c≤5+2t−e, d is 0 or 1, e is an integer of 1 to 3, in case of e=1, X is an acid labile group, and in case of e=2 or 3, X is hydrogen or an acid labile group, at least one X being an acid labile group.

In a preferred embodiment, the polymer further comprises recurring units of at least one type selected from units having the formulae (B3), (B4), and (B5):

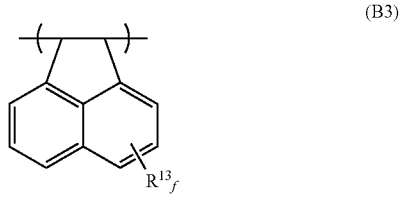

(B3)

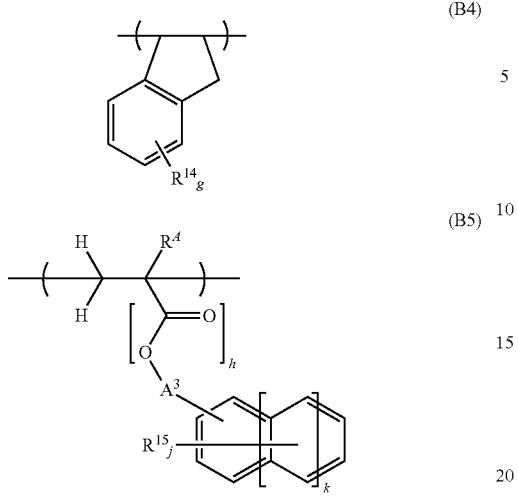

(B4)

(B5)

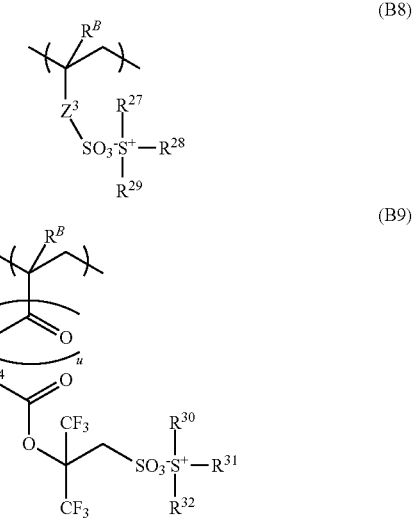

(B8)

(B9)

wherein $R^A$ is as defined above, $R^{13}$ and $R^{14}$ are each independently a hydroxyl group, halogen atom, acetoxy group, optionally halogenated $C_2$-$C_8$ straight, branched or cyclic acyloxy group, optionally halogenated $C_1$-$C_8$ straight, branched or cyclic alkyl group, optionally halogenated $C_1$-$C_8$ straight, branched or cyclic alkoxy group, or optionally halogenated $C_2$-$C_8$ straight, branched or cyclic alkylcarbonyloxy group, $R^{15}$ is an acetyl group, acetoxy group, $C_1$-$C_{20}$ straight, branched or cyclic alkyl group, $C_1$-$C_{20}$ straight, branched or cyclic alkoxy group, $C_2$-$C_{20}$ straight, branched or cyclic acyloxy group, $C_2$-$C_{20}$ straight, branched or cyclic alkoxyalkyl group, $C_2$-$C_{20}$ alkylthioalkyl group, halogen atom, nitro group, cyano group, sulfinyl group, or sulfonyl group, $A^3$ is a single bond or $C_1$-$C_{10}$ straight, branched or cyclic alkylene group in which an ether bond may intervene in a carbon-carbon bond, f and g are each independently an integer of 0 to 4, h is 0 or 1, j is an integer of 0 to 5, and k is an integer of 0 to 2.

In a preferred embodiment, the polymer further comprises recurring units of at least one type selected from units having the formulae (B6), (B7), (B8), and (B9):

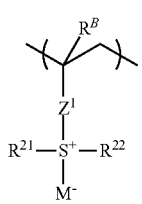

(B6)

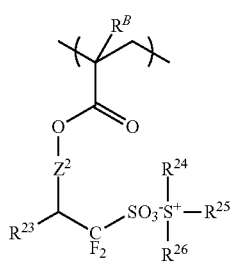

(B7)

wherein $R^B$ is each independently hydrogen or methyl, $Z^1$ is a single bond, phenylene group, —O—$Z^2$—, or —C(=O)—Z—$Z^{12}$—, $Z^{11}$ is —O— or —NH—, $Z^{12}$ is a $C_1$-$C_6$ straight, branched or cyclic alkylene, $C_2$-$C_6$ straight, branched or cyclic alkenylene or phenylene group, which may contain a carbonyl, ester, ether or hydroxy moiety, $Z^2$ is a single bond or —$Z^{21}$—C(=O)—O—, $Z^{21}$ is a $C_1$-$C_{20}$ straight, branched or cyclic divalent hydrocarbon group which may contain a heteroatom-containing moiety, $Z^3$ is a single bond, methylene, ethylene, phenylene, fluorinated phenylene, —O—$Z^{32}$—, or —C(=O)—$Z^{31}$—$Z^{32}$—, $Z^{31}$ is —O— or —NH—, $Z^{32}$ is a $C_1$-$C_6$ straight, branched or cyclic alkylene, $C_2$-$C_6$ straight, branched or cyclic alkenylene or phenylene group, which may contain a carbonyl, ester, ether or hydroxy moiety, $Z^4$ is a single bond or a $C_1$-$C_{30}$ straight, branched or cyclic divalent hydrocarbon group which may contain a heteroatom, u is 0 or 1, with the proviso that u is 0 when $Z^4$ is a single bond, $R^{21}$, $R^{22}$, $R^{24}$, $R^{25}$, $R^{26}$, $R^{27}$, $R^{28}$, $R^{29}$, $R^{30}$, $R^{31}$, and $R^{32}$ are each independently a $C_1$-$C_{20}$ straight, branched or cyclic monovalent hydrocarbon group which may contain a heteroatom-containing moiety, or $R^{21}$ and $R^{22}$ may bond together to form a ring with the sulfur atom to which they are attached, or any two of $R^{24}$, $R^{25}$ and $R^{25}$, any two of $R^{27}$, $R^{28}$ and $R^{29}$ or any two of $R^{30}$, $R^{31}$ and $R^{32}$ may bond together to form a ring with the sulfur atom to which they are attached, $R^{23}$ is hydrogen or trifluoromethyl, and $M^-$ is a non-nucleophilic counter ion.

The positive resist composition may further comprise (C) a polymer comprising recurring units having the formula (C1) and recurring units of at least one type selected from units having the formulae (C2), (C3), (C4), and (C5).

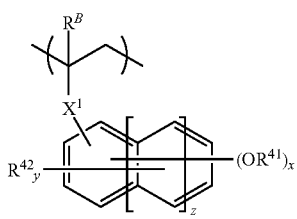

(C1)

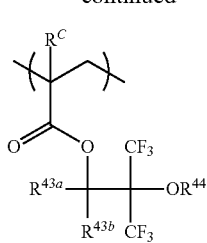
(C2)

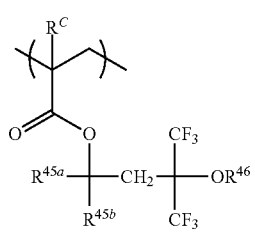
(C3)

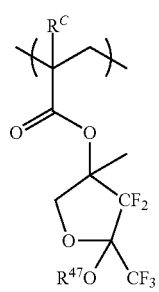
(C4)

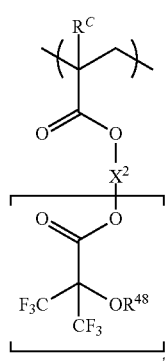
(C5)

Herein $R^B$ is each independently hydrogen or methyl, $R^C$ is each independently hydrogen, fluorine, methyl or trifluoromethyl, $R^{41}$ is hydrogen or a $C_1$-$C_5$ straight or branched monovalent hydrocarbon group in which a heteroatom may intervene in a carbon-carbon bond, $R^{42}$ is a $C_1$-$C_5$ straight or branched monovalent hydrocarbon group in which a heteroatom may intervene in a carbon-carbon bond, $R^{43a}$, $R^{43b}$, $R^{45a}$ and $R^{45b}$ are each independently hydrogen or a $C_1$-$C_{10}$ straight, branched or cyclic alkyl group, $R^{44}$, $R^{46}$, $R^{47}$ and $R^{48}$ are each independently hydrogen, a $C_1$-$C_{15}$ straight, branched or cyclic monovalent hydrocarbon group or monovalent fluorinated hydrocarbon group, or an acid labile group, with the proviso that an ether or carbonyl moiety may intervene in a carbon-carbon bond in the monovalent hydrocarbon groups or monovalent fluorinated hydrocarbon groups represented by $R^{44}$, $R^{46}$, $R^{47}$ and $R^{48}$, x is an integer of 1 to 3, y is an integer satisfying: 0≤y≤5+2z-x, z is 0 or 1, m is an integer of 1 to 3, $X^1$ is a single bond, —C(═O)—O— or —C(═O)—NH—, and $X^2$ is a $C_1$-$C_{20}$ straight, branched or cyclic (m+1)-valent hydrocarbon group or fluorinated hydrocarbon group.

The positive resist composition may further comprise (D) an organic solvent and/or (E) a photoacid generator.

In another aspect, the invention provides a resist pattern forming process comprising the steps of applying the positive resist composition defined above onto a processable substrate to form a resist film thereon, exposing the resist film patternwise to high-energy radiation, and developing the resist film in an alkaline developer to form a resist pattern.

Typically, the high-energy radiation is EUV or EB.

Preferably, the processable substrate has an outermost surface of silicon-containing material. Typically, the processable substrate is a photomask blank.

In a further aspect, the invention provides a photomask blank having coated thereon the positive resist composition defined above.

Advantageous Effects of Invention

By virtue of the action of the sulfonium compound, the positive resist composition of the invention is effective for controlling acid diffusion, exhibits a very high resolution, and forms a pattern with minimal LER, during the steps of resist film formation, exposure and pattern formation. By virtue of the action of the recurring units of formula (B1), the resist composition is fully soluble in alkaline developer and is improved in adhesion to a processable substrate when it is coated thereon as a resist film.

The pattern forming process using the positive resist composition can form a resist pattern with minimal LER while maintaining a high resolution. The invention is best suited for a micropatterning process, typically EUV or EB lithography.

BRIEF DESCRIPTION OF DRAWINGS

FIG. 2 is a diagram showing $^1$H-NMR spectrum of Compound Q-2 in Synthesis Example 1-9.

FIG. 3 is a diagram showing $^1$H-NMR spectrum of Compound Q-3 in Synthesis Example 1-10.

DESCRIPTION OF EMBODIMENTS

Figure 1:
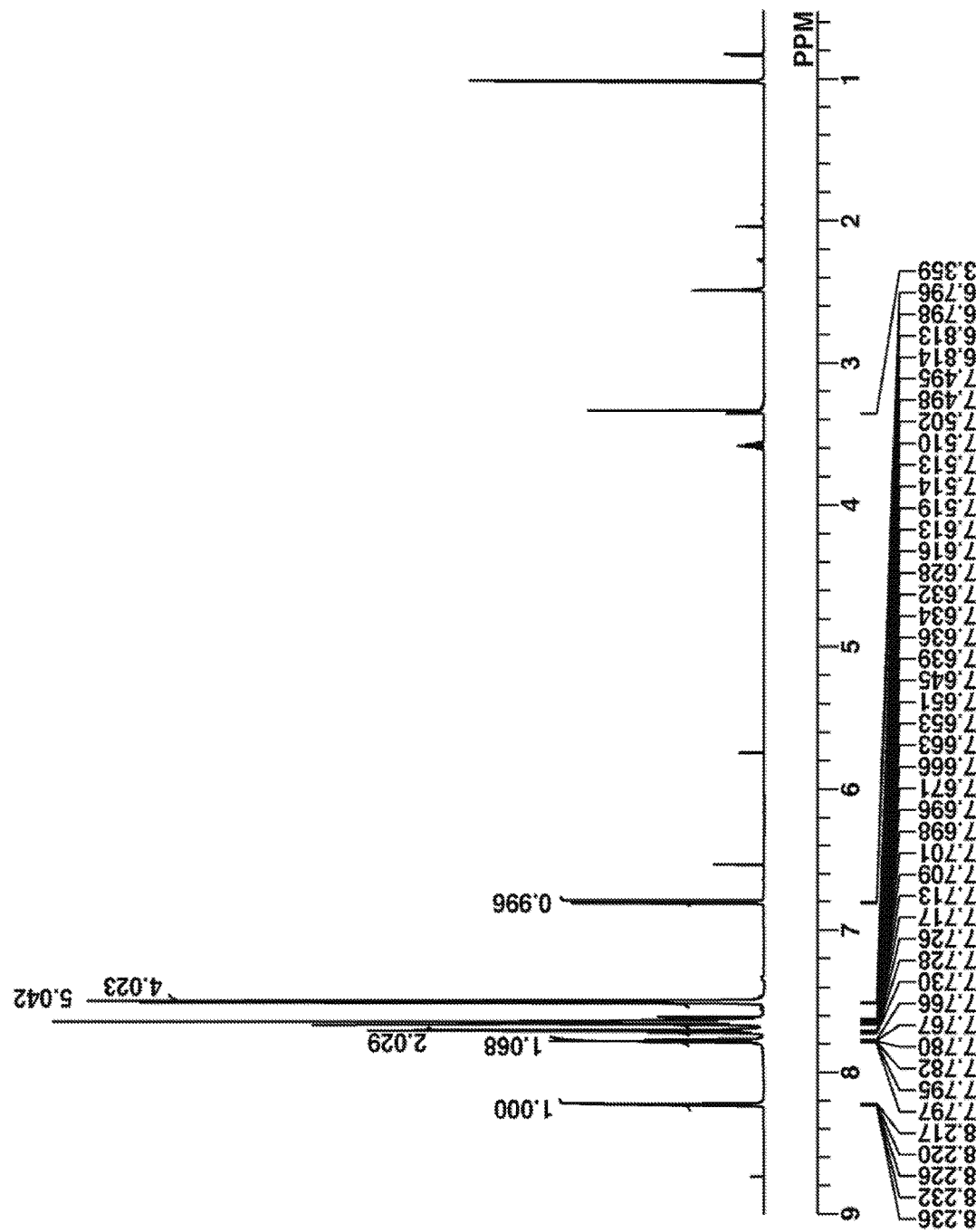
FIG. 1 is a diagram showing $^1$H-NMR spectrum of Compound Q-1 in Synthesis Example 1-8.

As used herein, the singular forms "a," "an" and "the" include plural referents unless the context clearly dictates otherwise. "Optional" or "optionally" means that the subsequently described event or circumstances may or may not occur, and that description includes instances where the event or circumstance occurs and instances where it does not.

The notation (Cn-Cm) means a group containing from n to m carbon atoms per group. In chemical formulae, the broken line depicts a valence bond.

The abbreviations and acronyms have the following meaning.

EB: electron beam
EUV: extreme ultraviolet
Mw: weight average molecular weight
Mn: number average molecular weight
Mw/Mn: molecular weight distribution or dispersity
GPC: gel permeation chromatography
PEB: post-exposure bake
PAG: photoacid generator
LER: line edge roughness It is understood that for some structures represented by chemical formulae, there can exist enantiomers and diastereomers because of the presence of asymmetric carbon atoms. In such a case, a single formula collectively represents all such isomers. The isomers may be used alone or in admixture.

Positive Resist Composition

Briefly stated, one embodiment of the invention is a positive tone resist composition comprising (A) a sulfonium compound and (B) a base polymer adapted to be decomposed under the action of acid to increase its solubility in alkaline developer.

(A) Sulfonium Compound

Component (A) in the positive resist composition is a sulfonium compound having the formula (A).

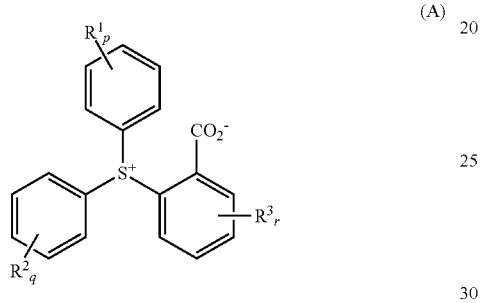

(A)

In formula (A), $R^1$, $R^2$ and $R^3$ are each independently a $C_1$-$C_{20}$ straight, branched or cyclic monovalent hydrocarbon group which may contain a heteroatom. Examples of the monovalent hydrocarbon group include alkyl groups such as methyl, ethyl, propyl, isopropyl, n-butyl, sec-butyl, t-butyl, n-pentyl, t-pentyl, n-hexyl, n-octyl, n-nonyl, n-decyl, cyclopentyl, cyclohexyl, 2-ethylhexyl, cyclopentylmethyl, cyclopentylethyl, cyclopentylbutyl, cyclohexylmethyl, cyclohexylethyl, cyclohexylbutyl, norbornyl, tricyclo[5.2.1.0$^{2,6}$] decanyl, adamantyl, and adamantylmethyl, and aryl groups such as phenyl, naphthyl, and anthracenyl. In these hydrocarbon groups, one or more hydrogen may be replaced by a moiety containing a heteroatom such as oxygen, sulfur, nitrogen or halogen, or a moiety containing a heteroatom such as oxygen, sulfur or nitrogen may intervene between carbon atoms, or one or more carbon atom may be replaced by a moiety containing a heteroatom such as oxygen, sulfur or nitrogen, so that the group may contain a hydroxy moiety, cyano moiety, carbonyl moiety, ether bond, thioether bond, ester bond, sulfonic acid ester bond, carbonate bond, carbamate bond, lactone ring, sultone ring, carboxylic anhydride or haloalkyl moiety.

In formula (A), p and q are each independently an integer of 0 to 5, and r is an integer of 0 to 4. Each of p, q and r is preferably 0 or 1 for ease of synthesis and availability of reactants.

When p is 2 to 5, two adjoining groups $R^1$ may bond together to form a ring with the carbon atoms to which they are attached. When q is 2 to 5, two adjoining groups $R^2$ may bond together to form a ring with the carbon atoms to which they are attached. When r is 2 to 4, two adjoining groups $R^3$ may bond together to form a ring with the carbon atoms to which they are attached.

Examples of the sulfonium compound having formula (A) are given below, but not limited thereto.

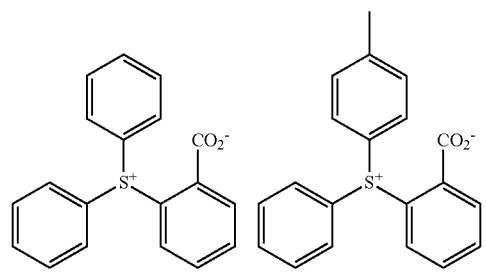

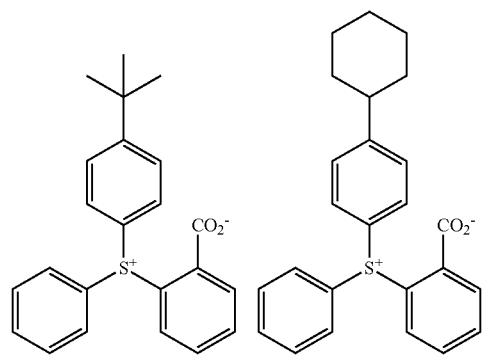

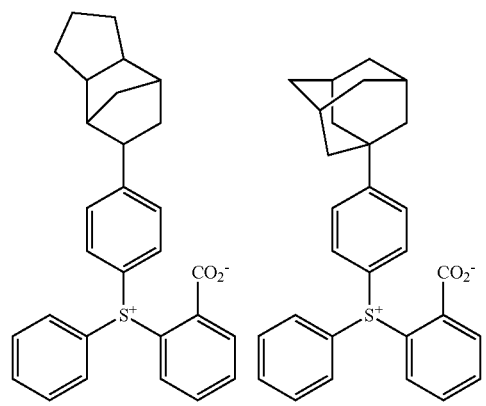

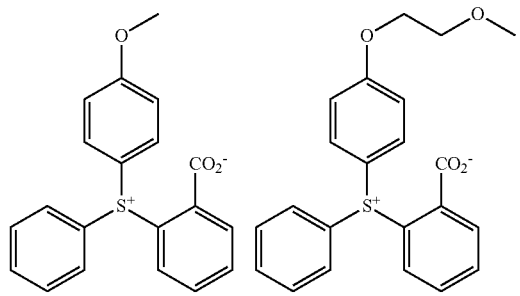

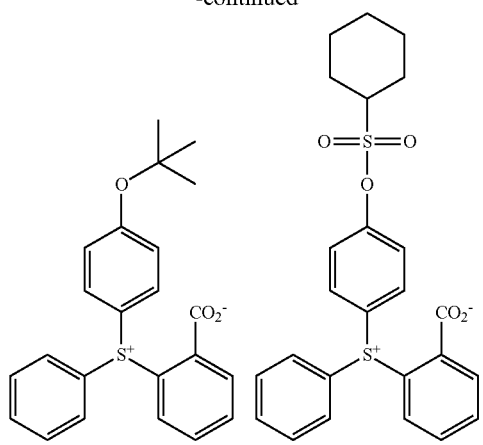
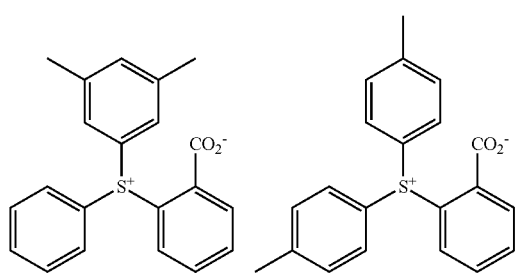
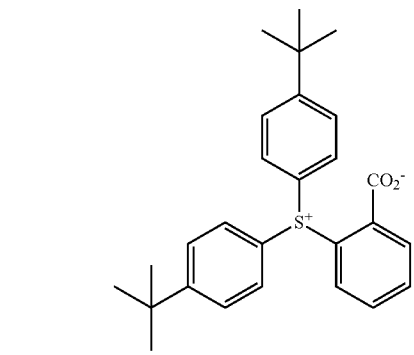
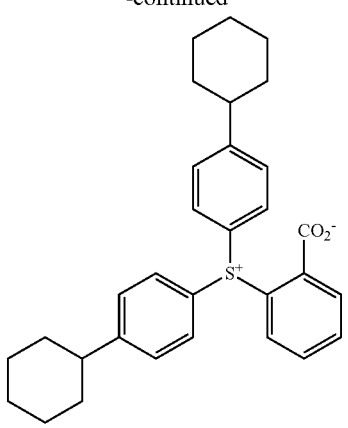
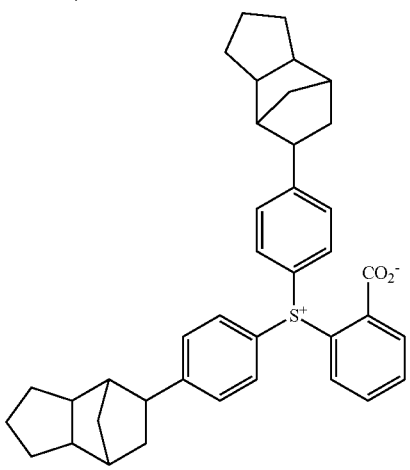
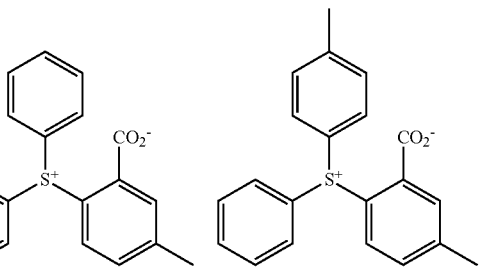
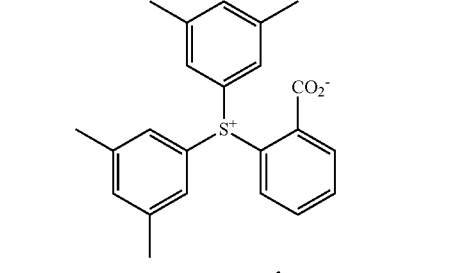
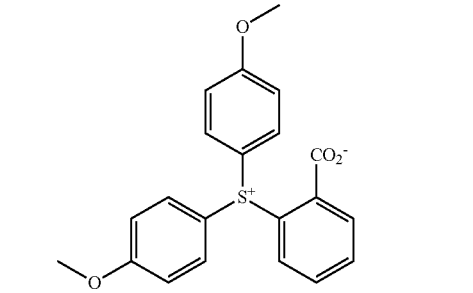

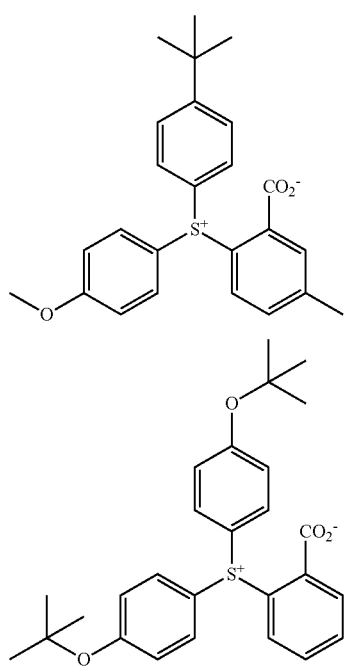

The sulfonium compound having formula (A) may be synthesized by a combination of well-known organic chemistry methods, preferably according to the scheme shown below.

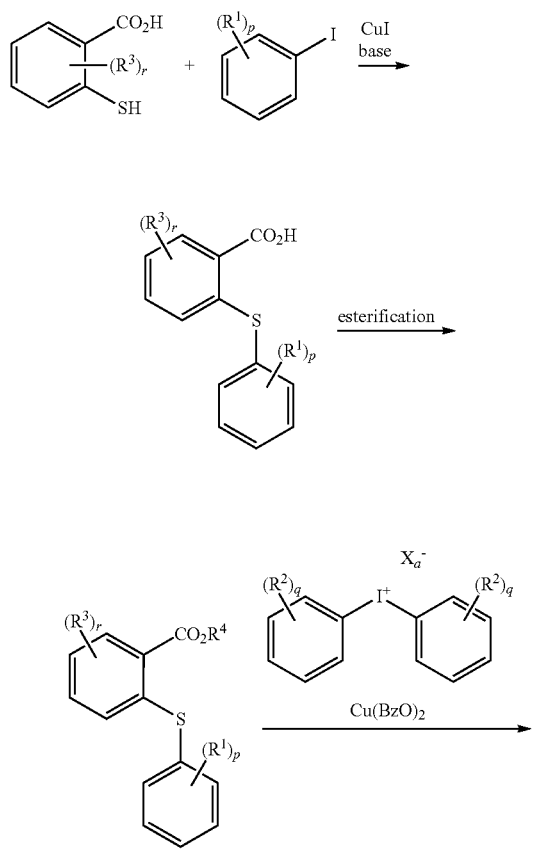

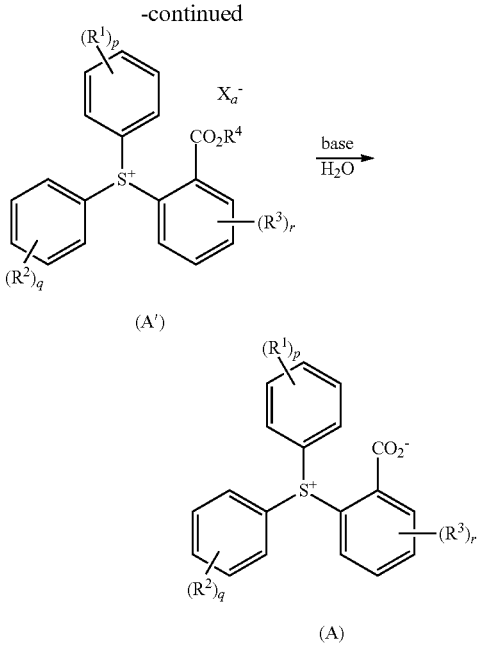

Herein $R^1$, $R^2$, $R^3$, p, q and r are as defined above, $R^4$ is a $C_1$-$C_{20}$ straight, branched or cyclic monovalent hydrocarbon group which may contain a heteroatom, and $X_a^-$ is an anion.

The first step is coupling reaction of an optionally substituted thiosalicylic acid with an optionally substituted iodobenzene in the presence of a copper catalyst to form a carboxyl-containing diarylsulfide compound. The second step is esterification of the carboxyl group on the carboxyl-containing diarylsulfide compound by a well-known organic chemistry technique. The esterification step is not particularly limited, and may be, for example, by heating in an alcohol solvent in the presence of an acid catalyst. The third step is reaction of the esterified compound with an iodonium salt in the presence of a copper catalyst to form a sulfonium salt (A'). The final step is by mixing the sulfonium salt (A') with water in the presence of a base to decompose the ester, and extracting into an organic layer, thus obtaining the target compound, sulfonium compound (A). Suitable bases used herein include sodium hydroxide and tetramethylammonium hydroxide, but are not limited thereto.

The superiority of the above process resides in the final step. By effecting ester hydrolysis and subsequent extraction in an organic layer, both formation of carboxylate and removal of counter anion $X_a^-$ in the precursor can be performed substantially in one step to complete a betaine form. The step is highly efficient. For example, when the precursor sulfonium salt is hydrolyzed using sodium hydroxide, a water-immiscible organic solvent is added during or after the reaction. Then the sodium salt having anion $X_a^-$ is extracted in the water layer at the end of reaction, while the sulfonium compound is extracted in the organic layer. Then the sulfonium compound is readily recovered from the organic layer. If the precursor sulfonium salt is synthesized by reaction with an iodonium salt without interposing the esterification step, undesirably the yield is reduced because the carboxyl group participates in decomposition of the iodonium salt.

In JP-A 2013-006827, a compound having carboxylate incorporated at the ortho position of sulfonium cation (for example, salt (I) in paragraph [0147]) is synthesized by reacting a carboxyl-containing sulfide with methyl iodide.

Although the synthesis of a sulfonium compound by methylation is a well-known technique, a sulfonium compound of triaryl type corresponding to the inventive structure cannot be synthesized with this technique. Therefore, the method for preparing a sulfonium compound of the invention is a novel method which is not achievable by the prior art steps.

The sulfonium compound defined herein functions quite effectively as an acid diffusion inhibitor or regulator when applied to a resist composition. As used herein, the term "acid diffusion inhibitor" is a compound which traps the acid generated by the PAG in the resist composition in the exposed region to prevent the acid from diffusing into the unexposed region for thereby forming the desired pattern.

The inventive sulfonium compound follows an acid diffusion controlling mechanism which is described below. The acid generated by the PAG in the resist composition in the exposed region should have a strong acidity enough to deprotect the acid labile group on the base polymer. For example, sulfonic acid which is fluorinated at α-position relative to sulfo group and sulfonic acid which is not fluorinated are generally used in the EB lithography. In a resist composition system where the PAO and the inventive sulfonium compound co-exist, the acid generated by the PAG is converted to a sulfonium salt via ion exchange with the sulfonium compound, and instead, the carboxylate moiety of the sulfonium compound is released as carboxylic acid. Differently stated, through ion exchange, the strong acid is quenched with the sulfonium compound. That is, the inventive sulfonium compound functions as an acid diffusion inhibitor. Although another mechanism that the inventive sulfonium compound is photo-decomposed whereby carboxylic acid is generated from the carboxylate moiety is contemplated, the generated carboxylic acid is a weak acid not having a sufficient acidity to deprotect the acid labile group on the base polymer.

The acid diffusion inhibitor in the form of a sulfonium compound tends to form a resist pattern with a reduced LWR as compared with the conventional quenchers in the form of amine compounds. This is presumably because salt exchange between strong acid and the inventive sulfonium compound is infinitely repeated. The site where strong acid is generated at the end of exposure shifts from the site where the onium salt of strong acid generation type is initially present. It is believed that since the cycle of photo-acid generation and salt exchange is repeated many times, the acid generation point is averaged, which leads to a resist pattern with reduced LWR after development.

As the compound that exerts a quencher effect via the same mechanism, Patent Document 8 and JP-A 2003-005376 report carboxylic acid onium salts, alkanesulfonic acid onium salts, and arylsulfonic acid onium salts as the acid diffusion inhibitor. On use of an alkanesulfonic acid onium salt or arylsulfonic acid onium salt, the generated acid has such an acid strength that part thereof in the highly exposed region may induce deprotection reaction of the acid labile group on the base polymer, leading to an increase of acid diffusion, which invite degradation of resist performance factors like resolution and CDU. Also in the case of alkane carboxylic acid onium salt, the generated carboxylic acid has a weak acidity and is not reactive with the acid labile group on the base polymer. Thus the carboxylic acid onium salt achieves some improvement as acid diffusion inhibitor, but fails to satisfy an overall balance of resolution, LER and CDU in a more miniaturized region.

In contrast, the inventive sulfonium compound achieves substantial improvements in resist performance, which are not achievable with the above-mentioned acid diffusion inhibitors. Although the reason is not clearly understood, the following reason is presumed. The inventive sulfonium compound is characterized by a betaine structure possessing a sulfonium cation and a carboxylate anion within a common molecule, and the carboxylate moiety at the ortho position relative to $S^+$. On trapping the acid from the co-existing PAG, the inventive sulfonium compound generates an acid which does not react with the acid labile group on the base polymer because it is weak acid. Although the reaction of the acid generated by the PAG with an onium salt type quencher is generally believed to be equilibration reaction rather than irreversible reaction, the reaction with the inventive sulfonium compound is estimated approximately irreversible. This is because it is advantageous from energy aspect that on catching proton from the generated acid, the sulfonium compound converts from the betaine structure to a stabler non-betaine type ionic compound. For the above reason, the inventive sulfonium compound has a very high acid diffusion controlling ability, resulting in improved LER and CDU.

In general, a sulfonium salt of weak acid is low soluble in organic solvents because of originally an ionic compound, and becomes substantially insoluble in organic solvents if it takes a betaine structure. Since the low solubility sulfonium salt is awkward to uniformly disperse in a resist composition, it can cause degradation of LER and defect generation. In contrast, the inventive sulfonium compound has superior solvent solubility. Although the reason is not well understood, it is presumed that the structural specificity of the inventive sulfonium compound that the carboxylate moiety is at the ortho position relative to $S^+$ participates in solubility. Due to this positional relationship, the inventive sulfonium compound assumes a hypervalent structure, and $S^+$ and carboxylate moiety are nearly in a three-center, four-electron bond having a shorter bond distance than the ordinary ionic bond, that is, a covalent bond, by which organic solvent solubility is increased. As a result, the inventive sulfonium compound is uniformly dispersed in the resist composition, which is one of factors accounting for improved LER and CDU.

An appropriate amount of the sulfonium compound (A) is 0.1 to 50 parts, more preferably 1 to 30 parts by weight per 100 parts by weight of the base polymer (B). As long as its amount is in the range, the sulfonium compound fully functions as an acid diffusion inhibitor, eliminating any performance problems such as sensitivity drop, solubility shortage, and foreign particles. The sulfonium compound (A) may be used alone or in admixture of two or more.

(B) Base Polymer

The positive resist composition also comprises (B) a base polymer containing a polymer comprising recurring units having the formula (B1). It is noted that the recurring unit having formula (B1) is simply referred to as recurring unit (B1).

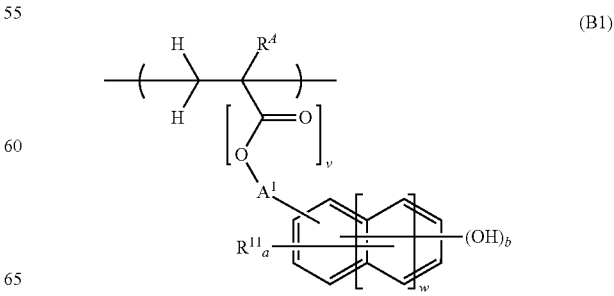

(B1)

In formula (B1), $R^A$ is hydrogen, fluorine, methyl or trifluoromethyl. $R^{11}$ is each independently halogen, an optionally halogenated $C_2$-$C_8$ straight, branched or cyclic acyloxy group, optionally halogenated $C_1$-$C_6$ straight, branched or cyclic alkyl group, or optionally halogenated $C_1$-$C_6$ straight, branched or cyclic alkoxy group. $A^1$ is a single bond or a $C_1$-$C_{10}$ straight, branched or cyclic alkylene group in which an ether bond may intervene in a carbon-carbon bond, v is 0 or 1, w is an integer of 0 to 2, a is an integer in the range: $0 \leq a \leq 5+2w-b$, and b is an Integer of 1 to 3.

Where the recurring units (B1) are free of a linker (—CO—O-$A^1$-), that is, have formula (B1) wherein v=0 and $A^1$ is a single bond, suitable recurring units (B1) include those derived from 3-hydroxystyrene, 4-hydroxystyrene, 5-hydroxy-2-vinylnaphthalene, and 6-hydroxy-2-vinylnaphthalene.

Where the recurring units (B1) have a linker (—CO—O-$A^1$-), preferred examples of the recurring units (B1) are given below, but not limited thereto.

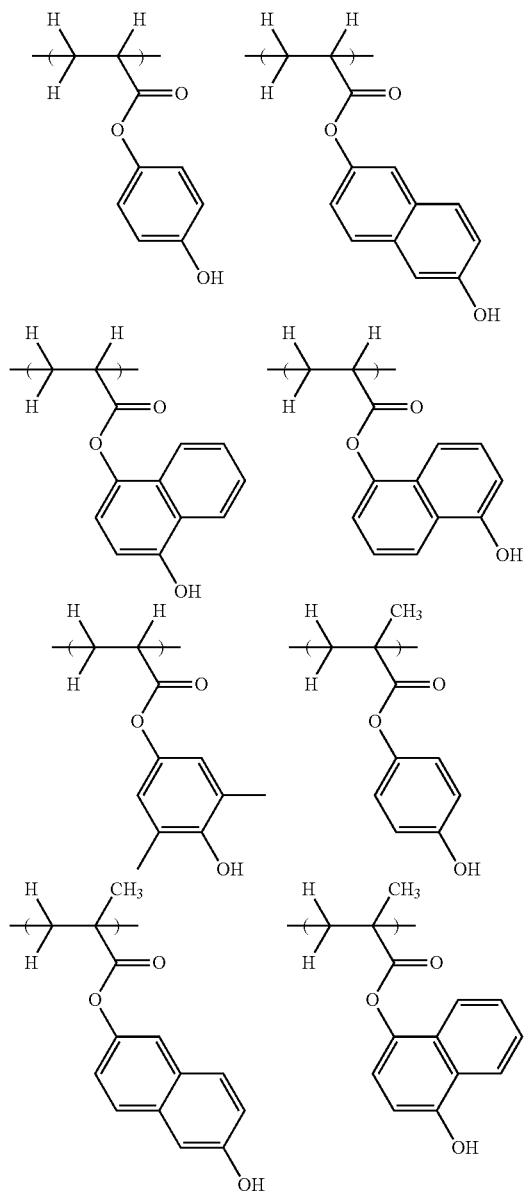

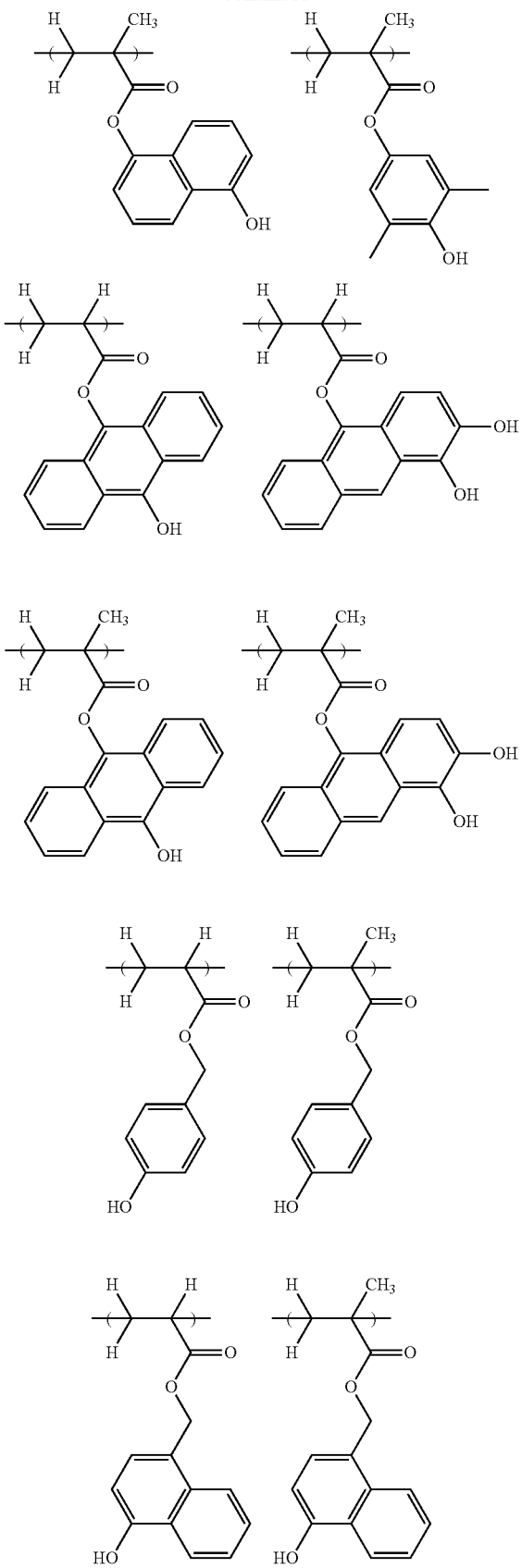

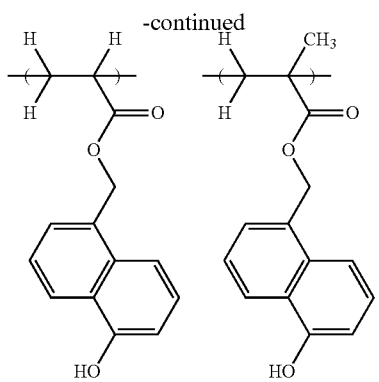

The recurring units (B1) may be of one type or a mixture of two or more types. The recurring units (B1) are incorporated in an amount of preferably 10 to 95 mol %, more preferably 40 to 90 mol %, based on the entire recurring units of the polymer. It is noted that when recurring units of at least one type selected from recurring units having formulae (B3) and (B4) for imparting higher etch resistance are also incorporated in the polymer and these units have a phenolic hydroxyl group substituted thereon, the above-defined range is inclusive of an amount of these units (B3) and (B4).

In order that the resist composition serve as a positive resist composition wherein the exposed region of a resist film is dissolved in alkaline aqueous solution, the polymer should preferably further comprise units having an acidic functional group protected with an acid labile group, that is, units which are protected with an acid labile group, but turn alkali soluble under the action of acid. Since the acid labile groups (protective groups) in the recurring units undergo deprotection reaction under the action of acid, the polymer turns more soluble in alkaline developer.

Of the recurring units which are protected with an acid labile group, but turn alkali soluble under the action of acid, recurring units having the formula (B2) are most preferred. They are also referred to as recurring units (B2).

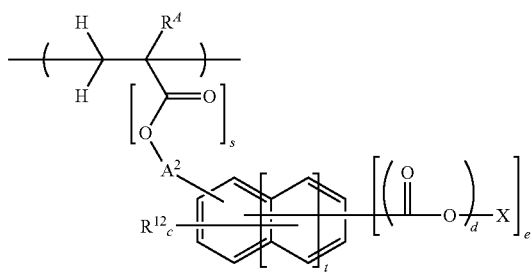

Herein $R^A$ is as defined above. $R^{12}$ is each independently halogen, an optionally halogenated $C_2$-$C_8$ straight, branched or cyclic acyloxy group, optionally halogenated $C_1$-$C_6$ straight, branched or cyclic alkyl group, or optionally halogenated $C_1$-$C_6$ straight, branched or cyclic alkoxy group. $A^2$ is a single bond or $C_1$-$C_{10}$ straight, branched or cyclic alkylene group in which an ether bond may intervene in a carbon-carbon bond, s is 0 or 1, t is an integer of 0 to 2, c is an integer satisfying: 0 s c s 5+2t−e, d is 0 or 1, and e is an integer of 1 to 3. When e is 1, X is an acid labile group. When e is 2 or 3, X is hydrogen or an acid labile group, at least one X being an acid labile group.

The recurring unit (B2) is the unit in which at least one of phenolic hydroxyl groups attached to aromatic ring is protected with an acid labile group, or a carboxyl group attached to aromatic ring is protected with an acid labile group. The acid labile group used herein is not particularly limited. It may be any of acid labile groups which are commonly used in many well-known chemically amplified resist compositions as long as it is eliminated with an acid to provide an acidic group.

The acid labile group is typically selected from tertiary alkyl groups and acetal groups. A choice of tertiary alkyl as the acid labile group is preferred in that when a resist film is formed as thin as 10 to 100 nm, and a fine pattern having a line width of 45 nm or less is printed therein, the pattern is provided with minimal LER. Of the tertiary alkyl groups, those of 4 to 18 carbon atoms are preferred because a corresponding monomer subject to polymerization may be recovered by distillation. In the tertiary alkyl group, suitable alkyl substituents on tertiary carbon are straight, branched or cyclic $C_1$-$C_{15}$ alkyl groups, some of which may contain an oxygen-containing functional group such as ether bond or carbonyl; and alkyl substituents on tertiary carbon may bond together to form a ring.

Examples of the alkyl substituent include methyl, ethyl, propyl, adamantyl, norbornyl, tetrahydrofuran-2-yl, 7-oxanorbornan-2-yl, cyclopentyl, 2-tetrahydrofuryl, tricyclo[5.2.1.0$^{2,6}$]decyl, tetracyclo[4.4.0.1$^{2,5}$.1$^{7,10}$]dodecyl, and 3-oxo-1-cyclohexyl. Suitable tertiary alkyl groups having such alkyl substituents include t-butyl, t-pentyl, 1-ethyl-1-methylpropyl, 1,1-diethylpropyl, 1,1,2-trimethylpropyl, 1-adamantyl-1-methylethyl, 1-methyl-1-(2-norbornyl)ethyl, 1-methyl-1-(tetrahydrofuran-2-yl)ethyl, 1-methyl-1-(7-oxanorbornan-2-yl)ethyl, 1-methylcyclopentyl, 1-ethylcyclopentyl, 1-propylcyclopentyl, 1-cyclopentylcyclopentyl, 1-cyclohexylcyclopentyl, 1-(2-tetrahydrofuryl)cyclopentyl, 1-(7-oxanorbornan-2-yl)cyclopentyl, 1-methylcyclohexyl, 1-ethylcyclohexyl, 1-cyclopentylcyclohexyl, 1-cyclohexylcyclohexyl, 2-methyl-2-norbornyl, 2-ethyl-2-norbornyl, 8-methyl-8-tricyclo[5.2.1.0$^{2,6}$]decyl, 8-ethyl-8-tricyclo[5.2.1.0$^{2,6}$]decyl, 3-methyl-3-tetracyclo[4.4.0.1$^{2,5}$.1$^{7,10}$]dodecyl, 3-ethyl-3-tetracyclo[4.4.0.1$^{2,5}$.1$^{7,10}$]dodecyl, 2-methyl-2-adamantyl, 2-ethyl-2-adamantyl, 1-methyl-3-oxo-1-cyclohexyl, 1-methyl-1-(tetrahydrofuran-2-yl)ethyl, 5-hydroxy-2-methyl-2-adamantyl, and 5-hydroxy-2-ethyl-2-adamantyl.

Also, an acetal group of the formula (B2-1) is often used as the acid labile group. It is a good choice of the acid labile group that ensures to form a pattern having a substantially rectangular pattern-substrate interface in a consistent manner.

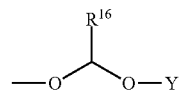

Herein $R^{16}$ is hydrogen or a straight, branched or cyclic $C_1$-$C_{10}$ alkyl group, and Y is a straight, branched or cyclic $C_1$-$C_{30}$ alkyl group.

In formula (B2-1), $R^{16}$ is hydrogen or a straight, branched or cyclic $C_1$-$C_{10}$ alkyl group. A choice of $R^{16}$ may depend on the designed sensitivity of acid labile group to acid. For example, hydrogen is selected when the acid labile group is designed to ensure relatively high stability and to be decomposed with strong acid. A straight alkyl group is selected when the acid labile group is designed to have relatively high reactivity and high sensitivity to pH changes. Although the choice varies with a particular combination of acid generator and basic compound in the resist composition, $R^{16}$ is preferably a group in which the carbon in bond with acetal carbon is secondary, when the acid labile group is designed to have a relatively large alkyl group substituted at the end and a substantial change of solubility by decomposition. Examples of $R^{16}$ bonded to acetal carbon via secondary carbon include isopropyl, sec-butyl, cyclopentyl, and cyclohexyl.

Of the acetal groups, an acetal group containing a $C_7$-$C_{30}$ polycyclic alkyl group (Y) is preferred for higher resolution. When Y is a polycyclic alkyl group, a bond is preferably formed between secondary carbon on the polycyclic structure and acetal oxygen. The acetal oxygen bonded to secondary carbon on the cyclic structure, as compared with the acetal oxygen bonded to tertiary carbon, ensures that a corresponding polymer becomes a stable compound, suggesting that the resist composition has better shelf stability and is not degraded in resolution. Said acetal oxygen, as compared with Y bonded to primary carbon via straight alkyl of at least one carbon atom, ensures that a corresponding polymer has a higher glass transition temperature (Tg), suggesting that a resist pattern after development is not deformed by bake.

Examples of the acetal group having formula (B2-1) are given below.

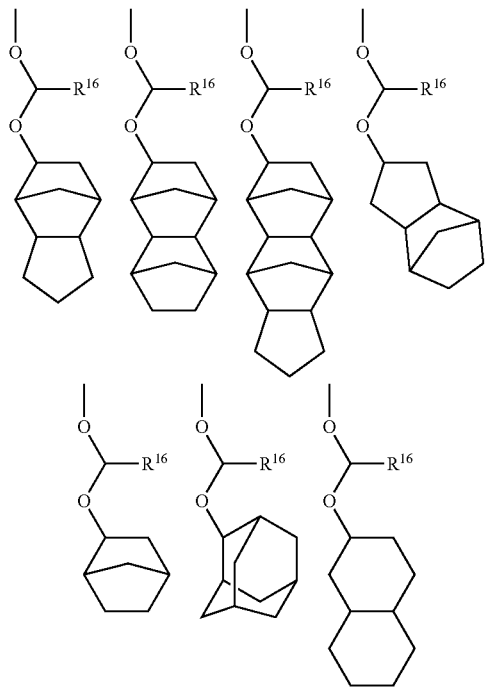

Herein $R^{16}$ is as defined above.

Another choice of acid labile group is to bond (—CH$_2$COO-tertiary alkyl) to a phenolic hydroxyl group. The tertiary alkyl group used herein may be the same as the aforementioned tertiary alkyl groups used for the protection of phenolic hydroxyl group.

The recurring units (B2) may be of one type or a mixture of two or more types. In the polymer, the recurring units (B2) are preferably incorporated in a range of 5 to 45 mol % based on the overall recurring units.

In a preferred embodiment, the polymer further comprises recurring units of at least one type selected from units of the formulae (B3), (B4) and (B5). These recurring units are simply referred to as recurring units (B3), (B4) and (B5), respectively.

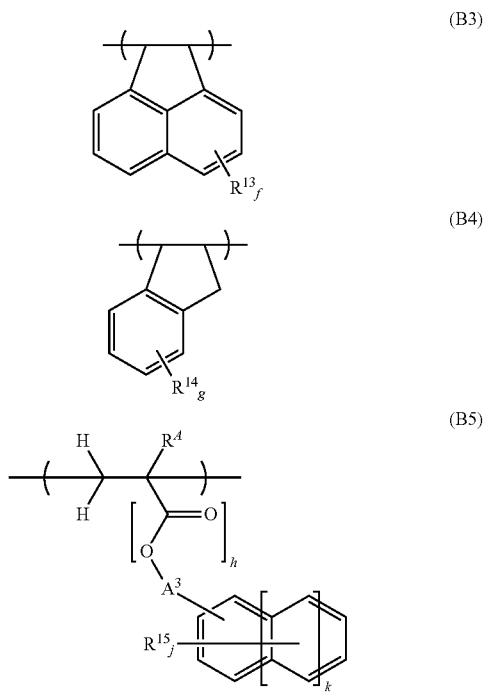

Herein $R^4$ is as defined above. $R^{13}$ and $R^{14}$ are each independently a hydroxyl group, halogen atom, acetoxy group, optionally halogenated $C_2$-$C_8$ straight, branched or cyclic acyloxy group, optionally halogenated $C_1$-$C_8$ straight, branched or cyclic alkyl group, optionally halogenated $C_1$-$C_8$ straight, branched or cyclic alkoxy group, or optionally halogenated $C_2$-$C_8$ straight, branched or cyclic alkylcarbonyloxy group. $R^{15}$ is an acetyl group, acetoxy group, $C_1$-$C_{20}$ straight, branched or cyclic alkyl group, $C_1$-$C_{20}$ straight, branched or cyclic alkoxy group, $C_2$-$C_{20}$ straight, branched or cyclic acyloxy group, $C_2$-$C_{20}$ straight, branched or cyclic alkoxyalkyl group, $C_2$-$C_{20}$ alkylthioalkyl group, halogen atom, nitro group, cyano group, sulfinyl group, or sulfonyl group. A is a single bond or $C_1$-$C_{10}$ straight, branched or cyclic alkylene group in which an ether bond may intervene in a carbon-carbon bond, f and g are each independently an integer of 0 to 4, h is 0 or 1, j is an integer of 0 to 5, and k is an integer of 0 to 2.

When recurring units of at least one type selected from recurring units (B3) to (B5) are incorporated, better performance is obtained because not only the aromatic ring possesses etching resistance, but the cyclic structure incorporated into the main chain also exerts the effect of improving resistance to EB irradiation during etching and pattern inspection steps.

The recurring units (B3) to (B5) may be of one type or a combination of plural types. In order to exert an effect of improving etching resistance, the units (B3) to (B5) are preferably incorporated in a range of at least 5 mol % based on the overall recurring units of the polymer. The units (B3)

to (B5) are also preferably incorporated in a range of up to 35 mol %, more preferably up to 30 mol % based on the overall recurring units of the polymer. Where the units (B3) to (B5) are free of a functional group or have a functional group other than the aforementioned ones, the formation of development defects is avoided as long as the amount of these units incorporated is up to 35 mol %.

The preferred polymer contains recurring units (B1), recurring units (B2), and recurring units of at least one type selected from recurring units (B3) to (B5) as its constituents because both etch resistance and resolution are improved. These recurring units are preferably incorporated in an amount of at least 60 mol %, more preferably at least 70 mol %, even more preferably at least 80 mol %, based on the overall recurring units of the polymer.

The polymer may further contain (meth)acrylate units protected with an acid labile group, and/or (meth)acrylate units having an adhesive group such as lactone structure or hydroxyl group other than phenolic hydroxyl group. These units may be incorporated for fine adjustment of properties of a resist film, though they are optional. When incorporated, these recurring units are used in an amount of preferably 0 to 30 mol %, more preferably 0 to 20 mol %. Examples of the (meth)acrylate units having such an adhesive group include units having the formulae (b1) to (b3):

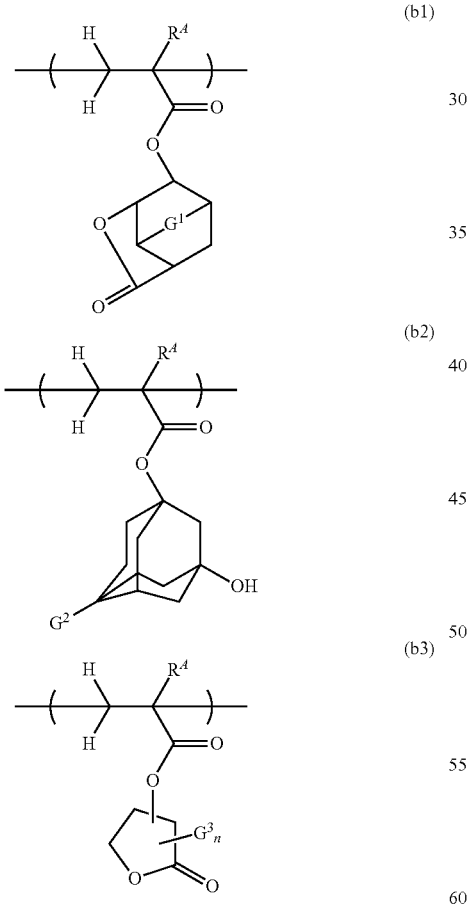

wherein $R^A$ is as defined above, $G^1$ is —O— or methylene, $G^2$ is hydrogen or hydroxyl, $G^3$ is a $C_1$-$C_4$ straight, branched or cyclic alkyl group, and n is an integer of 0 to 3. These units do not exhibit acidity and may be used as supplemental units for imparting adhesion to substrates or for adjusting solubility.

The polymer may further comprise recurring units of at least one type selected from recurring units having formula (B6), recurring units having formula (B7), recurring units having formula (B8), and recurring units having formula (B9). Notably these recurring units are simply referred to as recurring units (B6), (B7), (B8) and (B9), respectively. Incorporation of any of these units is effective for suppressing acid diffusion, improving resolution, and forming a pattern with reduced LER.

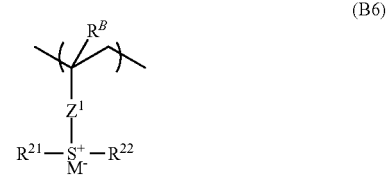

(B6)

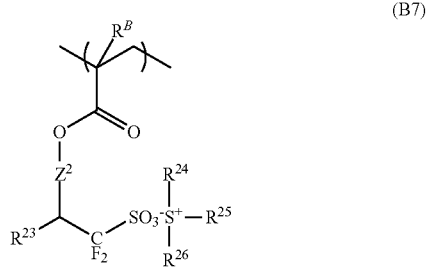

(B7)

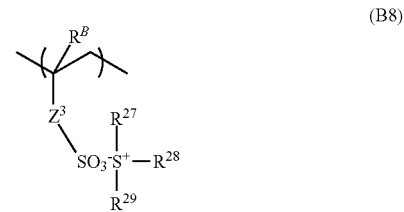

(B8)

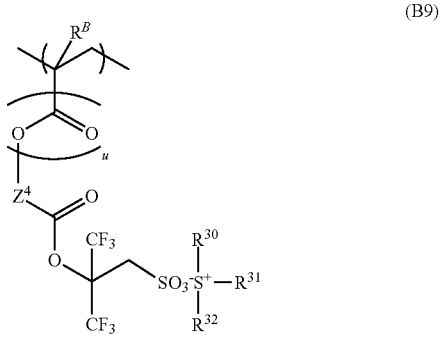

(B9)

Herein $R^B$ is each independently hydrogen or methyl. $Z^1$ is a single bond, phenylene group, —O—$Z^{12}$—, or —C(=O)—$Z^{11}$—$Z^{12}$—, wherein $Z^{11}$ is —O— or —NH—, $Z^{12}$ is a C1-C6 straight, branched or cyclic alkylene, $C_2$-$C_6$ straight, branched or cyclic alkenylene or phenylene group, which may contain a carbonyl, ester, ether or hydroxy moiety. $Z^2$ is a single bond or —$Z^{21}$—C(=O)—O—, wherein $Z^{21}$ is a $C_1$-$C_{20}$ straight, branched or cyclic divalent hydrocarbon group which may contain a heteroatom-containing moiety. $Z^3$ is a single bond, methylene, ethylene, phenylene, fluorinated phenylene, —O—$Z^{32}$—, or —C(O)—$Z^{31}$—$Z^{32}$—, wherein $Z^{31}$ is —O— or —NH—, $Z^{32}$ is a $C_1$-$C_6$ straight, branched or cyclic alkylene, $C_2$-$C_6$ straight, branched or cyclic alkenylene or phenylene group, which may contain a carbonyl, ester, ether or hydroxy moiety. $Z^4$ is a single bond or a $C_1$-$C_{30}$ straight, branched or cyclic divalent hydrocarbon group which may contain a heteroatom, u is 0 or 1, with the proviso that u is 0 when $Z^4$ is a single bond, $R^{21}$, $R^{22}$, $R^{24}$, $R^{25}$, $R^{26}$, $R^{27}$, $R^{28}$, $R^{29}$, $R^{30}$, $R^{31}$, and $R^{32}$ are each independently a $C_1$-$C_{20}$ straight, branched or cyclic monovalent hydrocarbon group in which at least one hydrogen atom may be replaced by a moiety containing a heteroatom such as oxygen, sulfur, nitrogen or halogen, or in which at least one carbon atom may be replaced by a moiety containing a heteroatom such as oxygen, sulfur or nitrogen, so that the group may contain a hydroxy, cyano, carbonyl, ether bond, ester bond, sulfonic acid ester bond, carbonate bond, lactone ring, sultone ring, carboxylic anhydride, or haloalkyl moiety. $R^{21}$ and $R^{22}$ may bond together to form a ring with the sulfur atom to which they are attached, any two of $R^{24}$, $R^{25}$ and $R^{26}$, any two of RV, $R^{27}$, $R^{28}$ and $R^{29}$, or any two of $R^{30}$, $R^{31}$ and $R^{32}$ may bond together to form a ring with the sulfur atom to which they are attached. $R^{23}$ is hydrogen or trifluoromethyl. $M^-$ is a non-nucleophilic counter ion.

In formula (B7) wherein $Z^2$ is —$Z^{21}$—C(=O)—O—, $Z^{21}$ is a divalent hydrocarbon group which may contain a heteroatom-containing moiety. Illustrative, non-limiting examples of the hydrocarbon group $Z^{21}$ are given below.

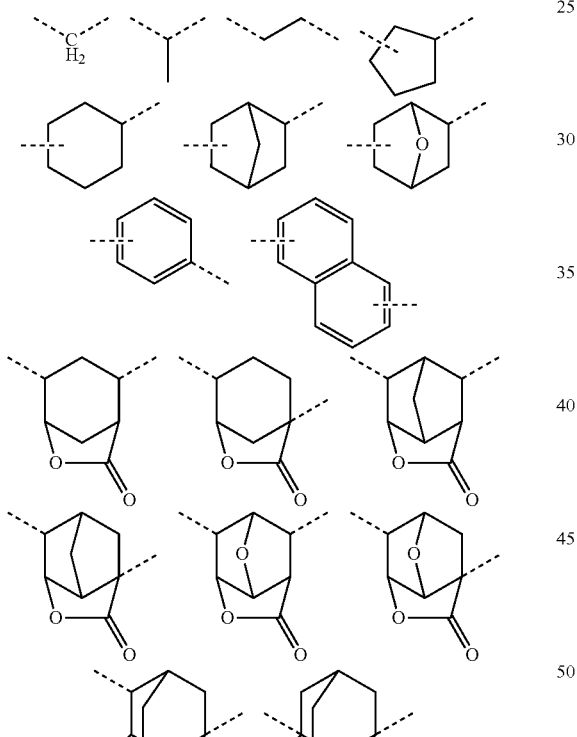

In the recurring units (B6), examples of the non-nucleophilic counter ion M include those described in JP-A 2010-113209 and JP-A 2007-145797. Examples of the recurring units (B7) wherein $R^2$ is hydrogen include those described in JP-A 2010-116550. Examples of the recurring units (B7) wherein $R^{23}$ is trifluoromethyl include those described in JP-A 2010-077404. Examples of the recurring units (B8) include those described in JP-A 2012-246265 and JP-A 2012-246426.

Preferred examples of the anion moiety in the monomer from which the recurring units (B9) are derived are shown below, but not limited thereto.

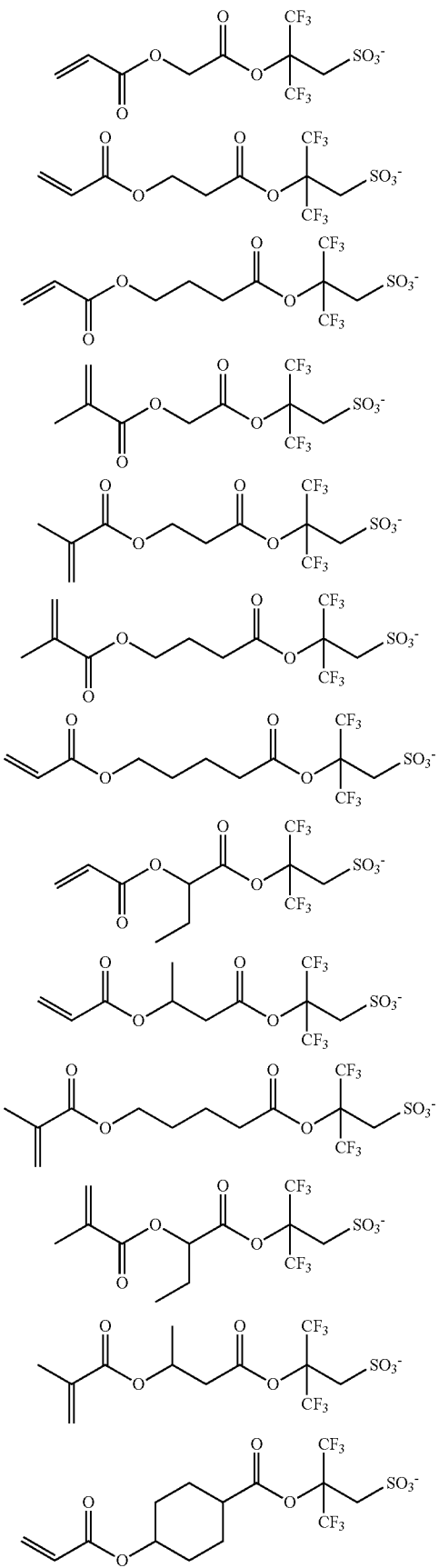

-continued
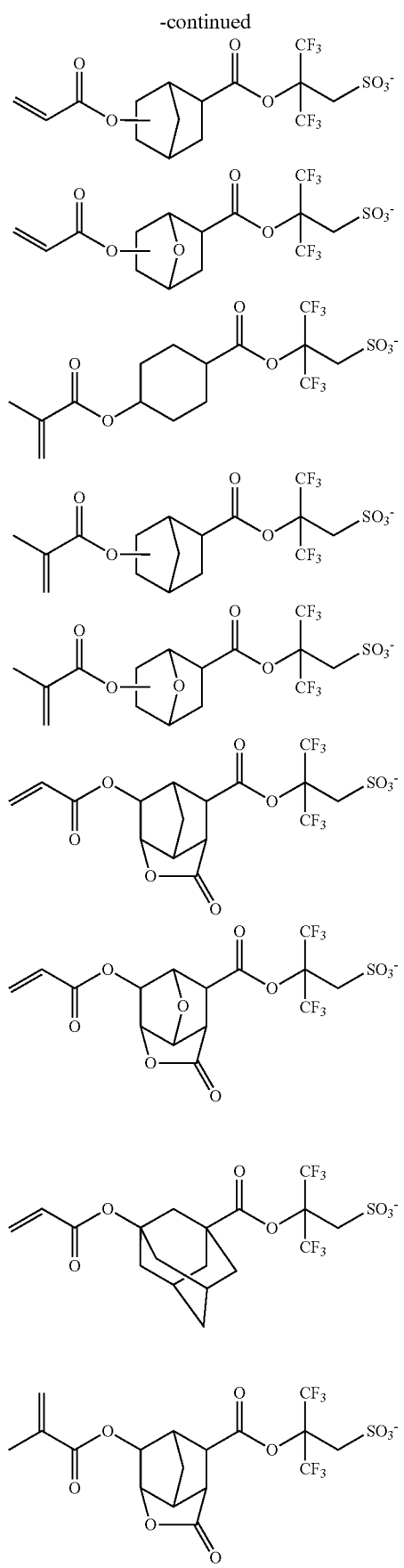
-continued
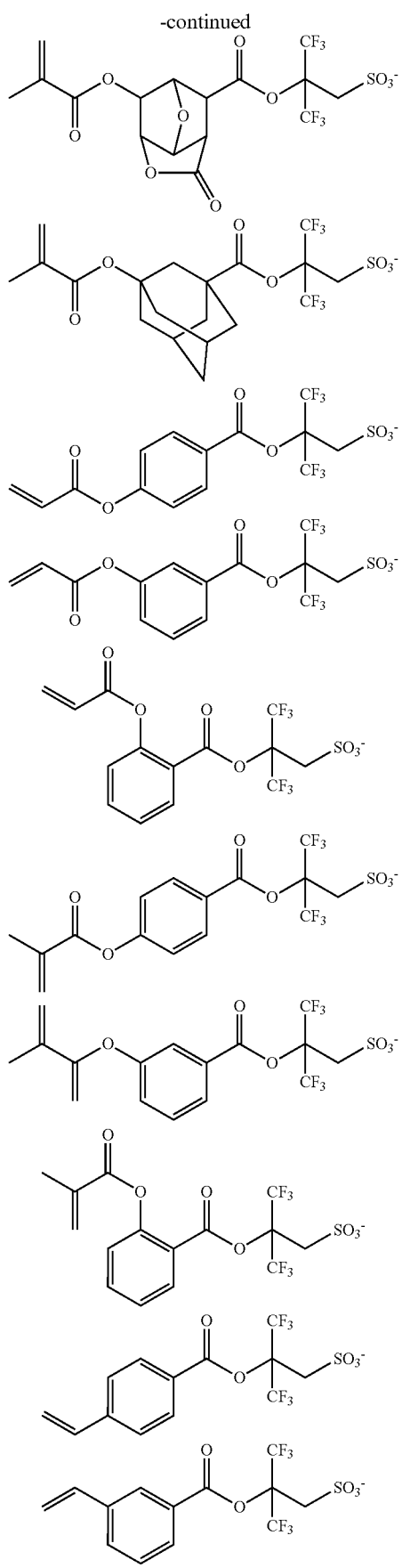

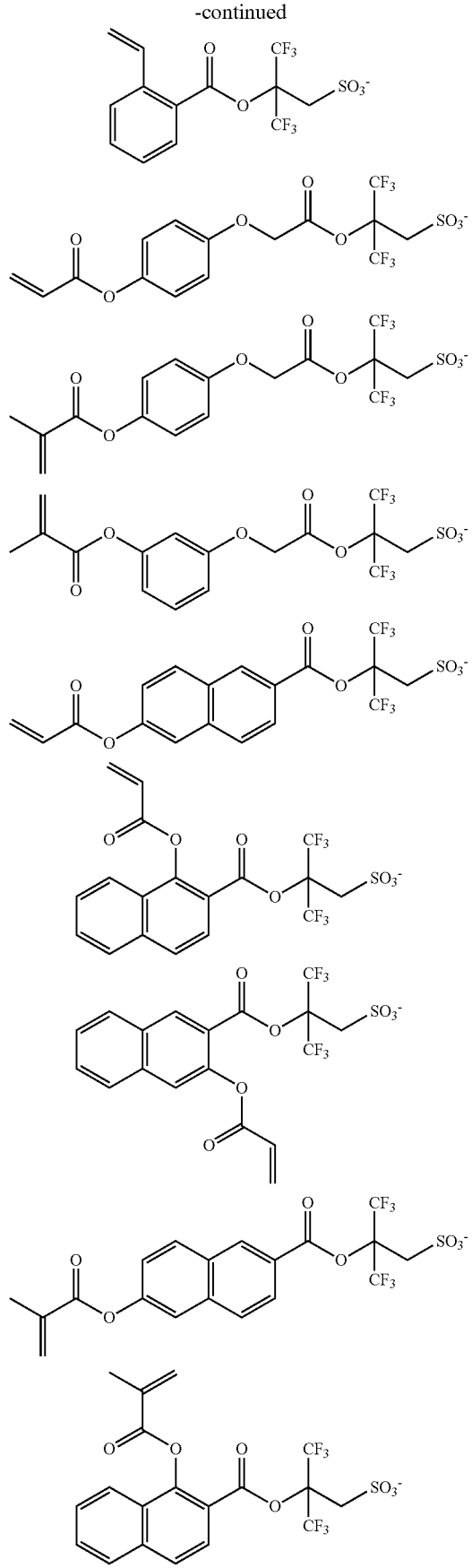
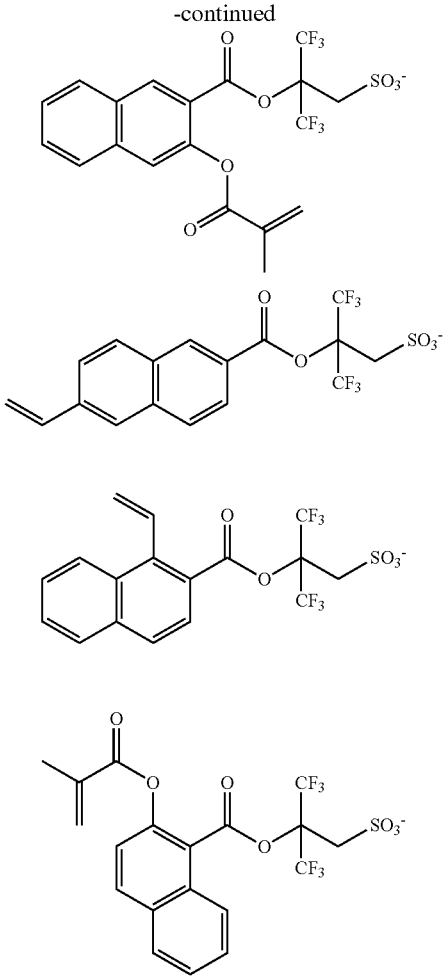
Examples of the sulfonium cation in formulae (B7) to (B9) wherein any two of $R^{24}$, $R^{25}$ and $R^{26}$, any two of $R^{27}$, $R^{28}$ and $R^{29}$, or any two of $R^{30}$, $R^{31}$ and $R^{32}$ bond together to form a ring with the sulfur atom to which they are attached, are shown below.
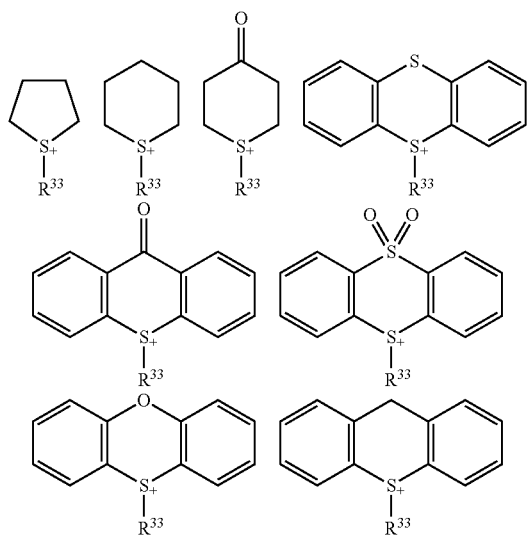

-continued
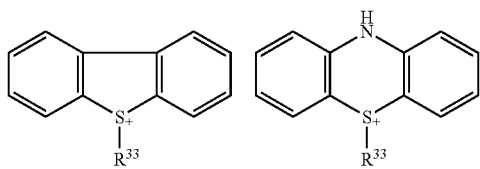
It is noted that $R^{33}$ is the same as defined and exemplified for $R^{21}$ to $R^{32}$.
Specific examples of the sulfonium cation in formulae (B7) to (B9) are shown below, but not limited thereto.
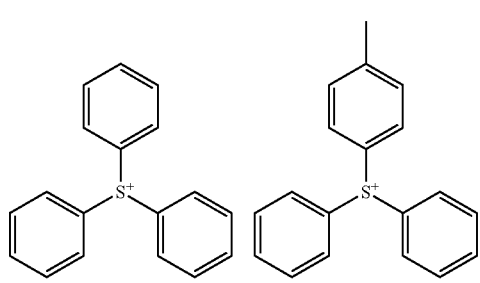
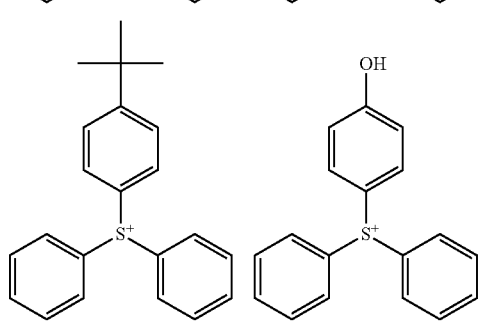
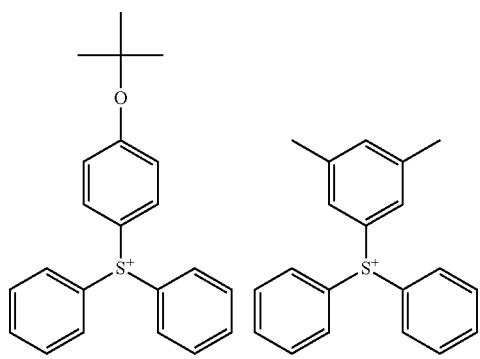
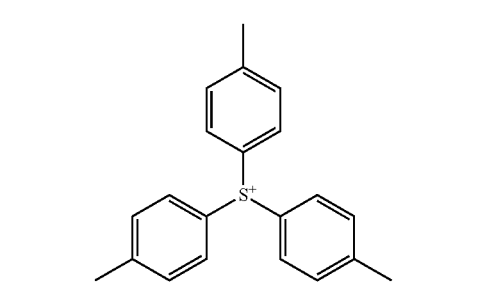
-continued
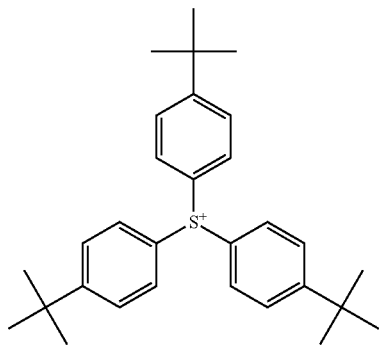
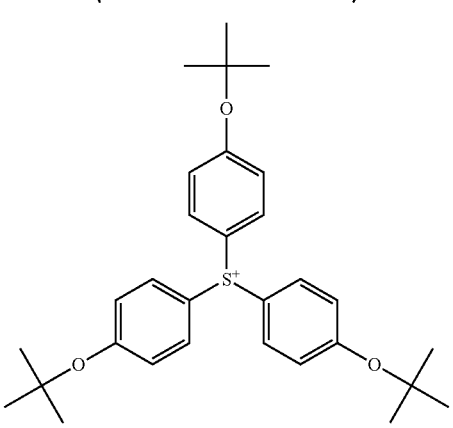
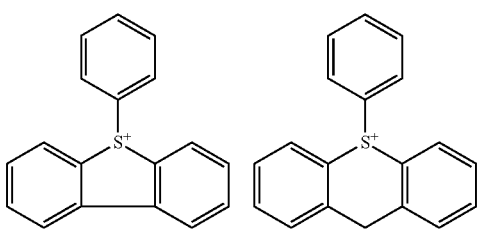
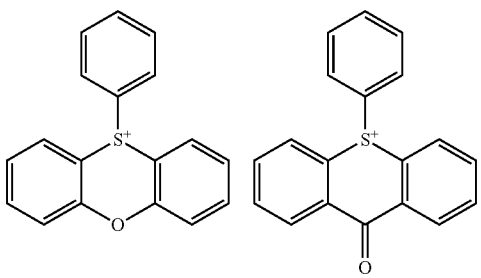
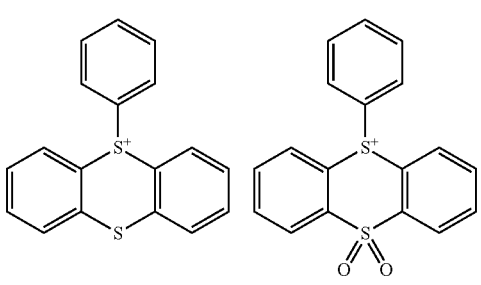

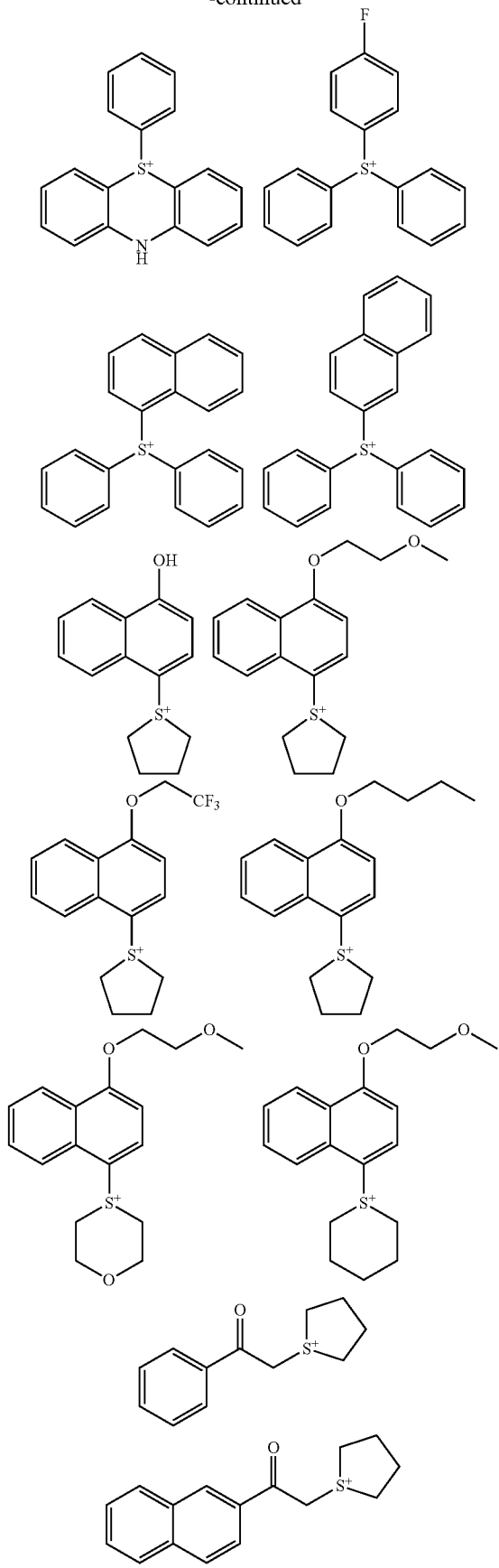

The recurring units (B6) to (19) are units capable of generating an acid upon receipt of high-energy radiation. With the relevant units bound into a polymer, an appropriate control of acid diffusion becomes possible, and a pattern with minimal LER can be formed. Since the acid-generating unit is bound to a polymer, the phenomenon that acid volatilizes from the exposed region and re-deposits on the unexposed region during bake in vacuum is suppressed. This is effective for reducing LER and for suppressing unwanted deprotection reaction in the unexposed region for thereby reducing defects. The content of recurring units (B6) to (B9) is preferably 0.5 to 30 mol % based on the overall recurring units of the polymer.

The base polymer (B) may be a mixture of a polymer comprising recurring units (B1) and recurring units (B6) to (B9) and a polymer free of recurring units (B6) to (B9). In this embodiment, the polymer free of recurring units (B6) to (B9) is preferably used in an amount of 2 to 5,000 parts, more preferably 10 to 1,000 parts by weight per 100 parts by weight of the polymer comprising recurring units (B6) to (B9).

The polymer may be synthesized by combining suitable monomers optionally protected with a protective group, copolymerizing them in the standard way, and effecting deprotection reaction if necessary. The copolymerization reaction is preferably radical polymerization or anionic polymerization though not limited thereto. For the polymerization reaction, reference may be made to JP-A 2004-115630.

The polymer should preferably have a weight average molecular weight (Mw) of 1,000 to 50,000, and more preferably 2,000 to 20,000. A Mw of at least 1,000 eliminates the risk that pattern features are rounded at their top, inviting degradations of resolution and LER. A Mw of up to 50,000 eliminates the risk that LER is increased particularly when a pattern with a line width of up to 100 nm is formed. As used herein, Mw is measured by GPC versus polystyrene standards using tetrahydrofuran (THF) solvent.

The polymer preferably has a narrow molecular weight distribution or dispersity (Mw/Mn) of 1.0 to 2.0, more preferably 1.0 to 1.8. A polymer with such a narrow dispersity eliminates any foreign particles left on the pattern or profile degradation of the pattern after development.

(C) Fluorinated Polymer

The resist composition may further comprise (C) a fluorinated polymer comprising recurring units having the formula (C1) and recurring units of at least one type selected from recurring units having the formulae (C2), (C3), (C4), and (C5), for the purposes of enhancing contrast, preventing chemical flare of acid upon exposure to high-energy radiation, preventing mixing of acid from an anti-charging film in the step of coating an anti-charging film-forming material on a resist film, and suppressing unexpected unnecessary pattern degradation. Notably, recurring units having formulae (C1), (C2), (C3), (C4), and (C5) are simply referred to as recurring units (C1), (C2), (C3), (C4), and (C5), respectively. Since the fluorinated polymer also has a surface active function, it can prevent insoluble residues from redepositing onto the substrate during the development step and is thus effective for preventing development defects.

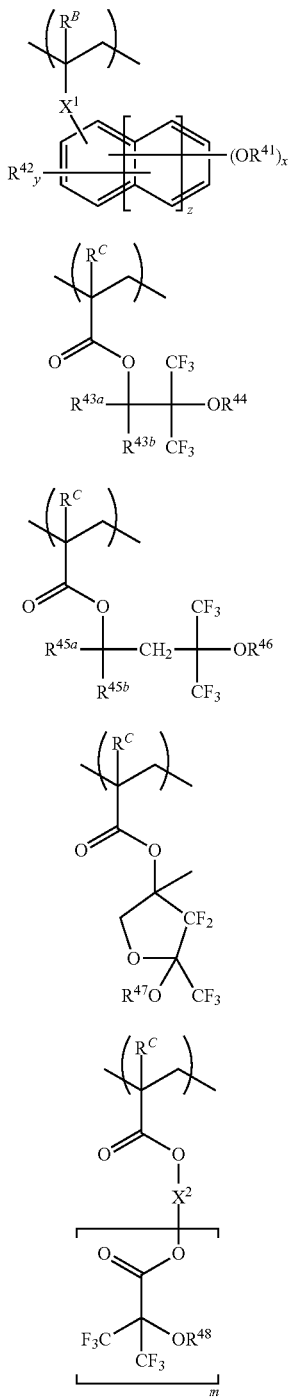

(C1)
(C2)
(C3)
(C4)
(C5)

Herein $R^B$ is each independently hydrogen or methyl. $R^C$ is each independently hydrogen, fluorine, methyl or trifluoromethyl. $R^{41}$ is hydrogen or a $C_1$-$C_5$ straight or branched monovalent hydrocarbon group in which a heteroatom may intervene in a carbon-carbon bond. $R^{42}$ is a $C_1$-$C_5$ straight or branched monovalent hydrocarbon group in which a heteroatom may intervene in a carbon-carbon bond. $R^{43a}$, $R^{43b}$, $R^{45a}$ and $R^{45b}$ are each independently hydrogen or a $C_1$-$C_{10}$ straight, branched or cyclic alkyl group. $R^{44}$, $R^{46}$, $R^{47}$ and $R^{48}$ are each independently hydrogen, a $C_1$-$C_{15}$ straight, branched or cyclic monovalent hydrocarbon group or monovalent fluorinated hydrocarbon group, or an acid labile group, with the proviso that an ether or carbonyl moiety may intervene in a carbon-carbon bond in the monovalent hydrocarbon groups or monovalent fluorinated hydrocarbon groups represented by $R^{44}$, $R^{46}$, $R^{47}$ and $R^{48}$. The subscript x is an integer of 1 to 3, y is an integer satisfying: $0 \leq y \leq 5+2z-x$, z is 0 or 1, m is an integer of 1 to 3. $X^1$ is a single bond, —C(=O)—O— or —C(=O)—NH—. $X^2$ is a $C_1$-$C_{20}$ straight, branched or cyclic (m+1)-valent hydrocarbon group or fluorinated hydrocarbon group.

Suitable monovalent hydrocarbon groups include alkyl, alkenyl and alkynyl groups, with the alkyl groups being preferred. Suitable alkyl groups include methyl, ethyl, n-propyl, isopropyl, n-butyl, isobutyl, sec-butyl, and n-pentyl. In these groups, a moiety containing a heteroatom such as oxygen, sulfur or nitrogen may intervene in a carbon-carbon bond.

In formula (C1), —$OR^{41}$ is preferably a hydrophilic group. In this case, $R^{41}$ is preferably hydrogen or a $C_1$-$C_5$ alkyl group in which oxygen (ether bond) intervenes in a carbon-carbon bond.

Examples of the recurring unit (C1) are given below, but not limited thereto. Herein $R^B$ is as defined above.

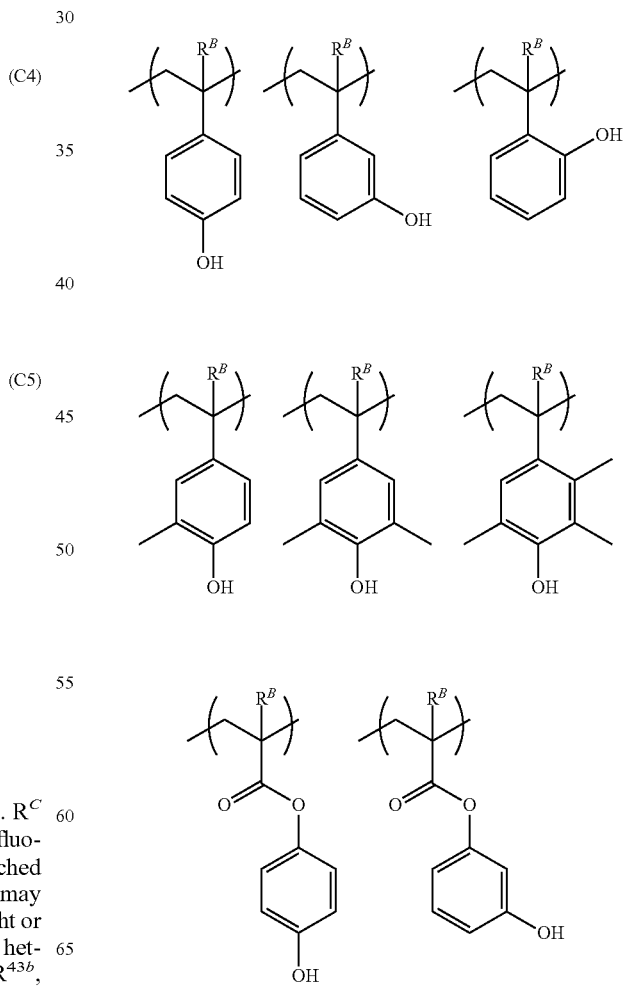

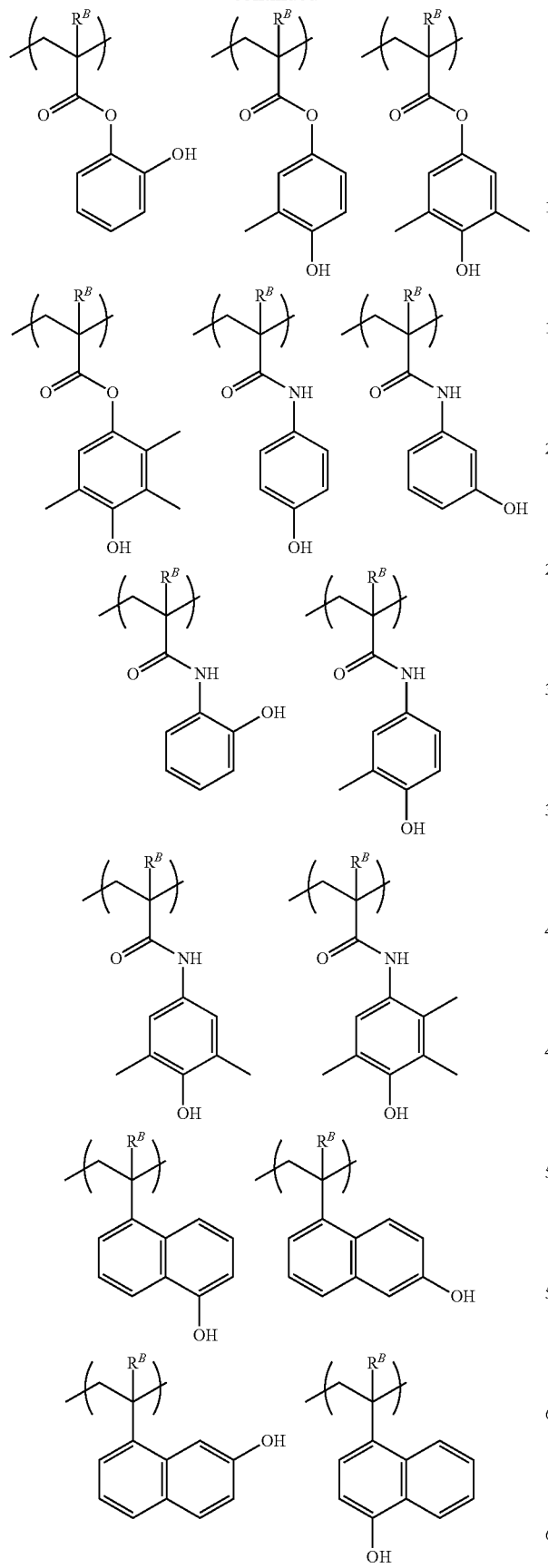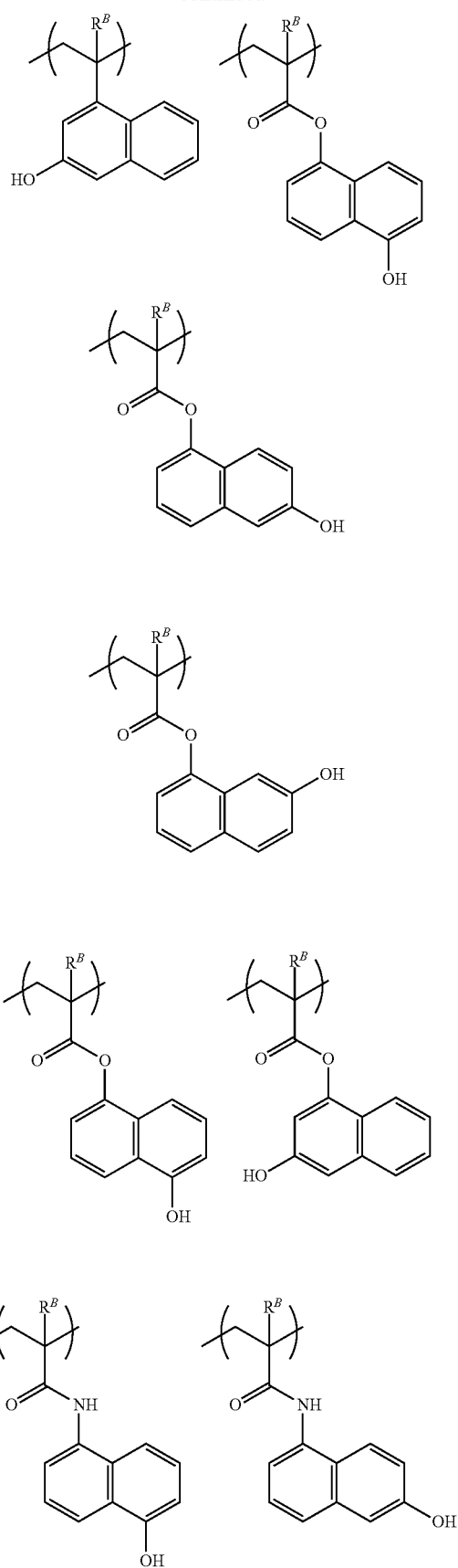

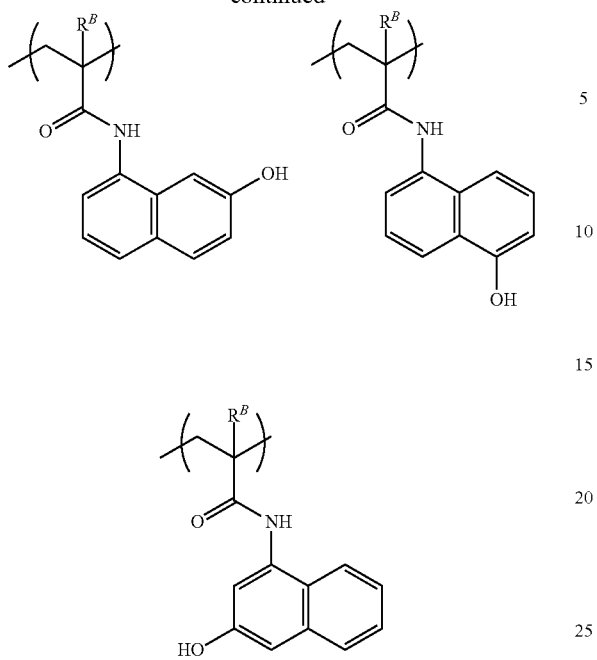

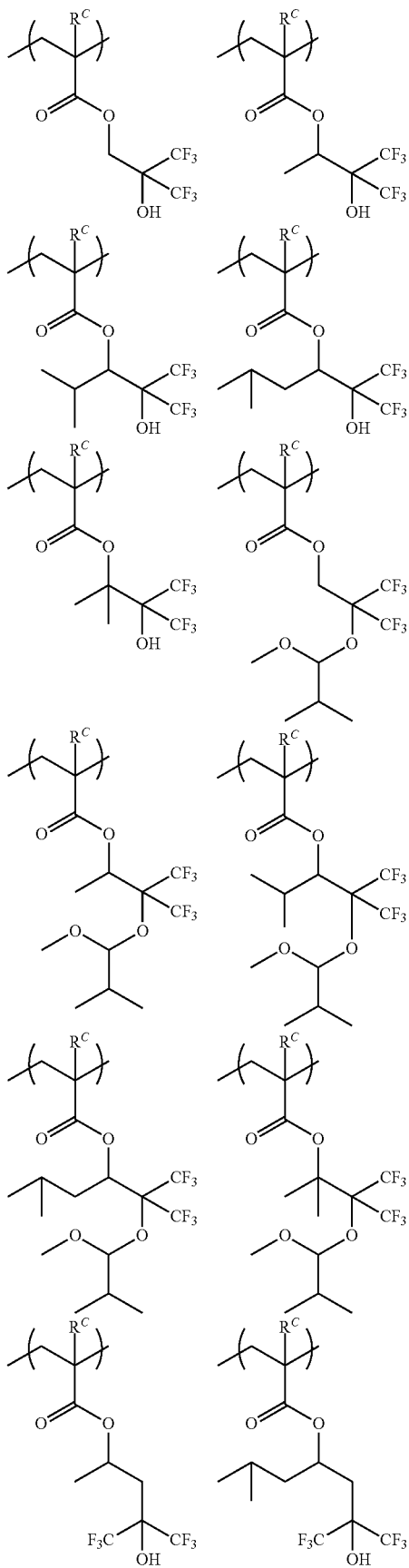

In formula (C1), $X^1$ is preferably —C(=O)—O— or —C(=O)—NH—. Also preferably $R^B$ is methyl. The inclusion of carbonyl in $X^1$ enhances the ability to trap the acid originating from the anti-charging film. A polymer wherein $R^B$ is methyl is a rigid polymer having a high glass transition temperature (Tg) which is effective for suppressing acid diffusion. As a result, the stability with time of a resist film is improved, and neither resolution nor pattern profile is degraded.

In formulae (C2) and (C3), examples of the alkyl group represented by $R^{43a}$, $R^{43b}$, $R^{45a}$ and $R^{45b}$ include methyl, ethyl, n-propyl, isopropyl, cyclopropyl, n-butyl, isobutyl, sec-butyl, tert-butyl, cyclobutyl, n-pentyl, cyclopentyl, n-hexyl, cyclohexyl, n-heptyl, n-octyl, n-nonyl, n-decyl, adamantyl, and norbornyl. Inter alia, $C_1$-$C_6$ straight, branched or cyclic alkyl groups are preferred.

In formulae (C2) to (C5), examples of the monovalent hydrocarbon group represented by $R^{44}$, $R^{46}$, $R^{47}$ and $R^{48}$ include alkyl, alkenyl and alkynyl groups, with the alkyl groups being preferred. Suitable alkyl groups include n-undecyl, n-dodecyl, tridecyl, tetradecyl and pentadecyl as well as those exemplified above. The monovalent fluorinated hydrocarbon groups correspond to the foregoing monovalent hydrocarbon groups in which one or more or even all carbon-bonded hydrogen atoms are substituted by fluorine atoms.

Examples of the $C_1$-$C_{20}$ straight, branched or cyclic (m+1)-valent hydrocarbon group or fluorinated hydrocarbon group include the foregoing monovalent hydrocarbon groups and monovalent fluorinated hydrocarbon groups, with a number (m) of hydrogen atoms being eliminated.

Examples of the recurring units (C2) to (C5) are given below, but not limited thereto. Herein $R^C$ is as defined above.

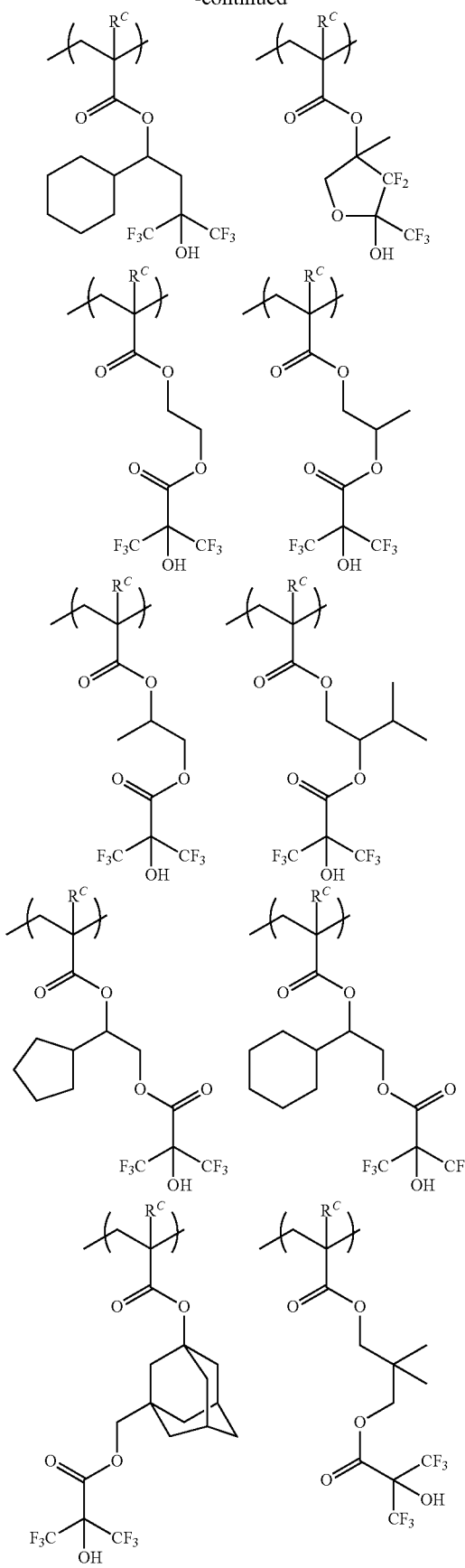
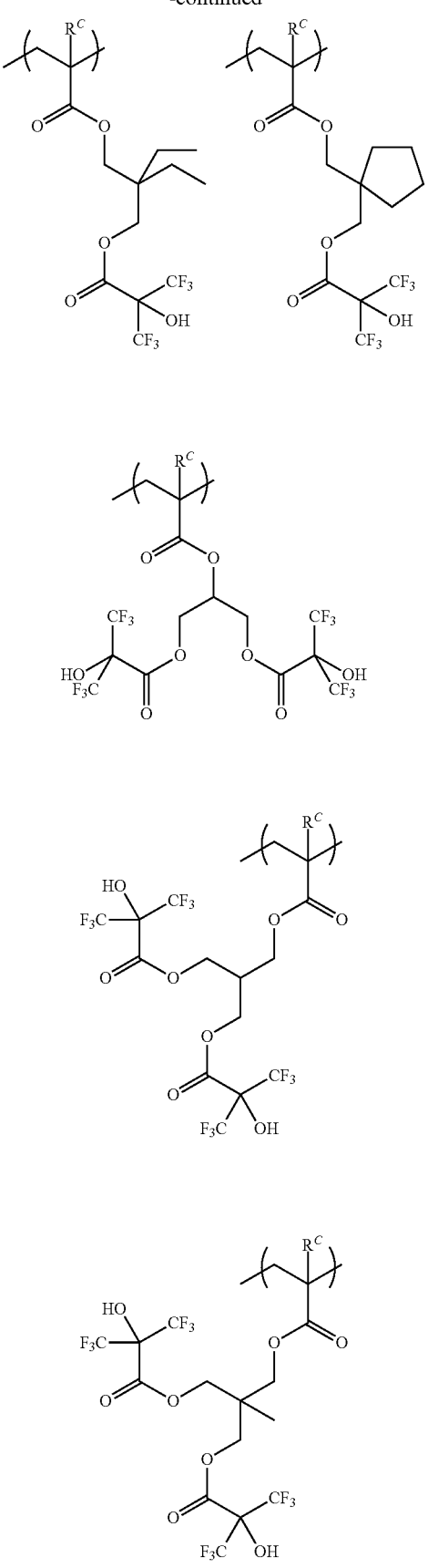

-continued

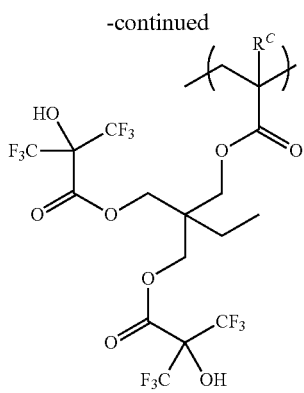

The recurring unit (C1) is preferably incorporated in an amount of 5 to 85 mol %, more preferably 15 to 80 mol % based on the overall recurring units of the fluorinated polymer (C). The recurring units (D2) to (C5), which may be used alone or in admixture, are preferably incorporated in an amount of 15 to 95 mol %, more preferably 20 to 85 mol % based on the overall recurring units of the fluorinated polymer (C).

The fluorinated polymer (C) may comprise additional recurring units as well as the recurring units (C1) to (C5). Suitable additional recurring units include those described in U.S. Pat. No. 9,091,918 (JP-A 2014-177407, paragraphs [0046]-[0078]). When the fluorinated polymer (C) comprises additional recurring units, their content is preferably up to 50 mol % based on the overall recurring units.

The fluorinated polymer (C) may be synthesized by combining suitable monomers optionally protected with a protective group, copolymerizing them in the standard way, and effecting deprotection reaction if necessary. The copolymerization reaction is preferably radical polymerization or anionic polymerization though not limited thereto. For the polymerization reaction, reference may be made to JP-A 2004-115630.

The fluorinated polymer (C) should preferably have a weight average molecular weight (Mw) of 2,000 to 50,000, and more preferably 3,000 to 20,000. A fluorinated polymer with a Mw of less than 2,000 helps acid diffusion, degrading resolution and detracting from age stability. A polymer with too high Mw has a reduced solubility in solvent, leading to coating defects. The fluorinated polymer preferably has a dispersity (Mw/Mn) of 1.0 to 2.2, more preferably 1.0 to 1.7.

The fluorinated polymer (C) is preferably used in an amount of 0.01 to 30 parts, more preferably 0.1 to 20 parts by weight per 100 parts by weight of the base polymer (B).

(D) Organic Solvent

The positive resist composition may further comprise (D) an organic solvent. The organic solvent used herein is not particularly limited as long as the components are soluble therein. Examples of the organic solvent are described in JP-A 2008-111103, paragraphs [0144] to [0145] (U.S. Pat. No. 7,537,880). Specifically, exemplary solvents include ketones such as cyclohexanone and methyl-2-n-pentyl ketone; alcohols such as 3-methoxybutanol, 3-methyl-3-methoxybutanol, 1-methoxy-2-propanol, 1-ethoxy-2-propanol, and diacetone alcohol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, t-butyl acetate, t-butyl propionate, and propylene glycol mono-t-butyl ether acetate; and lactones such as γ-butyrolactone, and mixtures thereof. Where an acid labile group of acetal form is used, a high-boiling alcohol solvent such as diethylene glycol, propylene glycol, glycerol, 1,4-butanediol or 1,3-butanediol may be added for accelerating deprotection reaction of acetal. Of the above organic solvents, it is recommended to use 1-ethoxy-2-propanol, PGMEA, propylene glycol monomethyl ether, cyclohexanone, ethyl lactate, γ-butyrolactone, and mixtures thereof.

An appropriate amount of the organic solvent (D) used is 200 to 10,000 parts, more preferably 400 to 5,000 parts by weight per 100 parts by weight of the base polymer (B).

(E) Photoacid Generator

The resist composition may further comprise (E) a photoacid generator (PAG) in order that the composition function as a chemically amplified positive resist composition. The PAG may be any compound capable of generating an acid upon exposure to high-energy radiation. Suitable PAGs include sulfonium salts, iodonium salts, sulfonyl-diazomethane, N-sulfonyloxyimide, and oxime-O-sulfonate acid generators. These PAGs may be used alone or in admixture of two or more.

Suitable PAGs include nonafluorobutane sulfonate, partially fluorinated sulfonates described in JP-A 2012-189977, paragraphs [0247]-[0251], partially fluorinated sulfonates described in JP-A 2013-101271, paragraphs [0261]-[0265], and those described in JP-A 2008-111103, paragraphs [0122]-[0142] and JP-A 2010-215608, paragraphs [0080]-[0081]. Among others, arylsulfonate and alkanesulfonate type PAGs are preferred because they generate acids having an appropriate strength to deprotect the acid labile group in recurring unit (B2).

The preferred acid generators are compounds having a sulfonium anion of the structure shown below. Notably the cation that pairs with the anion is as exemplified for the sulfonium cation in formulae (B7) to (B9).

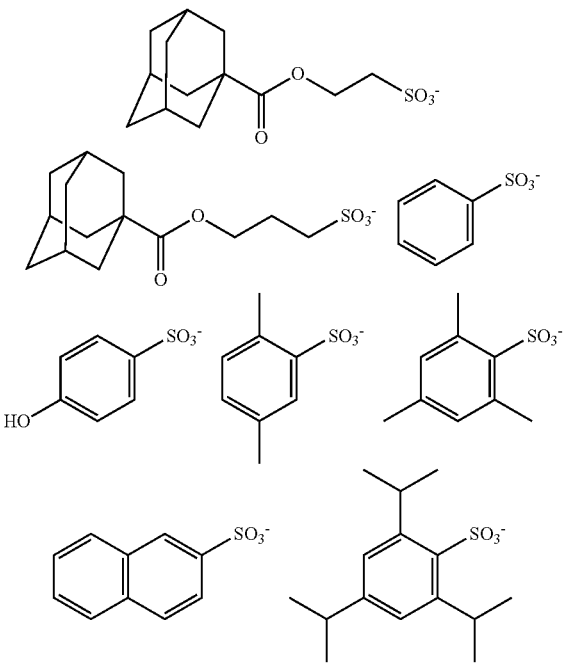

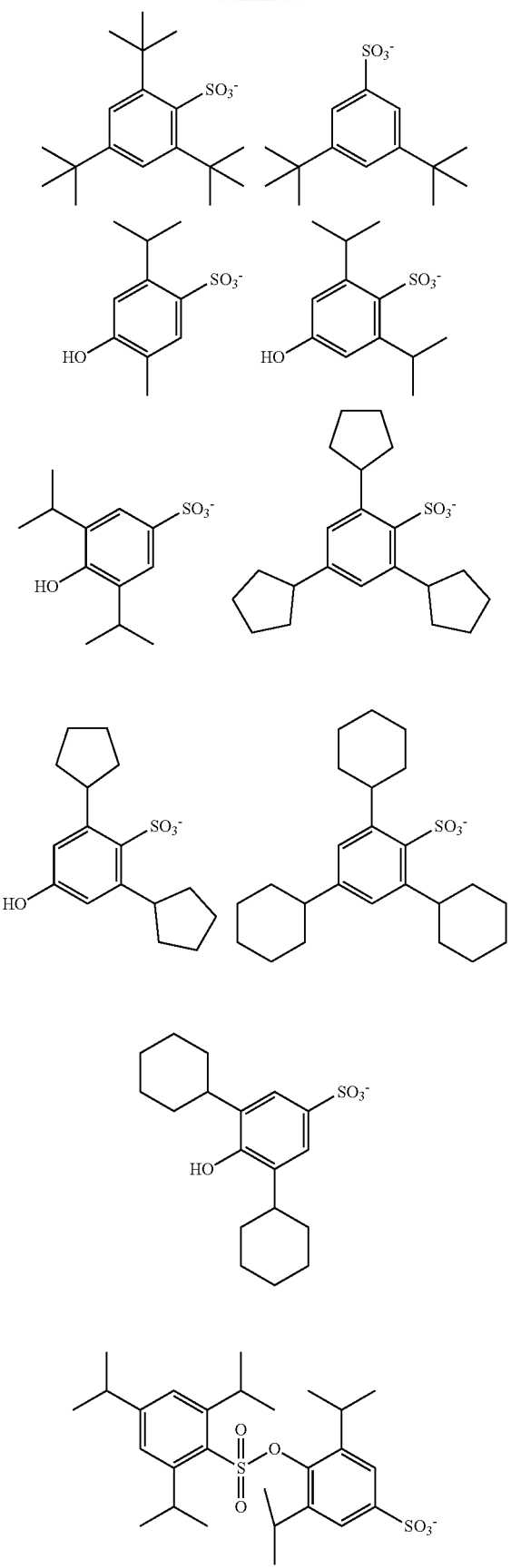
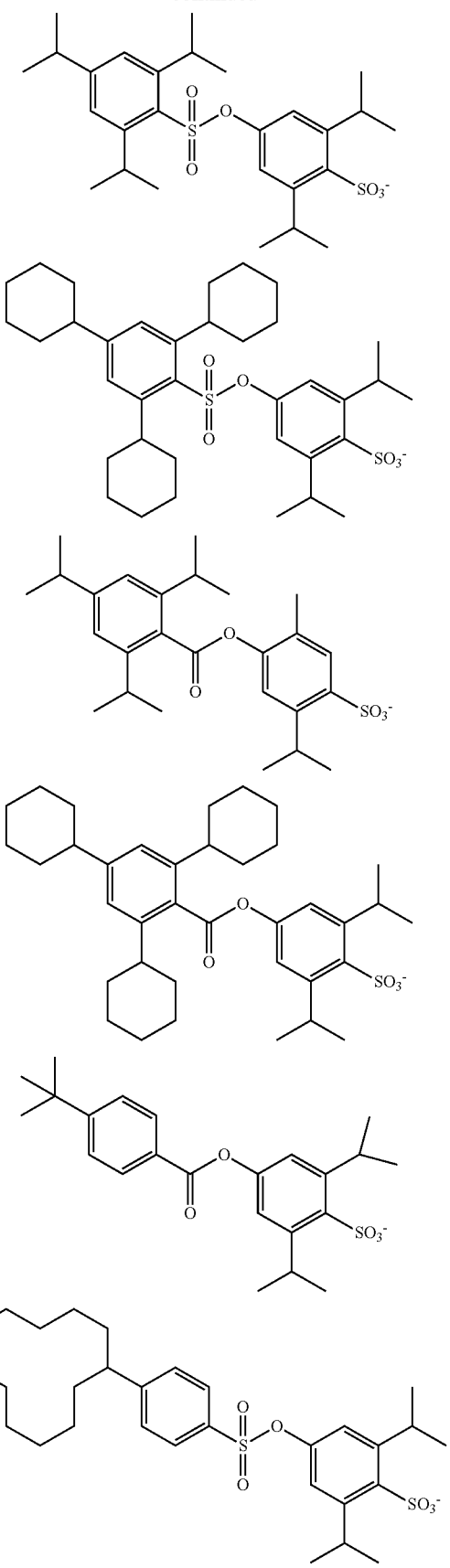

-continued
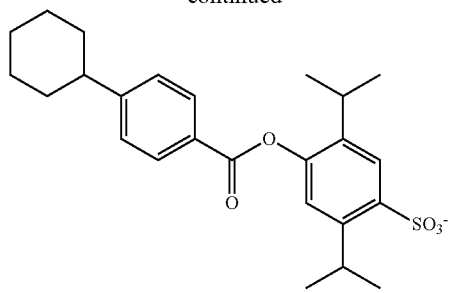
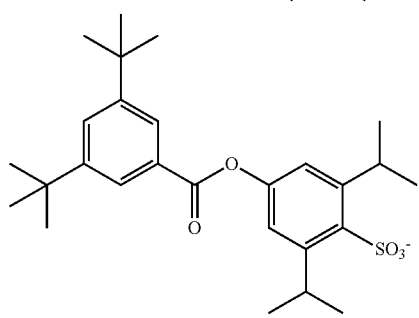
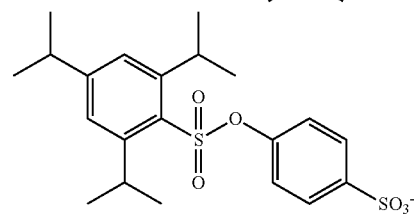
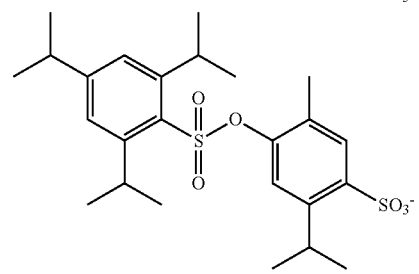
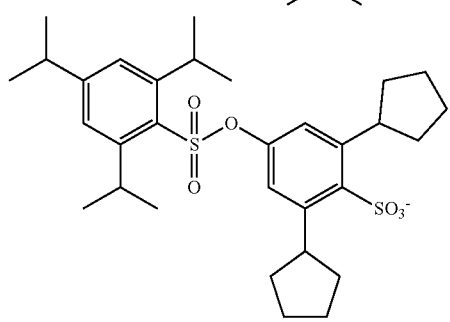
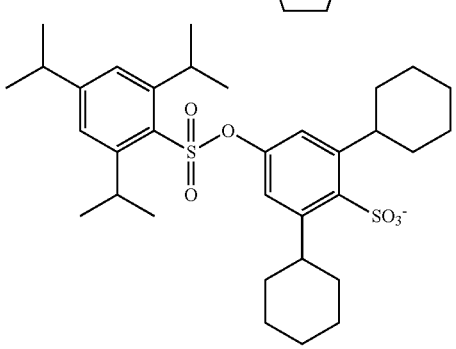
-continued
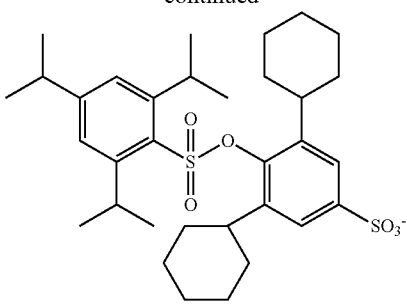
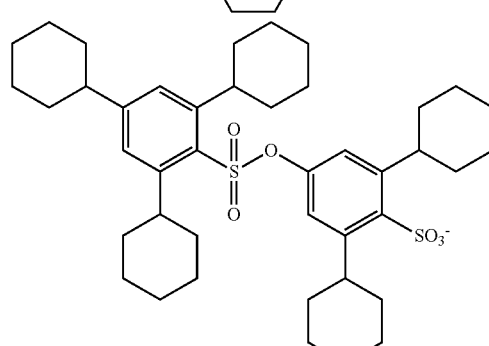
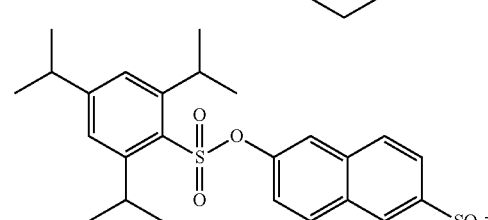
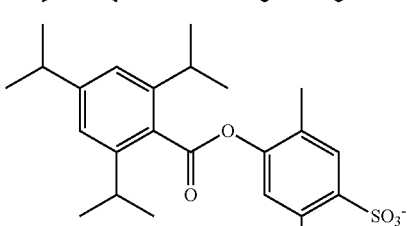
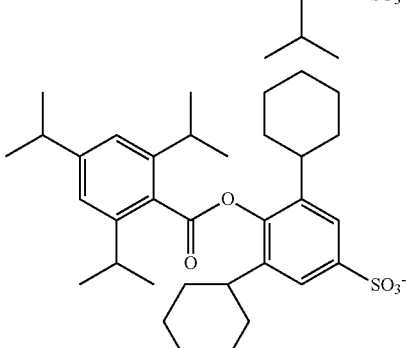
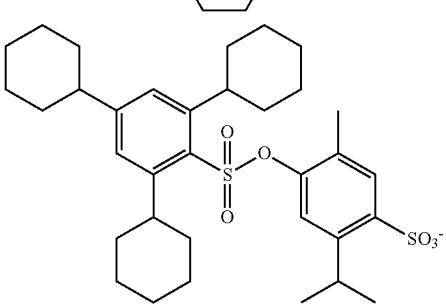

49
-continued
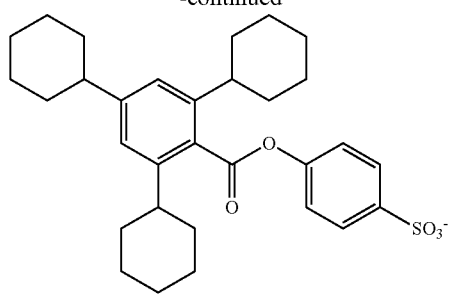
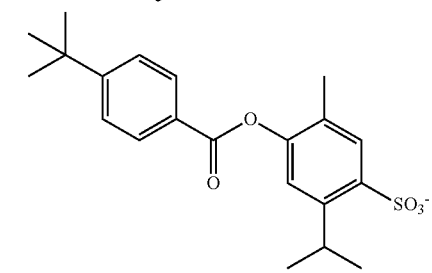
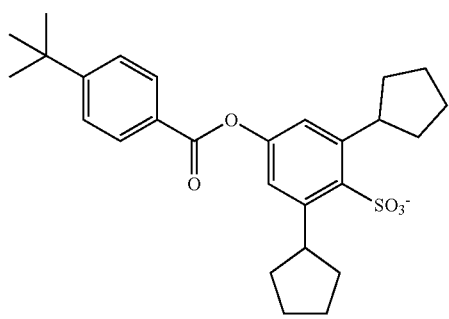
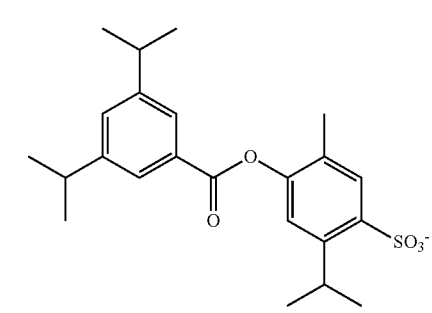
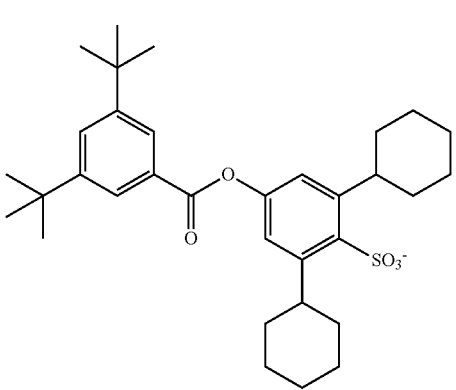
50
-continued
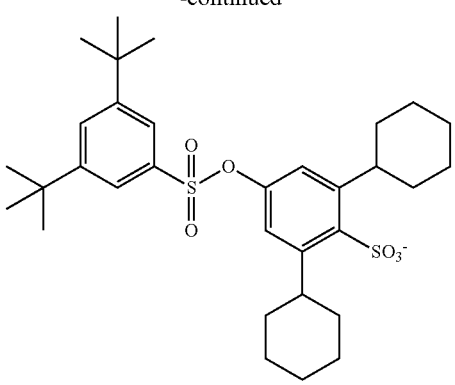
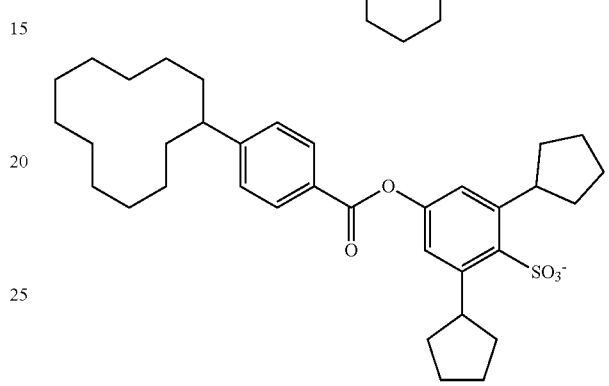
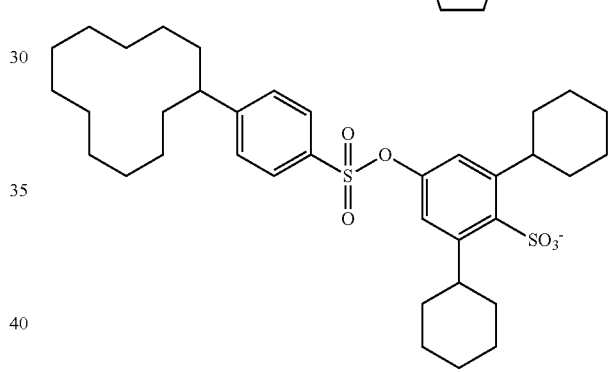
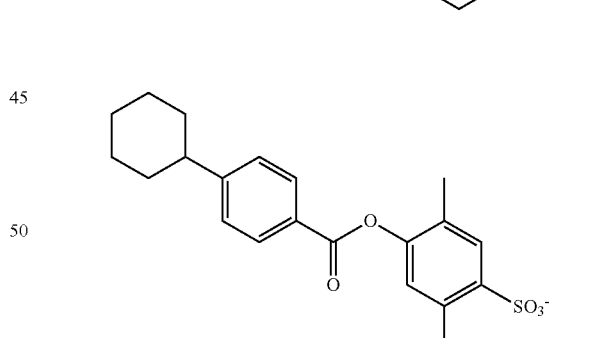
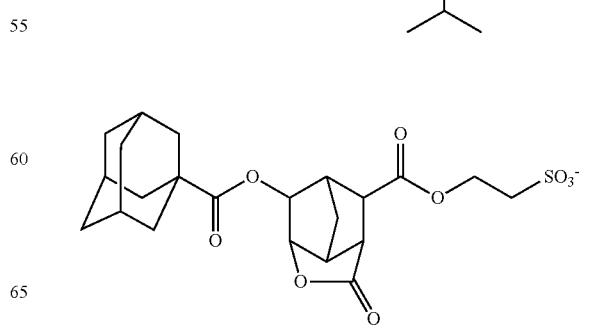

51
-continued
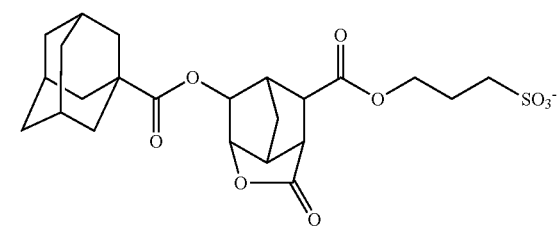
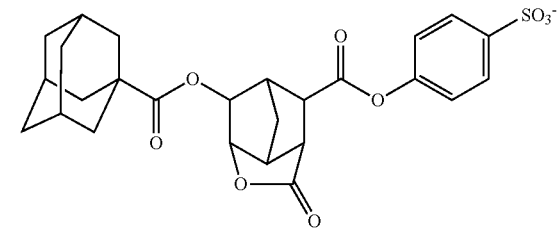
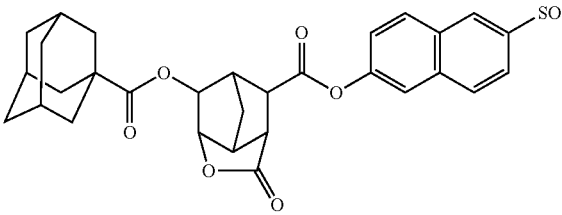
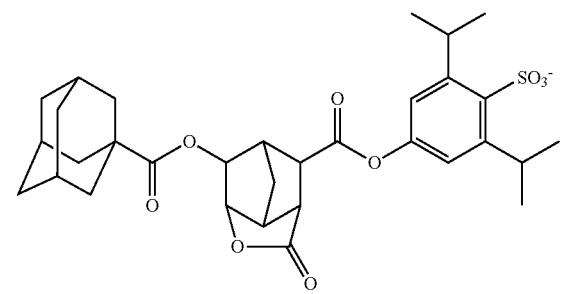
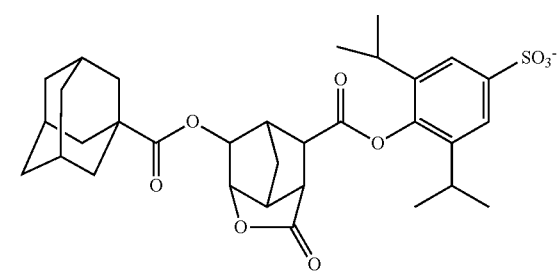
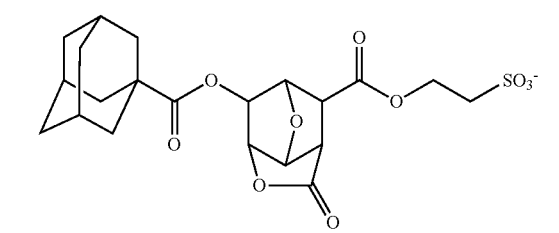
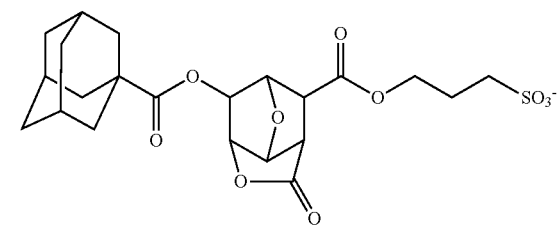
52
-continued
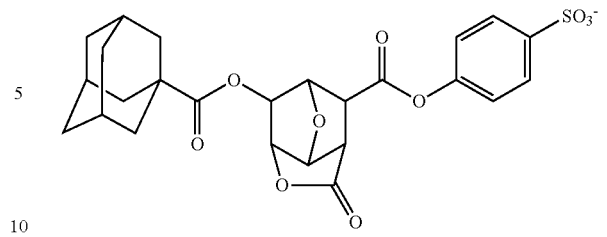
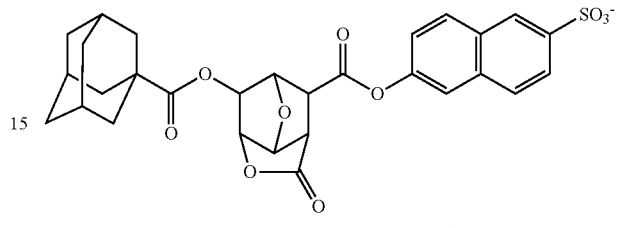
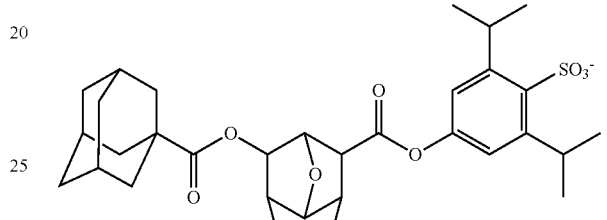
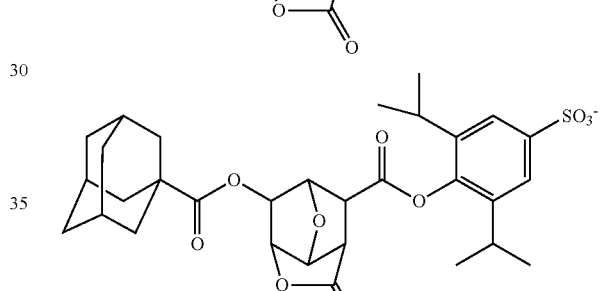
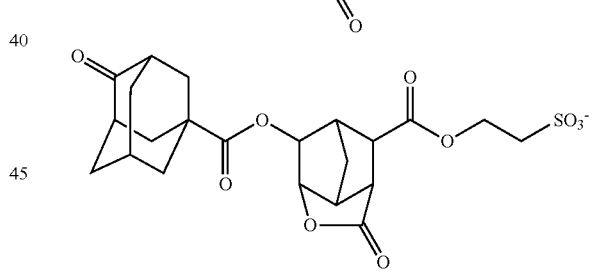
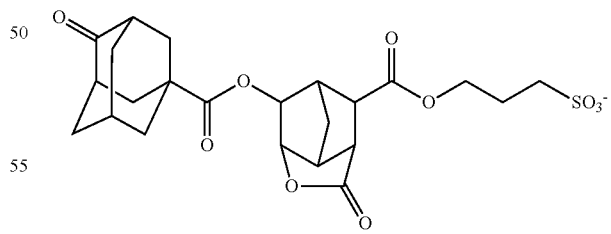
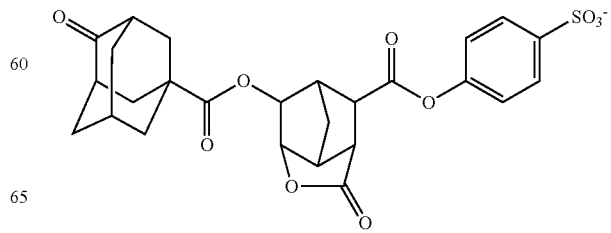

53
-continued
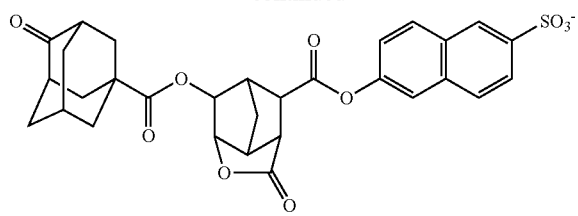
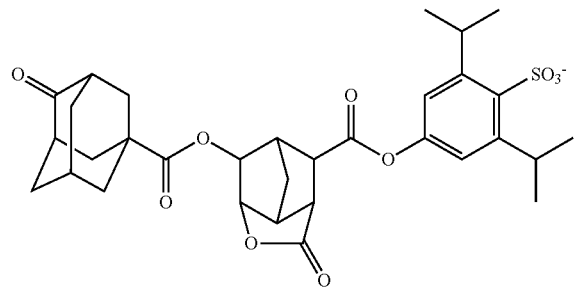
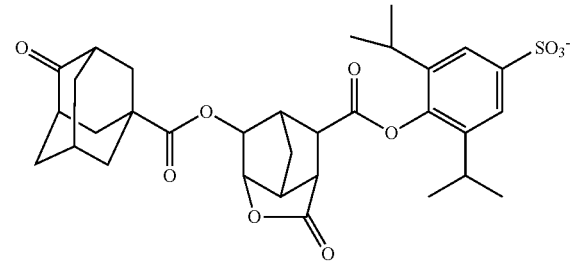
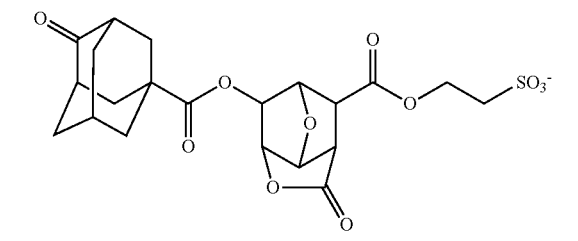
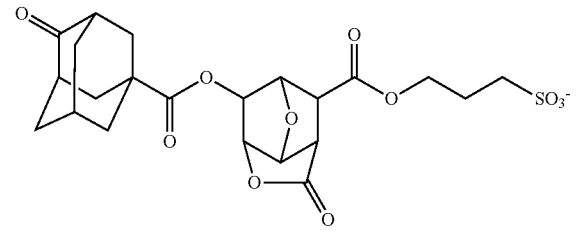
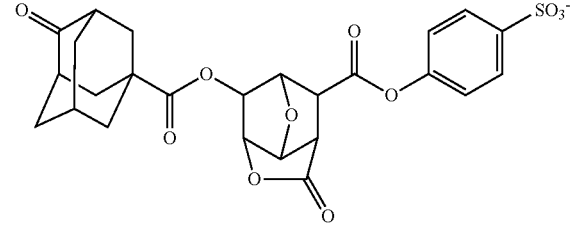
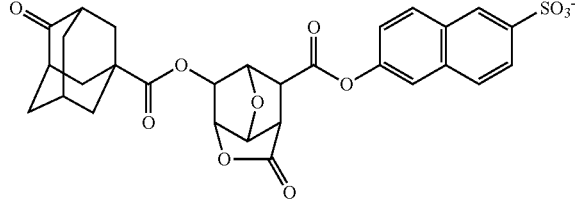
54
-continued
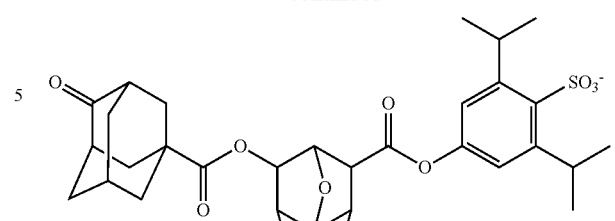
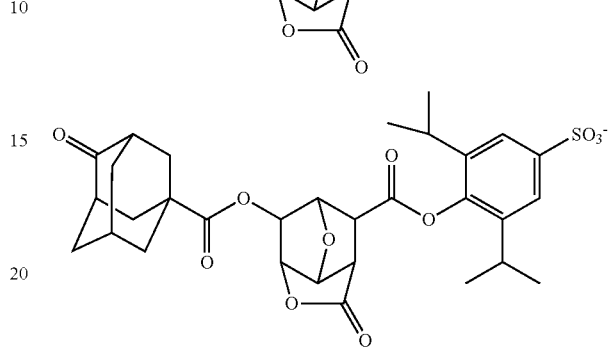
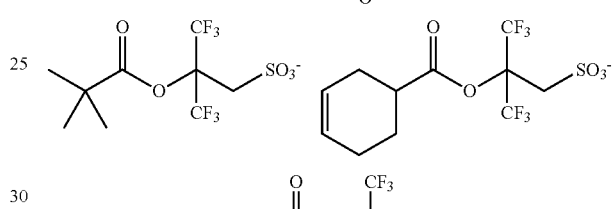
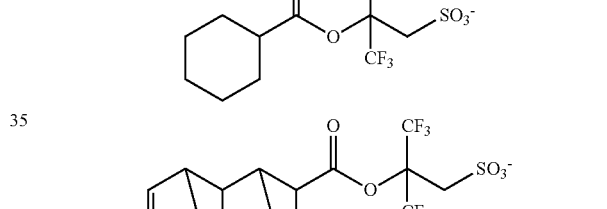
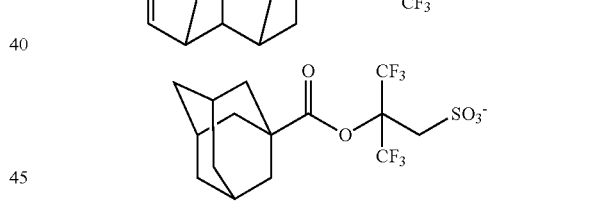
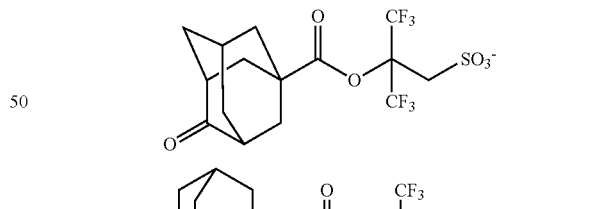
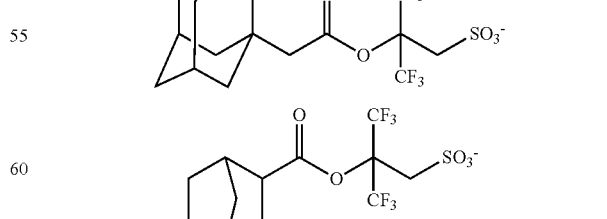

-continued

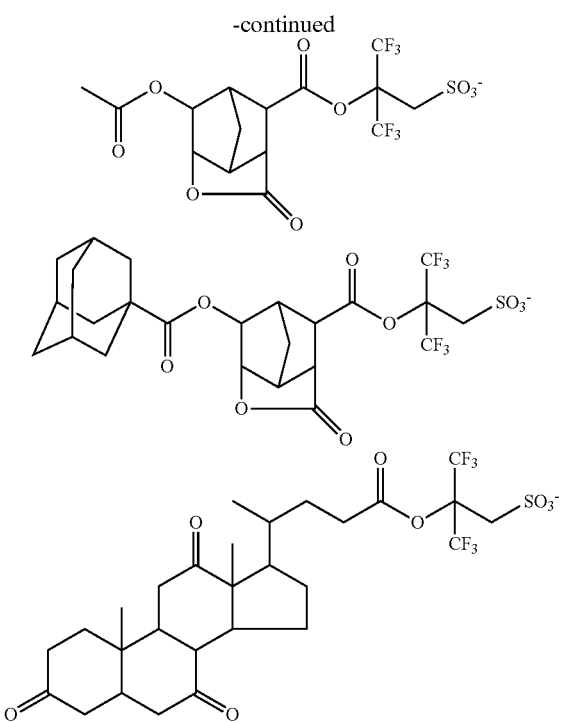

An appropriate amount of the PAG (E) used is 1 to 30 parts, more preferably 2 to 20 parts by weight per 100 parts by weight of the base polymer (B). Where the base polymer contains recurring units (B6) to (B9), the PAG (E) may be omitted.

(F) Basic Compound

In the resist composition, (F) a basic compound may be added as the acid diffusion inhibitor (other than component (A)) for the purpose of correcting a pattern profile or the like. The basic compound is effective for controlling acid diffusion. Even when the resist film is applied to a processable substrate having an outermost surface layer made of a chromium-containing material, the basic compound is effective for minimizing the influence of the acid generated in the resist film on the chromium-containing material. An appropriate amount of the basic compound added is 0 to 10 parts, and more preferably 0 to 5 parts by weight per 100 parts by weight of the base polymer (B).

Numerous basic compounds are known useful including primary, secondary, and tertiary aliphatic amines, mixed amines, aromatic amines, heterocyclic amines, nitrogen-containing compounds with carboxyl group, nitrogen-containing compounds with sulfonyl group, nitrogen-containing compounds with hydroxyl group, nitrogen-containing compounds with hydroxyphenyl group, alcoholic nitrogen-containing compounds, amide derivatives, imide derivatives, carbamate derivatives, and ammonium salts. Examples are described in Patent Document 9, for example, and any such compounds are useful. Of the foregoing basic compounds, preferred are tris[2-(methoxymethoxy)ethyl]amine, tris[2-(methoxymethoxy)ethyl]amine-N-oxide, dibutylaminobenzoic acid, morpholine derivatives and imidazole derivatives. The basic compounds may be used alone or in admixture.

(G) Surfactant

In the resist composition, any of surfactants commonly used for improving coating characteristics to the processable substrate may be added as an optional component. Numerous surfactants are known in the art, as described in JP-A 2004-115630, for example. A choice may be made with reference to such patent documents. An appropriate amount of the surfactant (G) used is 0 to 5 parts by weight per 100 parts by weight of the base polymer (B).

Process

A further embodiment of the invention is a resist pattern forming process comprising the steps of applying the resist composition defined above onto a processable substrate to form a resist film thereon, exposing the resist film pattern wise to high-energy radiation, and developing the resist film in an alkaline developer to form a resist pattern.

Pattern formation using the resist composition of the invention may be performed by well-known lithography processes. In general, the resist composition is first applied onto a processable substrate such as a substrate for IC fabrication (e.g., Si, $SiO_2$, SiN, SiON, TiN, WSi, BPSG, SOG, organic antireflective coating, etc.) or a substrate for mask circuit fabrication (e.g., Cr, CrO, CrON, $MoSi_2$, Si, SiO, $SiO_2$, etc.) by a suitable coating technique such as spin coating. The coating is prebaked on a hotplate at a temperature of 60 to 150° C. for 1 to 20 minutes, preferably 80 to 140° C. for 1 to 10 minutes to form a resist film of 0.03 to 2 μm thick.

Then the resist film is exposed patternwise to high-energy radiation such as UV, deep UV, excimer laser, EUV, x-ray, γ-ray or synchrotron radiation through a mask having a desired pattern or directly by EB writing. The exposure dose is preferably 1 to 300 $mJ/cm^2$, more preferably 10 to 200 $mJ/cm^2$ in the case of high-energy radiation or 1 to 300 $\mu C/cm^2$, more preferably 10 to 200 $\mu C/cm^2$ in the case of EB. The resist composition of the invention is especially effective on patternwise exposure to EUV or EB. The exposure may be performed by conventional lithography whereas the immersion lithography of holding a liquid between the mask and the resist film may be employed if desired. When the immersion lithography is applied, a protective film which is insoluble in water may be formed on the resist film.

The resist film is then baked (PEB) on a hotplate at 60 to 150° C. for 1 to 20 minutes, preferably 80 to 140° C. for 1 to 10 minutes. Thereafter the resist film is developed with a developer in the form of an aqueous base solution, for example, 0.1 to 5 wt %, preferably 2 to 3 wt % aqueous solution of tetramethylammonium hydroxide (TMAH) for 0.1 to 3 minutes, preferably 0.5 to 2 minutes by conventional techniques such as dip, puddle and spray techniques. In this way, a desired resist pattern is formed on the substrate.

From the resist composition, a pattern with a high resolution and minimal LER may be formed. The resist composition is effectively applicable to a processable substrate, specifically a substrate having a surface layer of material to which a resist film is less adherent and which is likely to invite pattern stripping or pattern collapse, and particularly a substrate having sputter deposited thereon metallic chromium or a chromium compound containing at least one light element selected from oxygen, nitrogen and carbon or a substrate having an outermost surface layer of $SiO_x$. The invention is especially effective for pattern formation on a photomask blank as the substrate.

Even on use of a processable substrate having an outermost surface layer made of a chromium or silicon-containing material which tends to adversely affect the profile of resist pattern, typically photomask blank, the resist pattern forming process is successful in forming a pattern with a high resolution and reduced LER via exposure to high-energy radiation because the resist composition is effective for controlling acid diffusion at the substrate interface.

EXAMPLE

Examples of the invention are given below by way of illustration and not by way of limitation. The abbreviation "pbw" is parts by weight. Me stands for methyl. The copolymer composition is expressed by a molar ratio. Mw is measured by GPC versus polystyrene standards. Analytic instruments are as shown below.
IR: NICOLET 6700 by Thermo Fisher Scientific Inc.
$^1$H-NMR: ECA-500 by JEOL Ltd.
MALDI-TOF-MS: S3000 by JEOL Ltd.

1) Synthesis of Sulfonium Compounds

Synthesis Example 1: Synthesis of Intermediates

Synthesis Example 1-1

Synthesis of 2-phenylthiobenzoic Acid (Intermediate A)

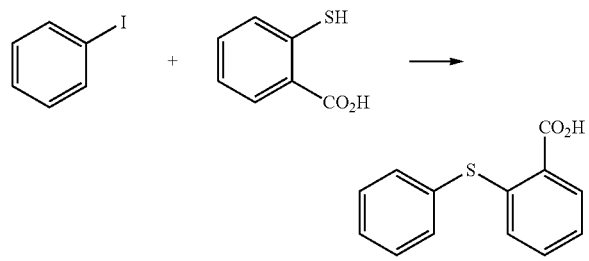

A mixture of 3 g of thiosalicylic acid, 6 g of potassium carbonate, 5 g of iodobenzene, 100 mg of copper iodide, and 10 g of N-methylpyrrolidone was stirred at 100° C. for 10 hours. The reaction solution was cooled to room temperature, to which 30 g of 10 wt % hydrochloric acid was added to quench the reaction. Ethyl acetate, 50 g, was added to the solution, followed by water washing, separation, and vacuum concentration. Hexane was added to the concentrate for recrystallization. The resulting crystal was filtered and dried in vacuum at elevated temperature, obtaining the desired compound, Intermediate A (amount 4 g, yield 90%).

Synthesis Example 1-2

Synthesis of methyl 2-phenylthiobenzoate (Intermediate B)

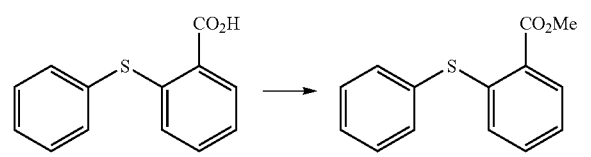 [SMILES: O=C(O)c1ccccc1Sc1ccccc1 ; COC(=O)c1ccccc1Sc1ccccc1]

Intermediate A, 4 g, was dissolved in 20 g of methanol, to which 80 mg of conc. sulfuric acid was added. The solution was stirred under reflux for 50 hours. The solution was cooled to room temperature and concentrated under reduced pressure. Toluene was added to the concentrate, followed by water washing, separation, and vacuum concentration again. The desired compound, Intermediate B was obtained as oily matter (amount 4 g, yield 92%).

Synthesis Example 1-3

Synthesis of (2-methoxycarbonylphenyl)diphenylsulfonium methylsulfate (Intermediate C)

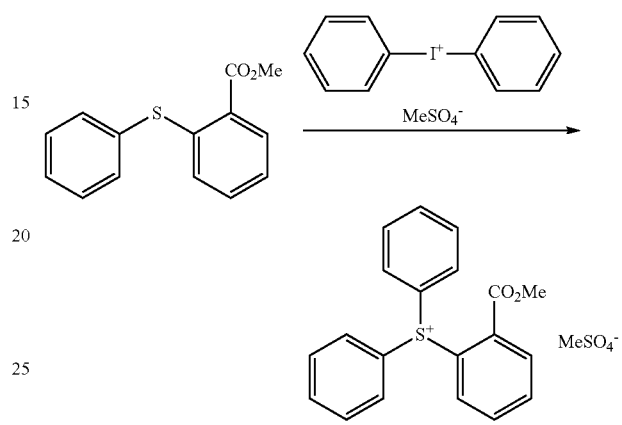

A mixture of 4 g of Intermediate B, 6 g of diphenyliodonium methylsulfate, 140 mg of copper(II) benzoate, and 20 g of anisole was stirred at 80° C. for 3 hours. The solution was cooled to room temperature, 30 g of diisopropyl ether was added thereto, and the supernatant was removed. The residue was purified by column chromatography, and diisopropyl ether was added thereto for crystallization. The crystal was filtered and dried in vacuum at elevated temperature, obtaining the desired compound, Intermediate C in powder form (amount 2 g, yield 32%).

Synthesis Example 1-4

Synthesis of (4-tert-butylphenyl)(2-methoxycarbonylphenyl)phenylsulfonium trifluoromethanesulfonate (Intermediate D)

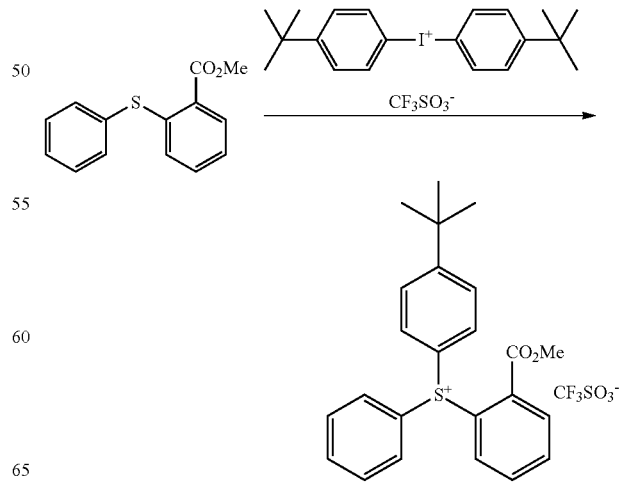

A mixture of 7 g of Intermediate B, 16 g of bis(4-tert-butylphenyl)iodonium trifluoromethanesulfonate, 280 mg of copper(II) benzoate, and 35 g of anisole was stirred at 120° C. for 3 hours. The solution was cooled to room temperature, 30 g of diisopropyl ether was added thereto, and the supernatant was removed. Methylene chloride was added to the residue for dissolution, followed by water washing, separation, and vacuum concentration. The desired compound, Intermediate D was obtained as oily matter (amount 13 g, yield 72%).

Synthesis Example 1-5

Synthesis of 2-(4-tert-butylphenyl)thiobenzoic acid (Intermediate E)

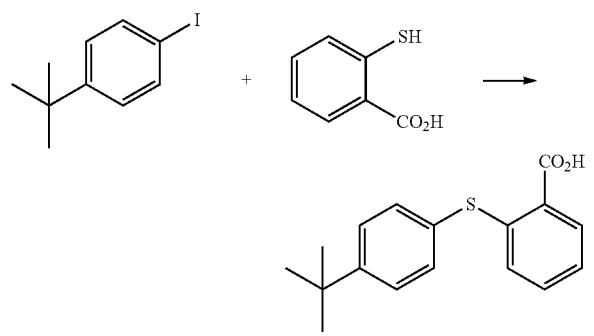

A mixture of 12 g of thiosalicylic acid, 24 g of potassium carbonate, 25 g of 4-tert-butyliodobenzene, 380 mg of copper iodide, and 74 g of N-methylpyrrolidone was stirred at 100° C. for 10 hours. The reaction solution was cooled to room temperature, to which 400 g of 5 wt % hydrochloric acid was added to quench the reaction. Ethyl acetate, 400 g, was added to the solution, followed by water washing, separation, and vacuum concentration. Hexane was added to the concentrate for recrystallization. The resulting crystal was filtered and dried in vacuum at elevated temperature, obtaining the desired compound, Intermediate E (amount 18 g, yield 81%).

Synthesis Example 1-6

Synthesis of methyl 2-(4-tert-butylphenyl)phenylthiobenzoate (Intermediate F)

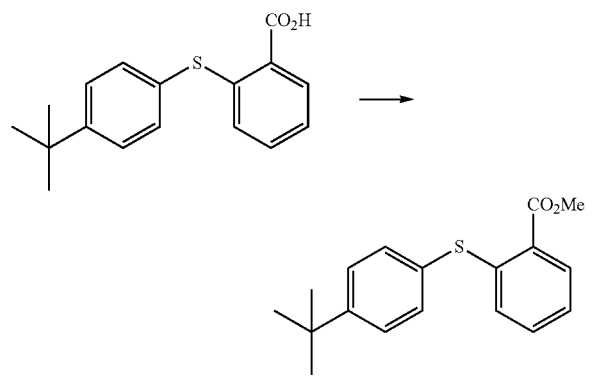

Intermediate E, 18 g, was dissolved in 150 g of methanol, to which 0.7 g of conc. sulfuric acid was added. The solution was stirred under reflux for 30 hours. The solution was cooled to room temperature and concentrated under reduced pressure. Toluene was added to the concentrate, followed by water washing, separation, and vacuum concentration again. The desired compound, Intermediate F was obtained as oily matter (amount 18 g, yield 91%).

Synthesis Example 1-7

Synthesis of {bis(4-tert-butylphenyl)}(2-methoxy-carbonylphenyl)sulfonium trifluoromethanesulfonate (Intermediate G)

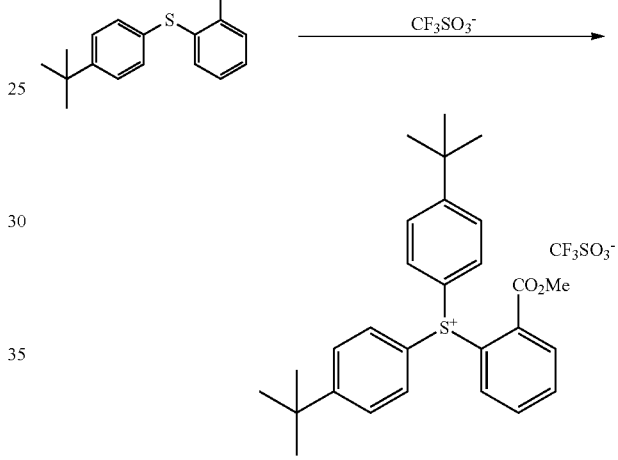

A mixture of 6 g of Intermediate F, 11 g of bis(4-tert-butylphenyl)iodonium trifluoromethanesulfonate, 180 mg of copper(II) benzoate, and 30 g of anisole was stirred at 120° C. for 3 hours. The solution was cooled to room temperature, 30 g of diisopropyl ether was added thereto, and the supernatant was removed. The residue was dissolved in methylene chloride, followed by water washing, separation, and vacuum concentration. The desired compound, Intermediate G was obtained as oily matter (amount 10 g, yield 72%).

Synthesis Example 1-8

Synthesis of 2-diphenylsulfoniobenzoate (Q-1)

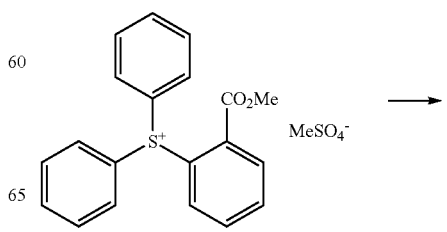

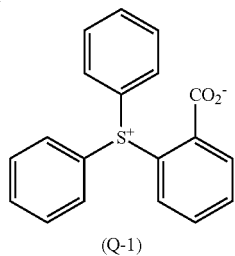

(Q-1)

To 10 g of water were added 1.7 g of Intermediate C and 0.16 g of sodium hydroxide. The resulting solution was stirred overnight at room temperature. To the solution was added 20 g of methylene chloride. The organic layer was extracted and concentrated in vacuum. Methyl isobutyl ketone was added to the concentrate, followed by vacuum concentration again. Diisopropyl ether was added to the concentrate for crystallization. The crystal was filtered and dried in vacuum at elevated temperature, obtaining the target compound, 2-diphenylsulfoniobenzoate (Q-1) in powder form (amount 0.6 g, yield 50%).

The target compound was analyzed by spectroscopy. The NMR spectrum, $^1$H-NMR in DMSO-$d_6$ is shown in FIG. 1. In $^1$H-NMR analysis, minute amounts of residual solvents (diisopropyl ether, methyl isobutyl ketone, methylene chloride) and water were observed.

Infrared absorption spectrum (IR (D-ATR)):
ν=3511, 3420, 1616, 1565, 1476, 1447, 1366, 1356, 829, 757, 748, 689 cm$^{-1}$ Time-of-flight mass spectrometry (TOF-MS; MALDI)
Positive [M+H]$^+$ 307 (corresponding to $C_{19}H_{15}O_2S^+$)

Synthesis Example 1-9

Synthesis of 2-{(4-tert-butylphenyl)(phenyl)}sulfoniobenzoate (Q-2)

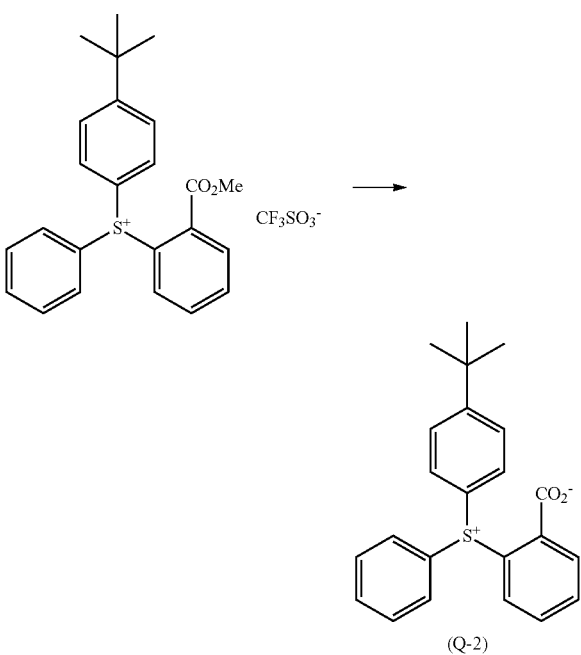

(Q-2)

To 70 g of water were added 11 g of Intermediate D and 1 g of sodium hydroxide. The resulting solution was stirred at room temperature for 4 hours. To the solution was added tert-butyl methyl ether. The water layer was separated. Methylene chloride, 100 g, was added thereto, followed by water washing, separation, and vacuum concentration. Methyl isobutyl ketone was added to the concentrate, followed by vacuum concentration again. The residue which precipitated as solid was recovered, obtaining the target compound, 2-{(4-tert-butylphenyl)(phenyl)}sulfoniobenzoate (0-2) in powder form (amount 6 g, yield 71%).

The target compound was analyzed by spectroscopy. The NMR spectrum, $^1$H-NMR in DMSO-$d_6$ is shown in FIG. 2. In $^1$H-NMR analysis, minute amounts of residual solvent (methyl isobutyl ketone) and water were observed.

IR (D-ATR):
ν=3409, 3058, 2958, 2905, 2868, 1705, 1616, 1562, 1491, 1476, 1444, 1396, 1343, 1268, 1073, 823, 756, 706, 685, 591, 554 cm$^{-1}$

TOFMS; MALDI
Positive [M+H]$^+$ 363 (corresponding to $C_{23}H_{23}O_2S^+$)

Synthesis Example 1-10

Synthesis of 2-{bis(4-tert-butylphenyl)}sulfoniobenzoate (Q-3)

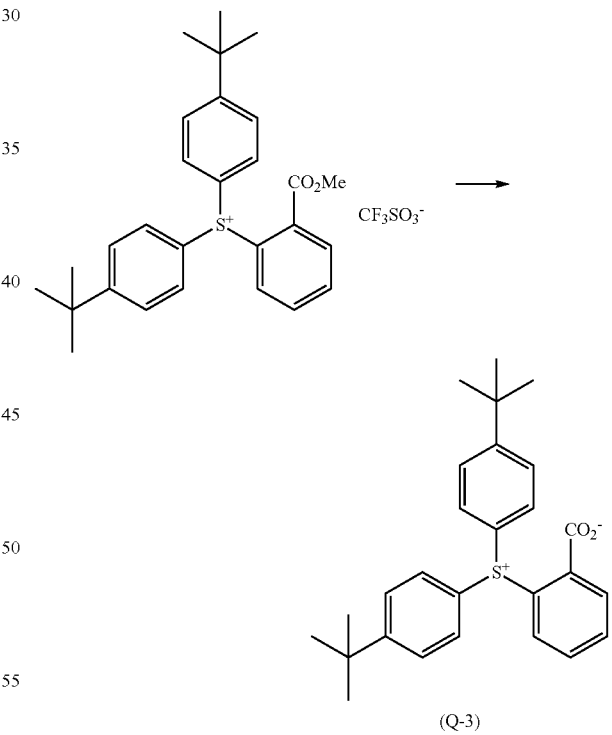

(Q-3)

To 30 g of water were added 8 g of Intermediate G, 30 g of methyl isobutyl ketone, and 0.6 g of sodium hydroxide. The resulting solution was stirred overnight at room temperature. The organic layer was separated, followed by water washing, separation, and vacuum concentration. To the residue was added tert-butyl methyl ether. The supernatant was removed. Diisopropyl ether was added to the residue for crystallization. The crystal was filtered and dried in vacuum at elevated temperature, obtaining the target compound, 2-{bis(4-tert-butylphenyl)}sulfoniobenzoate (Q-3) in powder form (amount 2.5 g, yield 39%).

The target compound was analyzed by spectroscopy. The NMR spectrum, $^1$H-NMR in DMSO-$d_6$ is shown in FIG. 3. In 1H-NMR analysis, minute amounts of residual solvents (tert-butyl methyl ether, diisopropyl ether) were observed.

IR (D-ATR):
ν=2962, 2904, 2869, 1631, 1562, 1490, 1463, 1397, 1363, 1340, 1268, 1112, 1075, 1009, 823, 757, 705, 683, 652, 601, 551 cm$^{-1}$

TOFMS; MALDI
Positive [M+H]$^+$ 419 (corresponding to $C_{27}H_{31}O_2S^+$)

2) Synthesis of Polymers

Synthesis Example 2-1

Synthesis of Polymer A1

A 3-L flask was charged with 407.5 g of acetoxystyrene, 42.5 g of acenaphthylene, and 1,275 g of toluene as solvent. The reactor was cooled at −70° C. in a nitrogen atmosphere, after which vacuum pumping and nitrogen flow were repeated three times. The reactor was warmed up to room temperature, whereupon 34.7 g of 2,2'-azobis(2,4-dimethylvaleronitrile) (V-65 by Wako Pure Chemical Industries, Ltd.) was added as polymerization initiator. The reactor was heated at 55° C., whereupon reaction ran for 40 hours. With stirring, a mixture of 970 g of methanol and 180 g of water was added dropwise to the reaction solution. The solution separated into two layers during 30 minutes of standing. The lower layer (polymer layer) was concentrated under reduced pressure. The polymer layer concentrate was dissolved again in 0.45 L of methanol and 0.54 L of tetrahydrofuran (THF), to which 160 g of triethylamine and 30 g of water were added. The reaction mixture was heated at 60° C. for 40 hours for deprotection reaction. The reaction solution was concentrated under reduced pressure. To the concentrate, 548 g of methanol and 112 g of acetone were added for dissolution. With stirring, 990 g of hexane was added dropwise to the solution. The solution separated into two layers during 30 minutes of standing. To the lower layer (polymer layer) was added 300 g of THF. With stirring, 1,030 g of hexane was added dropwise thereto. After 30 minutes of standing, the lower layer (polymer layer) was concentrated under reduced pressure. The polymer solution was neutralized with 82 g of acetic acid. The reaction solution was concentrated, dissolved in 0.3 L of acetone, and poured into 10 L of water for precipitation. The precipitate was filtered and dried, yielding 280 g of a white polymer. On analysis by $^1$H-NMR and GPC, the polymer had a copolymer compositional ratio of hydroxystyrene:acenaphthylene=89.3:10.7, Mw=5,000, and Mw/Mn=1.63.

Under acidic conditions, 100 g of the polymer was reacted with 50 g of 2-methyl-1-propenyl methyl ether. This was followed by neutralization, phase separation, and crystallization, obtaining 125 g of a polymer, designated Polymer A1.

Synthesis Examples 2-2 to 2-18

Synthesis of Polymers A2 to A14 and Polymers P1 to P4

Polymers A2 to A14 and Polymers P1 to P4 were synthesized as in Synthesis Example 2-1 aside from changing the monomers and reagents.

Polymers A1 to A14 and Polymers P1 to P4 had the following structures.

Polymer A1

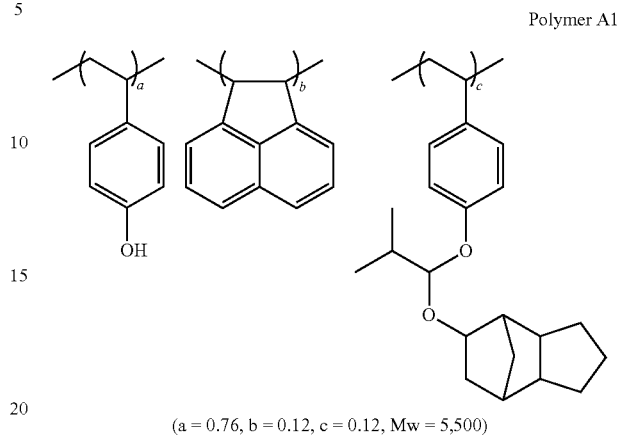

(a = 0.76, b = 0.12, c = 0.12, Mw = 5,500)

Polymer A2

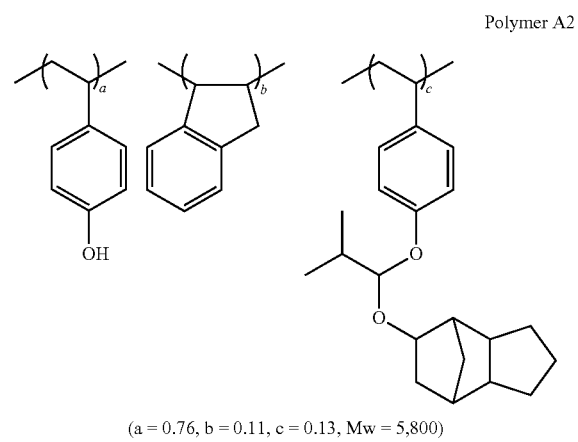

(a = 0.76, b = 0.11, c = 0.13, Mw = 5,800)

Polymer A3

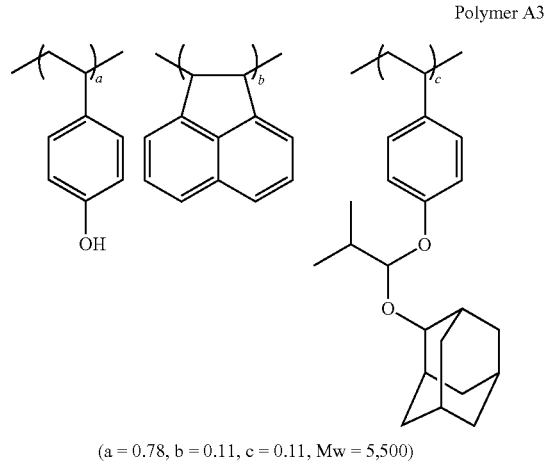

(a = 0.78, b = 0.11, c = 0.11, Mw = 5,500)

-continued
Polymer A4
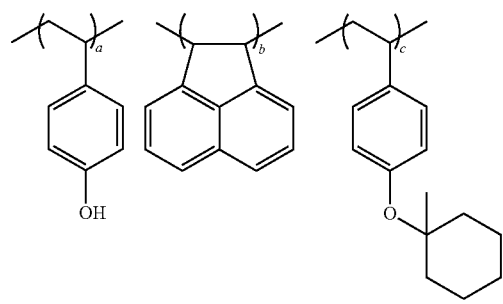
(a = 0.69, b = 0.10, c = 0.21, Mw = 4,000)
Polymer A5
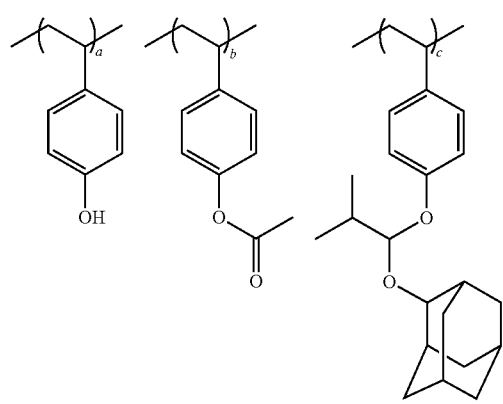
(a = 0.73, b = 0.12, c = 0.15, Mw = 5,700)
Polymer A6
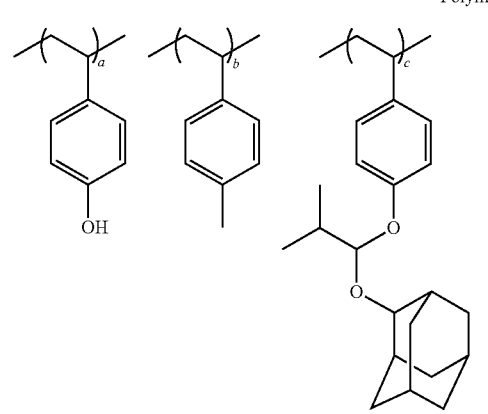
(a = 0.73, b = 0.13, c = 0.14, Mw = 5,400)
Polymer A7
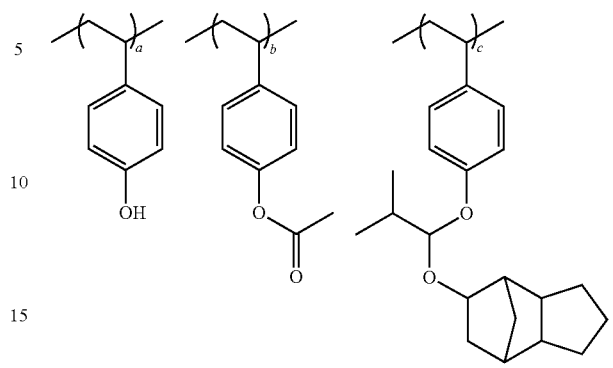
(a = 0.72, b = 0.12, c = 0.16, Mw = 5,800)
Polymer A8
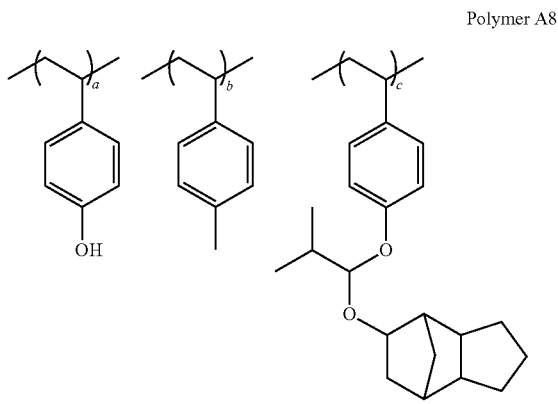
(a = 0.72, b = 0.12, c = 0.16, Mw = 5,900)
Polymer A9
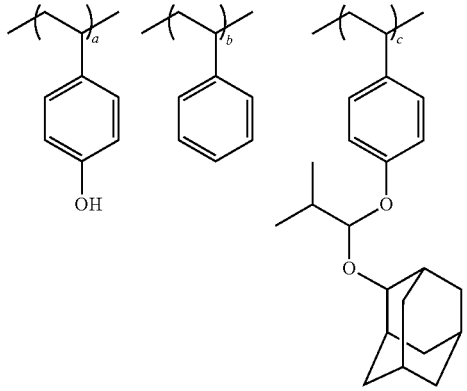
(a = 0.73, b = 0.12, c = 0.15, Mw = 5,700)

Polymer A10
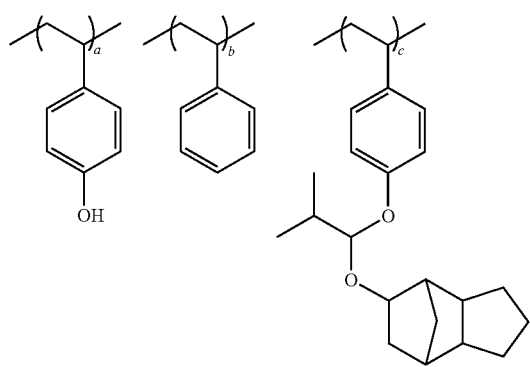
(a = 0.72, b = 0.12, c = 0.16, Mw = 5,700)
Polymer A11
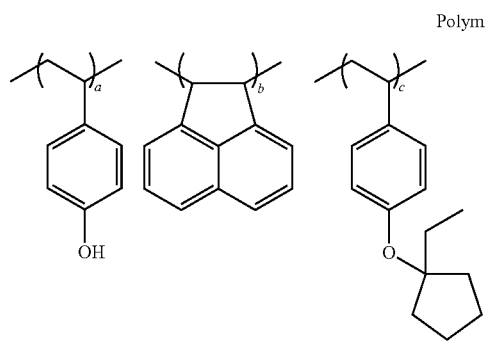
(a = 0.67, b = 0.10, c = 0.23, Mw = 4,100)
Polymer A12
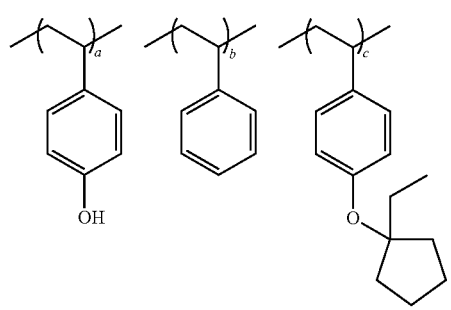
(a = 0.64, b = 0.12, c = 0.24, Mw = 5,400)
Polymer A13
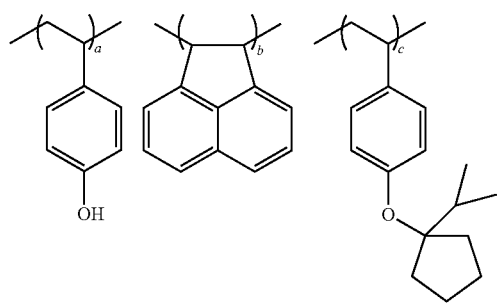
(a = 0.68, b = 0.12, c = 0.20, Mw = 4,200)
Polymer A14
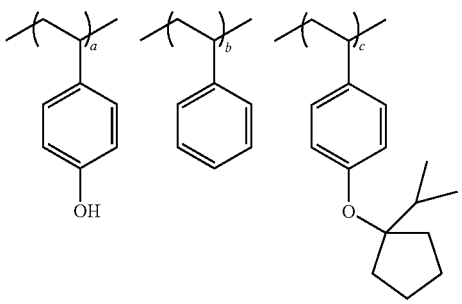
(a = 0.68, b = 0.11, c = 0.21, Mw = 4,000)
Polymer P1
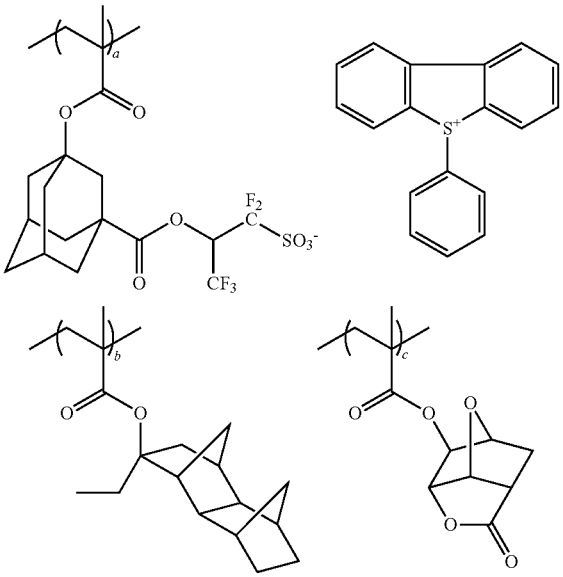
(a = 0.20, b = 0.30, c = 0.30, d = 0.20, Mw = 14,500)
Polymer P2
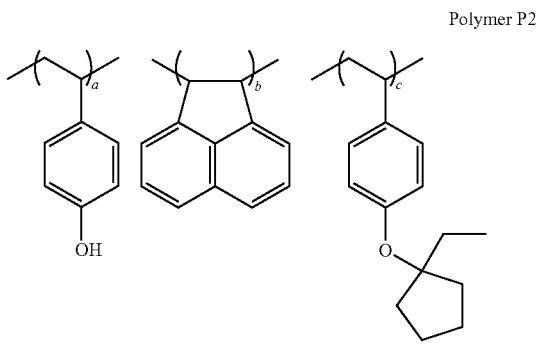

-continued

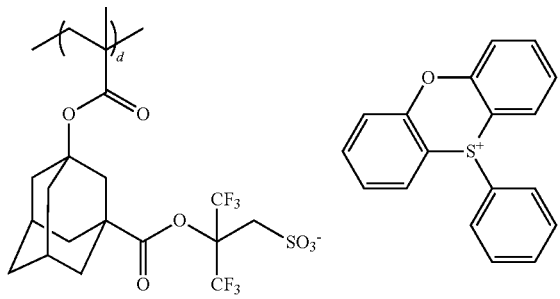

(a = 0.55, b = 0.10, c = 0.25, d = 0.10, Mw = 7,200)

Polymer P3

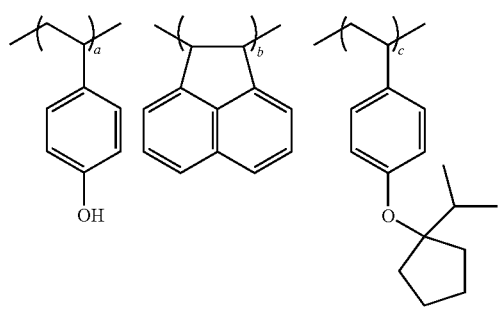

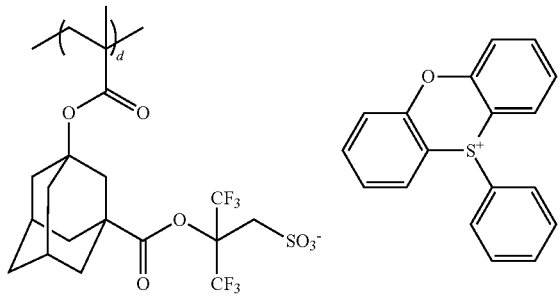

(a = 0.58, b = 0.09, c = 0.20, d = 0.13, Mw = 7,300)

Polymer P4

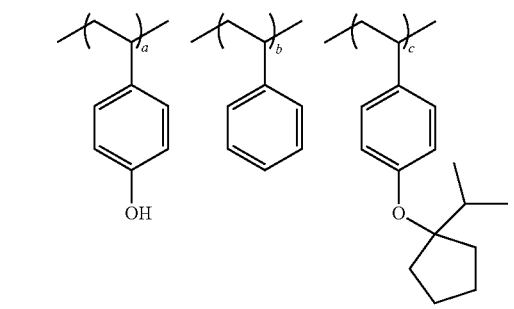

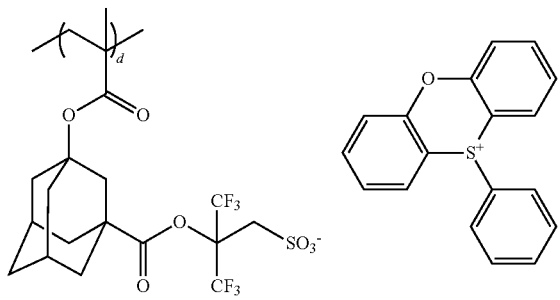

(a = 0.55, b = 0.12, c = 0.20, d = 0.13, Mw = 7,100)

3) Preparation of Positive Resist Compositions

Examples 1-1 to 1-35 and Comparative Examples 1-1 to 1-2

The acid diffusion inhibitor is selected from sulfonium compounds Q-1 to Q-3 synthesized in Synthesis Examples and comparative acid diffusion inhibitors Q-4, Q-5; the base polymer is from Polymers A1 to A14 and Polymers P1 to P4; the photoacid generator is from PAG-A to PAG-C; and the additive is from fluorinated polymers, i.e., Polymers C1 to C3. A positive resist composition in solution form was prepared by dissolving the components in an organic solvent according to the formulation shown in Tables 1 and 2, and filtering through a UPE filter with a pore size of 0.02 μm. The organic solvents in Tables 1 and 2 are PGMEA (propylene glycol monomethyl ether acetate), EL (ethyl lactate), PGME (propylene glycol monomethyl ether), and CyH (cyclohexanone). In each composition, 0.075 pbw of surfactant PF-636 (Omnova Solutions) was added per 100 pbw of solids.

Notably, Q-4, Q-5, PAG-A, PAG-B, PAG-C, and Polymers C1 to C3 are identified below.

Q-4

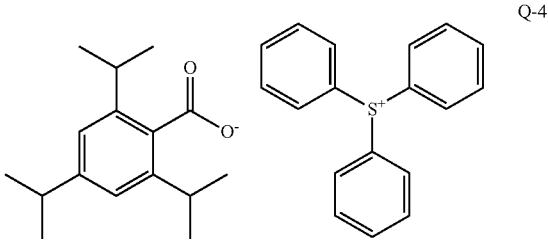

Q-5

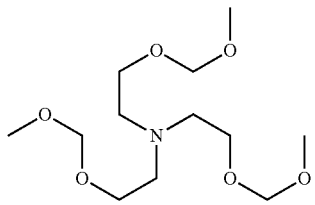

PAG-A

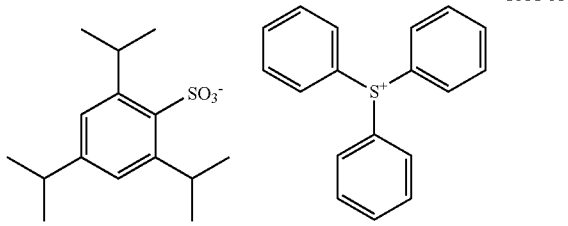

PAG-B

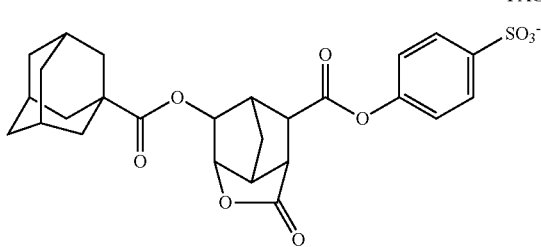

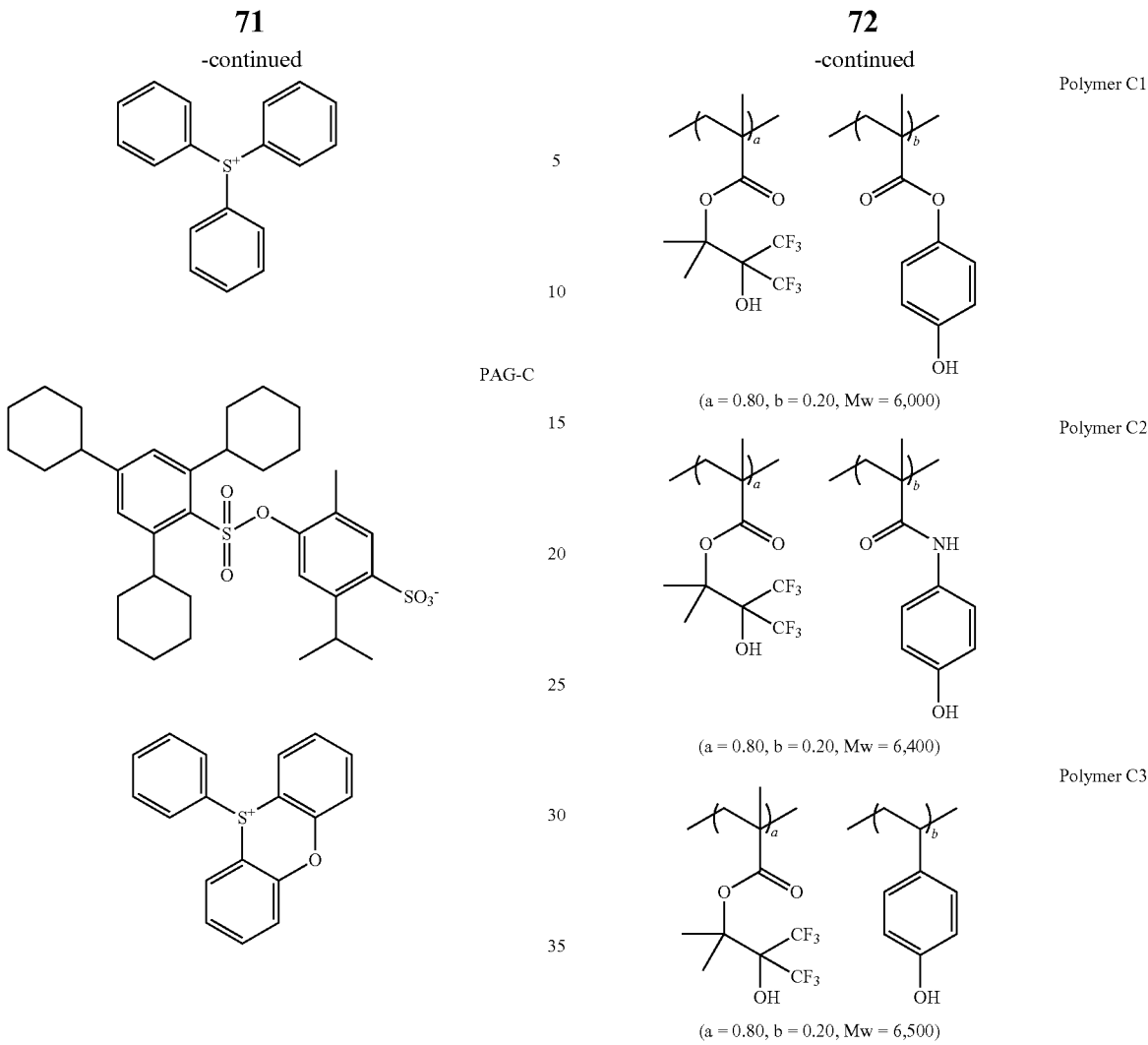

TABLE 1

| | | Resist composition | Acid diffusion inhibitor (pbw) | Polymer 1 (pbw) | Polymer 2 (pbw) | Acid generator (pbw) | Additive (pbw) | Solvent 1 (pbw) | Solvent 2 (pbw) | Solvent 3 (pbw) |
|---|---|---|---|---|---|---|---|---|---|---|
| Example | 1-1 | R-1 | Q-1 (3.0) | Polymer A1 (80) | | PAG-A (9) | | PGMEA (1,160) | EL (2,706) | |
| | 1-2 | R-2 | Q-1 (3.0) | Polymer A1 (80) | | PAG-B (9) | | PGMEA (1,160) | EL (2,706) | |
| | 1-3 | R-3 | Q-1 (3.0) | Polymer A1 (80) | | PAG-C (9) | | PGMEA (1,160) | EL (2,706) | |
| | 1-4 | R-4 | Q-1 (5.5) | Polymer A1 (80) | | PAG-C (18) | | PGMEA (1,160) | EL (2,706) | |
| | 1-5 | R-5 | Q-1 (3.0) | Polymer A1 (80) | | PAG-C (9) | Polymer C1 (3) | PGMEA (1,160) | EL (2,706) | |
| | 1-6 | R-6 | Q-1 (3.0) | Polymer A1 (80) | | PAG-C (9) | Polymer C2 (3) | PGMEA (1,160) | EL (2,706) | |
| | 1-7 | R-7 | Q-1 (6.0) | Polymer A1 (80) | | PAG-C (9) | Polymer C3 (3) | PGMEA (1,160) | EL (2,706) | |
| | 1-8 | R-8 | Q-1 (3.0) | Polymer A2 (80) | | PAG-C (9) | | PGMEA (1,160) | EL (2,706) | |
| | 1-9 | R-9 | Q-1 (3.0) | Polymer A3 (80) | | PAG-C (9) | | PGMEA (1,160) | EL (2,706) | |
| | 1-10 | R-10 | Q-1 (3.0) | Polymer A4 (80) | | PAG-C (9) | | PGMEA (1,160) | EL (2,706) | |
| | 1-11 | R-11 | Q-1 (3.0) | Polymer A5 (80) | | PAG-C (9) | | PGMEA (1,160) | EL (2,706) | |
| | 1-12 | R-12 | Q-1 (3.0) | Polymer A6 (80) | | PAG-C (9) | | PGMEA (1,160) | EL (2,706) | |

TABLE 1-continued

|  | Resist composition | Acid diffusion inhibitor (pbw) | Polymer 1 (pbw) | Polymer 2 (pbw) | Acid generator (pbw) | Additive (pbw) | Solvent 1 (pbw) | Solvent 2 (pbw) | Solvent 3 (pbw) |
|---|---|---|---|---|---|---|---|---|---|
| 1-13 | R-13 | Q-1 (3.0) | Polymer A3 (40) | Polymer P1 (40) |  |  | PGMEA (1,160) | CyH (2,706) |  |
| 1-14 | R-14 | Q-1 (3.0) | Polymer A3 (40) | Polymer P2 (40) |  |  | PGMEA (386) | EL (1,932) | PGME (1,546) |
| 1-15 | R-15 | Q-1 (3.0) | Polymer A3 (40) | Polymer P2 (40) |  | Polymer C1 (8) | PGMEA (386) | EL (1,932) | PGME (1,546) |
| 1-16 | R-16 | Q-1 (3.0) | Polymer A3 (40) | Polymer P2 (40) |  | Polymer C2 (3) | PGMEA (386) | EL (1,932) | PGME (1,546) |
| 1-17 | R-17 | Q-1 (3.0) | Polymer A3 (40) | Polymer P2 (40) |  | Polymer C3 (3) | PGMEA (386) | EL (1,932) | PGME (1,546) |
| 1-18 | R-18 | Q-1 (3.0) | Polymer A3 (40) | Polymer P2 (40) | PAG-C (5) |  | PGMEA (386) | EL (1,932) | PGME (1,546) |
| 1-19 | R-19 | Q-2 (3.2) | Polymer A3 (80) |  | PAG-C (9) |  | PGMEA (1,160) | EL (2,706) |  |
| 1-20 | R-20 | Q-2 (3.2) | Polymer A3 (40) | Polymer P1 (40) |  |  | PGMEA (1,160) | CyH (2,706) |  |

TABLE 2

|  |  | Resist composition | Acid diffusion inhibitor (pbw) | Polymer 1 (pbw) | Polymer 2 (pbw) | Acid generator (pbw) | Additive (pbw) | Solvent 1 (pbw) | Solvent 2 (pbw) | Solvent 3 (pbw) |
|---|---|---|---|---|---|---|---|---|---|---|
| Example | 1-21 | R-21 | Q-2 (3.2) | Polymer A3 (40) | Polymer P2 (40) |  |  | PGMEA (386) | EL (1,932) | PGME (1,546) |
|  | 1-22 | R-22 | Q-3 (3.4) | Polymer A3 (80) |  | PAG-C (9) |  | PGMEA (1,160) | EL (2,706) |  |
|  | 1-23 | R-23 | Q-3 (3.4) | Polymer A3 (40) | Polymer P1 (40) |  |  | PGMEA (1,160) | EL (2,706) |  |
|  | 1-24 | R-24 | Q-3 (3.4) | Polymer A3 (40) | Polymer P1 (40) |  |  | PGMEA (386) | EL (1,932) | PGME (1,546) |
|  | 1-25 | R-25 | Q-2 (3.2) | Polymer A7 (80) |  | PAG-C (9) | Polymer C1 (3) | PGMEA (1,160) | EL (2,706) |  |
|  | 1-26 | R-26 | Q-2 (3.2) | Polymer A8 (80) |  | PAG-C (9) | Polymer C1 (3) | PGMEA (1,160) | EL (2,706) |  |
|  | 1-27 | R-27 | Q-2 (3.2) | Polymer A9 (80) |  | PAG-C (9) | Polymer C1 (3) | PGMEA (1,160) | EL (2,706) |  |
|  | 1-28 | R-28 | Q-2 (3.2) | Polymer A10 (80) |  | PAG-C (9) | Polymer C1 (3) | PGMEA (1,160) | EL (2,706) |  |
|  | 1-29 | R-29 | Q-2 (3.2) | Polymer A11 (80) |  | PAG-C (9) | Polymer C1 (3) | PGMEA (1,160) | EL (2,706) |  |
|  | 1-30 | R-30 | Q-2 (3.2) | Polymer A12 (80) |  | PAG-C (9) | Polymer C1 (3) | PGMEA (1,160) | EL (2,706) |  |
|  | 1-31 | R-31 | Q-2 (3.2) | Polymer A13 (80) |  | PAG-C (9) | Polymer C1 (3) | PGMEA (1,160) | EL (2,706) |  |
|  | 1-32 | R-32 | Q-2 (3.2) | Polymer A14 (80) |  | PAG-C (9) | Polymer C1 (3) | PGMEA (1,160) | EL (2,706) |  |
|  | 1-33 | R-33 | Q-2 (3.2) | Polymer A11 (40) | Polymer P2 (40) | PAG-A (5) | Polymer C1 (5) | PGMEA (386) | EL (1,932) | PGME (1,546) |
|  | 1-34 | R-34 | Q-2 (3.2) | Polymer A13 (40) | Polymer P3 (40) | PAG-A (5) | Polymer C1 (5) | PGMEA (386) | EL (1,332) | PGME (1,546) |
|  | 1-35 | R-35 | Q-2 (3.2) | Polymer A14 (40) | Polymer P4 (40) | PAG-A (5) | Polymer C1 (5) | PGMEA (386) | EL (1,932) | PGME (1,546) |
| Comparative Example | 1-1 | CR-1 | Q-4 (4.0) | Polymer A1 (80) |  | PAG-A (9) |  | PGMEA (1,160) | EL (2,706) |  |
|  | 1-2 | CR-2 | Q-5 (2.0) | Polymer A1 (80) |  | PAG-A (9) |  | PGMEA (1,160) | EL (2,706) |  |

4) EB Writing Test

Examples 2-1 to 2-35 and Comparative Examples 2-1 to 2-2

Using a coater/developer system ACT-M (Tokyo Electron Ltd.), each of the positive resist compositions (Examples and Comparative Examples) was spin coated onto a mask blank of 152 mm squares having the outermost surface of silicon oxide (vapor primed with hexamethyldisilazane (HMDS)) and prebaked on a hotplate at 110° C. for 600 seconds to form a resist film of 80 nm thick. The thickness of the resist film was measured by an optical film thickness measurement system Nanospec (Nanometrics Inc.). Measurement was made at 81 points in the plane of the blank substrate excluding a peripheral band extending 10 mm inward from the blank periphery, and an average film thickness and a film thickness range were computed therefrom.

The coated mask blanks were exposed to EB using an EB writer system EBM-5000Plus (NuFlare Technology Inc., accelerating voltage 50 kV), then baked (PEB) at 110° C. for 600 seconds, and developed in a 2.38 wt % tetramethylammonium hydroxide (TMAH) aqueous solution, thereby yielding positive patterns.

The patterned mask blank was observed under a top-down scanning electron microscope (TD-SEM). The optimum exposure (Eop) was defined as the exposure dose ($\mu C/cm^2$) which provided a 1:1 resolution at the top and bottom of a 200-nm 1:1 line-and-space pattern. The maximum resolution of the resist was defined as the minimum line width of a line-and-space pattern that could be resolved at the optimum exposure. The LER of a 200-nm line-and-space pattern was measured under SEM. On observation in cross section of the resist pattern under SEM, it was visually judged whether or not the pattern profile was rectangular. The test results of the resist compositions are shown in Table 3.

diffusion inhibitor. After imagewise exposure, the sulfonium compound having formula (A) is converted to carboxylic acid, losing the acid diffusion regulating ability. Therefore the reaction contrast between exposed and unexposed regions is enhanced. Comparative Example 2-2 is low in reaction contrast because Compound Q-5 used therein retains the acid diffusion regulating ability even after imagewise exposure. As a result, a pattern having satisfactory resolution and reduced LER is formed from the resist composition within the scope of the invention. This suggests that even when the resist composition is applied to a processable substrate having an outermost surface made of a material to which the resist pattern profile is sensitive, such as chromium or silicon-containing material, a pattern with high resolution and reduced LER can be formed through

TABLE 3

|  |  | Resist composition | Eop, $\mu C/cm^2$ | Maximum resolution (LS), nm | LER, nm | Pattern profile |
|---|---|---|---|---|---|---|
| Example | 2-1 | R-1 | 48 | 40 | 4.7 | rectangular |
|  | 2-2 | R-2 | 49 | 40 | 4.8 | rectangular |
|  | 2-3 | R-3 | 48 | 40 | 4.8 | rectangular |
|  | 2-4 | R-4 | 50 | 40 | 4.6 | rectangular |
|  | 2-5 | R-5 | 48 | 40 | 4.7 | rectangular |
|  | 2-6 | R-6 | 47 | 40 | 4.8 | rectangular |
|  | 2-7 | R-7 | 49 | 40 | 4.9 | rectangular |
|  | 2-8 | R-8 | 50 | 40 | 4.7 | rectangular |
|  | 2-9 | R-9 | 48 | 40 | 4.7 | rectangular |
|  | 2-10 | R-10 | 51 | 40 | 4.9 | rectangular |
|  | 2-11 | R-11 | 49 | 40 | 4.8 | rectangular |
|  | 2-12 | R-12 | 48 | 40 | 4.8 | rectangular |
|  | 2-13 | R-13 | 50 | 40 | 4.6 | rectangular |
|  | 2-14 | R-14 | 51 | 40 | 4.7 | rectangular |
|  | 2-15 | R-15 | 51 | 40 | 4.6 | rectangular |
|  | 2-16 | R-16 | 48 | 40 | 4.6 | rectangular |
|  | 2-17 | R-17 | 49 | 40 | 4.9 | rectangular |
|  | 2-18 | R-18 | 49 | 40 | 4.8 | rectangular |
|  | 2-19 | R-19 | 51 | 40 | 4.8 | rectangular |
|  | 2-20 | R-20 | 49 | 40 | 4.9 | rectangular |
|  | 2-21 | R-21 | 50 | 40 | 4.7 | rectangular |
|  | 2-22 | R-22 | 50 | 40 | 4.9 | rectangular |
|  | 2-23 | R-23 | 49 | 40 | 4.7 | rectangular |
|  | 2-24 | R-24 | 51 | 40 | 4.7 | rectangular |
|  | 2-25 | R-25 | 49 | 40 | 4.7 | rectangular |
|  | 2-26 | R-26 | 48 | 40 | 4.6 | rectangular |
|  | 2-27 | R-27 | 50 | 40 | 4.6 | rectangular |
|  | 2-28 | R-28 | 50 | 40 | 4.6 | rectangular |
|  | 2-29 | R-29 | 52 | 40 | 4.7 | rectangular |
|  | 2-30 | R-30 | 52 | 40 | 4.6 | rectangular |
|  | 2-31 | R-31 | 51 | 40 | 4.7 | rectangular |
|  | 2-32 | R-32 | 51 | 40 | 4.6 | rectangular |
|  | 2-33 | R-33 | 52 | 40 | 4.6 | rectangular |
|  | 2-34 | R-34 | 51 | 40 | 4.6 | rectangular |
|  | 2-35 | R-35 | 50 | 40 | 4.5 | rectangular |
| Comparative | 2-1 | CR-1 | 48 | 60 | 5.8 | inversely tapered |
| Example | 2-2 | CR-2 | 51 | 60 | 5.9 | inversely tapered |

As seen from the data in Table 3, the resist compositions of Examples 2-1 to 2-35 containing the sulfonium compound having formula (A) within the scope of the invention exhibit a high resolution, satisfactory pattern rectangularity, and acceptable values of LER. In contrast, the resist compositions of Comparative Examples 2-1 and 2-2 are inferior in resolution and LER. This is because the acid generated upon exposure diffuses into the unexposed region to induce the unwanted reaction that a few protective groups on the base polymer in the unexposed region are deprotected.

The resist compositions containing the sulfonium compound having formula (A) within the scope of the invention have a higher acid trapping ability and are less susceptible to the undesired reaction than the resist composition of Comparative Example 2-1 containing the comparative acid high-energy radiation exposure because the inventive resist composition containing the specific sulfonium compound is efficient for controlling acid diffusion at the substrate interface.

5) EB Writing Test after Coating of Antistatic Film

Examples 3-1 to 3-8 and Comparative Examples 3-1 to 3-2

Using a coater/developer system Clean Track Mark 8 (Tokyo Electron Ltd.), each of the positive resist compositions (Examples and Comparative Examples) was spin coated onto a 6-inch silicon wafer (vapor primed with HMDS) and baked at 110° C. for 240 seconds to form a resist film of 80 nm thick. Using Clean Track Mark 8, a conductive polymer composition was dispensed dropwise and spin coated over the entire resist film and baked on a hotplate at 90° C. for 90 seconds to form an anti-charging film of 60 nm thick. The conductive polymer composition used herein was a water dispersion of polystyrene-doped polyaniline as described in Proc. of SPIE Vol. 8522 852200-1.

The coated wafer was exposed to EB using an EB writer system HL-800D (Hitachi High-Technologies, Ltd., accelerating voltage 50 kV), rinsed with deionized water for 15 seconds to strip off the anti-charging film, then baked (PEB) at 110° C. for 240 seconds, and developed in a 2.38 wt % TMAH aqueous solution for 80 seconds, thereby yielding a positive pattern.

The patterned mask blank was observed under a TD-SEM. The optimum exposure (Eop) was defined as the exposure dose (μC/cm²) which provided a 1:1 resolution at the top and bottom of a 400-nm 1:1 line-and-space pattern. The maximum resolution of the resist was defined as the minimum line width of a line-and-space pattern that could be resolved at the optimum exposure. The results are shown in Table 4.

TABLE 4

| | | Resist composition | Eop, μC/cm² | Maximum resolution (LS), nm |
|---|---|---|---|---|
| Example | 3-1 | R-4 | 55 | 70 |
| | 3-2 | R-5 | 53 | 60 |
| | 3-3 | R-6 | 52 | 60 |
| | 3-4 | R-7 | 54 | 60 |
| | 3-5 | R-14 | 56 | 70 |
| | 3-6 | R-15 | 56 | 60 |
| | 3-7 | R-16 | 53 | 60 |
| | 3-8 | R-17 | 54 | 60 |
| Comparative Example | 3-1 | CR-1 | 53 | 80 |
| | 3-2 | CR-2 | 56 | 80 |

As seen from the data in Table 4, the resist compositions of Examples 3-1 to 3-8 containing the sulfonium compound having formula (A) as acid diffusion inhibitor within the scope of the invention exhibit a satisfactory resolution. In contrast, the resist compositions of Comparative Examples 3-1 and 3-2 are inferior in resolution. This is because the very weak acid in the anti-charging film induces the unwanted reaction to deprotect a few protective groups on the base polymer in the unexposed region. Since the resist composition containing the inventive sulfonium compound has a higher salt exchange efficiency than the resist composition of Comparative Example 3-1 containing the acid diffusion inhibitor 0-4 and reduced in intermixing between the resist layer and the anti-charging layer as compared to with Comparative Example 3-2, the likelihood of the unwanted reaction is reduced. As a result, a pattern with a higher resolution can be formed. A comparison of Examples 3-1 to 3-4 with Examples 3-5 to 3-8 reveals that resolution is further improved by adding fluorinated polymer (C) which is effective for suppressing acid mixing.

It has been demonstrated that using the resist composition within the scope of the invention, a pattern having a very high resolution and minimal LER can be formed via exposure and development. Even when the resist film is overlaid with an anti-charging film, the resist composition within the scope of the invention maintains a high resolution. The pattern forming process using the resist composition within the scope of the invention is advantageous in the photolithography for semiconductor device fabrication and photomask blank processing.

Japanese Patent Application No. 2016-154628 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A positive resist composition comprising (A) an acid diffusion inhibitor comprising a sulfonium compound having the formula (A), (B) a base polymer containing a polymer comprising recurring units having the formula (B1), adapted to be decomposed under the action of acid to increase its solubility in alkaline developer, and (E) a photoacid generator,

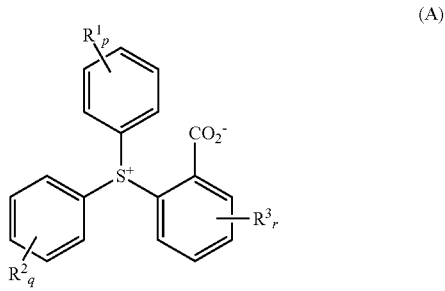

(A)

wherein $R^1$, $R^2$, and $R^3$ are each independently a $C_1$-$C_{20}$ straight, branched or cyclic monovalent hydrocarbon group which may contain a heteroatom, p and q are each independently an integer of 0 to 5, r is an integer of 0 to 4, in case of p=2 to 5, two adjoining groups $R^1$ may bond together to form a ring with the carbon atoms to which they are attached, in case of q=2 to 5, two adjoining groups $R^2$ may bond together to form a ring with the carbon atoms to which they are attached, in case of r=2 to 4, two adjoining groups $R^3$ may bond together to form a ring with the carbon atoms to which they are attached,

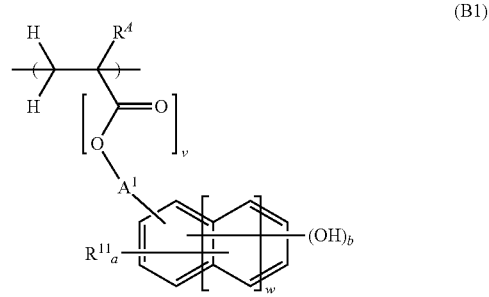

(B1)

wherein $R^A$ is hydrogen, fluorine, methyl or trifluoromethyl, $R^{11}$ is each independently halogen, an optionally halogenated $C_2$-$C_8$ straight, branched or cyclic acyloxy group, optionally halogenated $C_1$-$C_6$ straight, branched or cyclic alkyl group, or optionally halogenated $C_1$-$C_6$ straight, branched or cyclic alkoxy group, $A^1$ is a single bond or C$_1$-C$_{10}$ straight, branched or cyclic alkylene group in which an ether bond may intervene in a carbon-carbon bond, v is 0 or 1, w is an integer of 0 to 2, a is an integer satisfying 0≤a≤5+2w−b, and b is an integer of 1 to 3.

2. The positive resist composition of claim 1 wherein the polymer further comprises recurring units having the formula (B2):

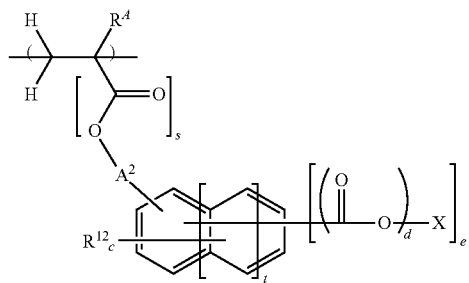

(B2)

wherein R$^A$ is as defined above, R$^{12}$ is each independently halogen, an optionally halogenated C$_2$-C$_8$ straight, branched or cyclic acyloxy group, optionally halogenated C$_1$-C$_6$ straight, branched or cyclic alkyl group, or optionally halogenated C$_1$-C$_6$ straight, branched or cyclic alkoxy group, A$^2$ is a single bond or C$_1$-C$_{10}$ straight, branched or cyclic alkylene group in which an ether bond may intervene in a carbon-carbon bond, s is 0 or 1, t is an integer of 0 to 2, c is an integer satisfying: 0≤c≤5+2t−e, d is 0 or 1, e is an integer of 1 to 3, in case of e=1, X is an acid labile group, and in case of e=2 or 3, X is hydrogen or an acid labile group, at least one X being an acid labile group.

3. The positive resist composition of claim 1 wherein the polymer further comprises recurring units of at least one type selected from units having the formulae (B3), (B4), and (B5):

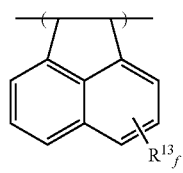

(B3)

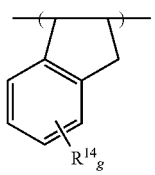

(B4)

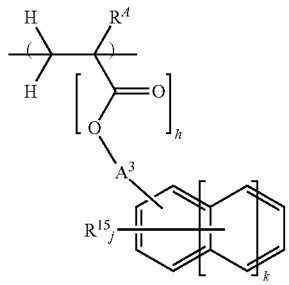

(B5)

wherein R$^A$ is as defined above, R$^{13}$ and R$^{14}$ are each independently a hydroxyl group, halogen atom, acetoxy group, optionally halogenated C$_2$-C$_8$ straight, branched or cyclic acyloxy group, optionally halogenated C$_1$-C$_8$ straight, branched or cyclic alkyl group, optionally halogenated C$_1$-C$_8$ straight, branched or cyclic alkoxy group, or optionally halogenated C$_2$-C$_8$ straight, branched or cyclic alkylcarbonyloxy group, R$^{15}$ is an acetyl group, acetoxy group, C$_1$-C$_{20}$ straight, branched or cyclic alkyl group, C$_1$-C$_{20}$ straight, branched or cyclic alkoxy group, C$_2$-C$_{20}$ straight, branched or cyclic acyloxy group, C$_2$-C$_{20}$ straight, branched or cyclic alkoxyalkyl group, C$_2$-C$_{20}$ alkylthioalkyl group, halogen atom, nitro group, cyano group, sulfinyl group, or sulfonyl group, A$^3$ is a single bond or C$_1$-C$_{10}$ straight, branched or cyclic alkylene group in which an ether bond may intervene in a carbon-carbon bond, f and g are each independently an integer of 0 to 4, h is 0 or 1, j is an integer of 0 to 5, and k is an integer of 0 to 2.

4. The positive resist composition of claim 1, further comprising (C) a polymer comprising recurring units having the formula (C1) and recurring units of at least one type selected from units having the formulae (C2), (C3), (C4), and (C5):

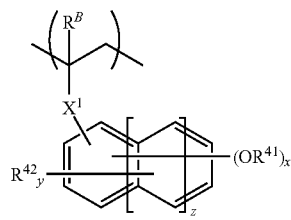

(C1)

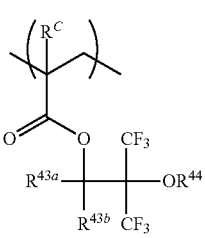

(C2)

-continued

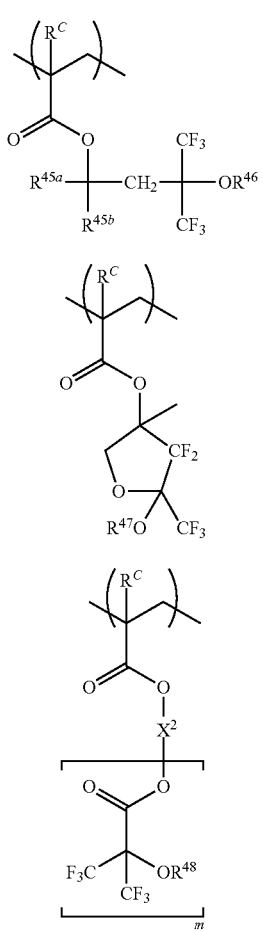

wherein $R^B$ is each independently hydrogen or methyl, $R^C$ is each independently hydrogen, fluorine, methyl or trifluoromethyl, $R^{41}$ is hydrogen or a $C_1$-$C_5$ straight or branched monovalent hydrocarbon group in which a heteroatom may intervene in a carbon-carbon bond, $R^{42}$ is a $C_1$-$C_5$ straight or branched monovalent hydrocarbon group in which a heteroatom may intervene in a carbon-carbon bond, $R^{43a}$, $R^{43b}$, $R^{45a}$ and $R^{45b}$ are each independently hydrogen or a $C_1$-$C_{10}$ straight, branched or cyclic alkyl group, $R^{44}$, $R^{46}$, $R^{47}$ and $R^{48}$ are each independently hydrogen, a $C_1$-$C_{15}$ straight, branched or cyclic monovalent hydrocarbon group or monovalent fluorinated hydrocarbon group, or an acid labile group, with the proviso that an ether or carbonyl moiety may intervene in a carbon-carbon bond in the monovalent hydrocarbon groups or monovalent fluorinated hydrocarbon groups represented by $R^{44}$, $R^{46}$, $R^{47}$ and $R^{48}$, x is an integer of 1 to 3, y is an integer satisfying: $0 \leq y \leq 5+2z-x$, z is 0 or 1, m is an integer of 1 to 3, $X^1$ is a single bond, —C(=O)—O— or —C(=O)—NH—, and $X^2$ is a $C_1$-$C_{20}$ straight, branched or cyclic (m+1)-valent hydrocarbon group or fluorinated hydrocarbon group.

5. The positive resist composition of claim 1, further comprising (D) an organic solvent.

6. A positive resist composition comprising (A) an acid diffusion inhibitor comprising a sulfonium compound having the formula (A), (B) a base polymer containing a polymer comprising recurring units having the formula (B1), adapted to be decomposed under the action of acid to increase its solubility in alkaline developer, and recurring units of at least one type selected from units having the formulae (B6), (B7), (B8), and (B9):

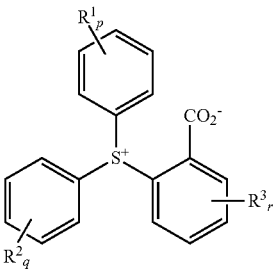

wherein $R^1$, $R^2$, and $R^3$ are each independently a $C_1$-$C_{20}$ straight, branched or cyclic monovalent hydrocarbon group which may contain a heteroatom, p and q are each independently an integer of 0 to 5, r is an integer of 0 to 4, in case of p=2 to 5, two adjoining groups $R^1$ may bond together to form a ring with the carbon atoms to which they are attached, in case of q=2 to 5, two adjoining groups $R^2$ may bond together to form a ring with the carbon atoms to which they are attached, in case of r=2 to 4, two adjoining groups $R^3$ may bond together to form a ring with the carbon atoms to which they are attached,

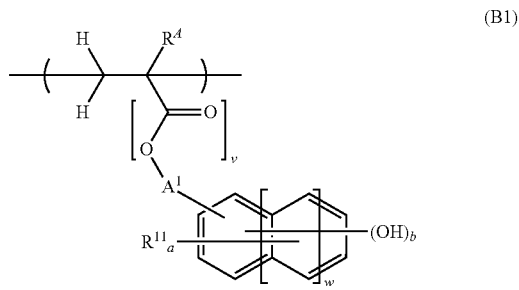

wherein $R^4$ is hydrogen, fluorine, methyl or trifluoromethyl, $R^{11}$ is each independently halogen, an optionally halogenated $C_2$-$C_8$ straight, branched or cyclic acyloxy group, optionally halogenated $C_1$-$C_6$ straight, branched or cyclic alkyl group, or optionally halogenated $C_1$-$C_6$ straight, branched or cyclic alkoxy group, $A^1$ is a single bond or $C_1$-$C_{10}$ straight, branched or cyclic alkylene group in which an ether bond may intervene in a carbon-carbon bond, v is 0 or 1, w is an integer of 0 to 2, a is an integer satisfying $0 \leq a \leq 5+2w-b$, and b is an integer of 1 to 3,

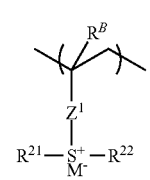

-continued

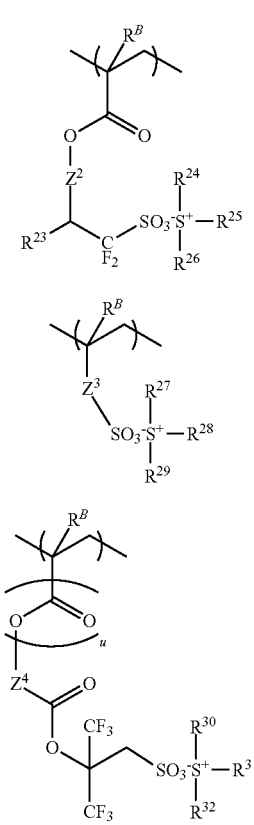

(B7)

(B8)

(B9)

wherein $R^B$ is each independently hydrogen or methyl, $Z^1$ is a single bond, phenylene group, —O—$Z^{12}$—, or —C(=O)—$Z^{11}$—$Z^{12}$—, $Z^{11}$ is —O— or —NH—, $Z^{12}$ is a $C_1$-$C_6$ straight, branched or cyclic alkylene, $C_2$-$C_6$ straight, branched or cyclic alkenylene or phenylene group, which may contain a carbonyl, ester, ether or hydroxy moiety, $Z^2$ is a single bond or —$Z^{21}$—C(=O)—O—, $Z^{21}$ is a $C_1$-$C_{20}$ straight, branched or cyclic divalent hydrocarbon group which may contain a heteroatom-containing moiety, $Z^3$ is a single bond, methylene, ethylene, phenylene, fluorinated phenylene, —O—$Z^{32}$—, or —C(=O)—$Z^{31}$—$Z^{32}$—, $Z^{31}$ is —O— or —NH—, $Z^{32}$ is a $C_1$-$C_6$ straight, branched or cyclic alkylene, $C_2$-$C_6$ straight, branched or cyclic alkenylene or phenylene group, which may contain a carbonyl, ester, ether or hydroxy moiety, $Z^4$ is a single bond or a $C_1$-$C_{30}$ straight, branched or cyclic divalent hydrocarbon group which may contain a heteroatom, u is 0 or 1, with the proviso that u is 0 when $Z^4$ is a single bond $R^{21}$, $R^{22}$, $R^{24}$, $R^{25}$, $R^{26}$, $R^{27}$, $R^{28}$, $R^{29}$, $R^{30}$, $R^{31}$, and $R^{32}$ are each independently a $C_1$-$C_{20}$ straight, branched or cyclic monovalent hydrocarbon group which may contain a heteroatom-containing moiety, or $R^{21}$ and $R^{22}$ may bond together to form a ring with the sulfur atom to which they are attached, or any two of $R^{24}$, $R^{25}$ and $R^{26}$, any two of $R^{27}$, $R^{28}$ and $R^{29}$ or any two of $R^{30}$, $R^{31}$ and $R^{32}$ may bond together to form a ring with the sulfur atom to which they are attached, $R^{23}$ is hydrogen or trifluoromethyl, and $M^-$ is a non-nucleophilic counter ion.

7. The positive resist composition of claim 6, further comprising (E) a photoacid generator.

8. A resist pattern forming process comprising the steps of:
applying the positive resist composition of claim 1 onto a processable substrate to form a resist film thereon,
exposing the resist film patternwise to high-energy radiation, and
developing the resist film in an alkaline developer to form a resist pattern.

9. The process of claim 8 wherein the high-energy radiation is EUV or EB.

10. The process of claim 8 wherein the processable substrate has an outermost surface of silicon-containing material.

11. The process of claim 8 wherein the processable substrate is a photomask blank.

12. A photomask blank having coated thereon the positive resist composition of claim 1.

* * * * *